United States Patent
Quimby et al.

(10) Patent No.: US 8,513,593 B2
(45) Date of Patent: Aug. 20, 2013

(54) IN-SITU CONDITIONING IN MASS SPECTROMETER SYSTEMS

(71) Applicants: Bruce D. Quimby, Loveland, CO (US); Michael J. Szelewski, Loveland, CO (US); Michael K. Freed, Loveland, CO (US); Harry F. Prest, Loveland, CO (US)

(72) Inventors: Bruce D. Quimby, Loveland, CO (US); Michael J. Szelewski, Loveland, CO (US); Michael K. Freed, Loveland, CO (US); Harry F. Prest, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/716,785

(22) Filed: Dec. 17, 2012

(65) Prior Publication Data
US 2013/0099113 A1 Apr. 25, 2013

Related U.S. Application Data

(63) Continuation of application No. 13/229,296, filed on Sep. 9, 2011, now Pat. No. 8,378,293.

(51) Int. Cl.
*H01J 49/00* (2006.01)
(52) U.S. Cl.
USPC ........... 250/282; 250/281; 250/284; 250/286; 250/288; 134/2; 134/21
(58) Field of Classification Search
USPC ............. 250/281, 282, 284, 286, 288; 134/2, 134/21
See application file for complete search history.

(56) References Cited

U.S. PATENT DOCUMENTS

| | | | | |
|---|---|---|---|---|
| 4,833,319 A * | 5/1989 | Knauer | ......................... | 250/251 |
| RE33,344 E * | 9/1990 | Stafford | ........................ | 250/281 |
| 4,994,096 A * | 2/1991 | Klein et al. | ........................ | 95/15 |
| 5,491,337 A | 2/1996 | Jenkins et al. | | |
| 5,830,353 A | 11/1998 | Henderson | | |
| 5,942,752 A * | 8/1999 | Wang | ............................ | 250/288 |
| 6,808,933 B1 * | 10/2004 | Prest | ............................ | 436/161 |
| 7,138,642 B2 * | 11/2006 | Hieke | ........................... | 250/400 |
| 7,264,677 B2 * | 9/2007 | Nakahara et al. | ................. | 134/2 |
| 7,276,688 B2 * | 10/2007 | Weiss | ............................ | 250/288 |
| 7,304,299 B2 | 12/2007 | Perkins | | |
| 7,399,958 B2 * | 7/2008 | Miller et al. | .................. | 250/286 |
| 7,482,584 B2 * | 1/2009 | Kampf et al. | ................. | 250/288 |
| 7,642,510 B2 * | 1/2010 | McEwen | ...................... | 250/288 |
| 7,812,307 B2 * | 10/2010 | Dutton et al. | ................ | 250/288 |
| 7,836,450 B2 | 11/2010 | Kissell | | |
| 7,836,750 B2 | 11/2010 | Van Den Heuvel et al. | | |
| 7,928,370 B2 * | 4/2011 | Amirav et al. | ................ | 250/288 |
| 8,210,026 B2 * | 7/2012 | Klee et al. | .................... | 73/23.27 |
| 2003/0160168 A1 | 8/2003 | Speakman et al. | | |
| 2007/0075240 A1 * | 4/2007 | Hieke | ........................... | 250/282 |
| 2007/0176092 A1 * | 8/2007 | Miller et al. | ................. | 250/288 |

(Continued)

*Primary Examiner* — David A Vanore

(57) ABSTRACT

In a mass spectrometer or gas chromatograph/mass spectrometer system, a conditioning gas such as, for example, hydrogen is added to condition or clean one or more components or regions of the mass spectrometer such as the ion source. The conditioning gas may be added upstream of the mass spectrometer such as, for example, into a sample inlet or a chromatographic column, or may be added directly into the mass spectrometer. The conditioning gas may be added off-line, when the mass spectrometer is not analyzing a sample, or on-line during sample analysis. When added on-line, the conditioning gas may be mixed with a carrier gas such as, for example, helium. In another embodiment, the conditioning gas also serves as the carrier gas through the column; another gas such as, for example, helium may be added to the carrier gas stream.

20 Claims, 28 Drawing Sheets

(56) References Cited

U.S. PATENT DOCUMENTS

2007/0224693 A1    9/2007  Prest
2008/0083874 A1*   4/2008  Prest et al. .................... 250/288
2008/0185512 A1*   8/2008  Miller et al. .................. 250/287
2009/0194679 A1    8/2009  Doherty et al.
2010/0154835 A1*   6/2010  Dimeo et al. ................... 134/31
2012/0048310 A1*   3/2012  Maekawa ...................... 134/105

* cited by examiner

IN-SITU CONDITIONING IN MASS SPECTROMETER SYSTEMS

RELATED APPLICATIONS

This application is a continuation of U.S. patent application Ser. No. 13/229,296, titled "IN-SITU CONDITIONING IN MASS SPECTROMETER SYSTEMS", filed Sep. 9, 2011, the content of which is incorporated herein by reference in its entirety.

TECHNICAL FIELD

The present invention relates generally to mass spectrometry, including mass spectrometry coupled with gas chromatography. More particularly, the invention relates to conditioning a mass spectrometer to improve or restore its performance.

BACKGROUND

A mass spectrometer (MS) typically includes an ion source for producing charged species from an introduced sample, a mass analyzer for separating the charged species according to their mass-to-charge ratios (m/z ratios, or simply "masses"), and an ion detector for counting the separated species to provide signals from which mass spectra may be produced. The sample may be introduced into the ion source by various techniques. In one example, a gas chromatograph (GC) is interfaced with the MS such that the sample output from the GC column—containing chromatographically separated sample components—serves as the sample input into the ion source. The latter system is often termed a GC/MS system.

As an MS continues to be operated over time, invariably some alteration or degradation in the performance of the MS occurs due to the samples, their matrix (e.g., heavy hydrocarbons in petroleum samples, triglycerides in fat samples) and solvents, stationary phase bleed from the GC column, or other recalcitrant substances, all of which may accumulate over time. Even at the initial operation of the MS, the MS may not be stabilized or "conditioned" to provide adequate or uniform performance. In the case of gas chromatography where an electron impact (EI) or chemical ionization (CI) source is typically utilized in the MS, the ion source can be rapidly fouled by the introduced sample components, which results in degraded performance as seen in the analyte signal or spectral characteristics. Another problem, especially with high-boiling analytes, is that peak tailing can increase with continued use in addition to reduced signal response. The degraded performance may be manifested in many ways but typically the metrics are reduced analyte signal response and high system background noise, the latter being particularly troublesome for analyte detection and identification.

These problems require that the MS be cleaned periodically. Generally, the higher the rate of contaminant deposition, the more often the MS must be cleaned. The common, conventional cleaning solution has been to vent the MS system, remove the critically affected components (e.g., ion source, ion optics, pre-filter, etc.), treat the removed components to mechanical and/or chemical cleaning followed by other processes (e.g., muffle or vacuum furnace baking), and then re-install the components in the MS system. Such conventional ex situ cleaning procedures can be quite complex and lengthy procedures, involving potentially toxic solvents, expensive equipment, and the time and care of skilled technicians. Moreover, the cleaning process only temporarily solves the problem. After performing an iteration of cleaning and resuming the analytical operation of the MS, the performance of the MS will start to degrade again, eventually requiring another iteration of cleaning. In addition, the conventional cleaning process may fail due to mechanical issues associated with the reinstallation of components, or because some step in the procedure was compromised (e.g., a cleaning solvent was contaminated). Such failures may not be discovered until the MS is reassembled, under vacuum, and at operating conditions. Also, the process of venting entrains certain background species, the most abundant of which is water, which results in additional time being required to eliminate these substances. Water as a contaminant can cause a rapid reduction in MS signal response.

Helium is the most commonly employed carrier gas in GC/MS due to helium's inertness, low mass, high ionization potential, and desirable chromatographic properties. Moreover, spectral reference libraries such as NIST 08 (National Institute of Standards and Technology) are recorded using helium as the carrier gas. Helium alone, however, does not possess any inherent cleaning or conditioning properties, and hence its use as a carrier gas cannot ameliorate the need for frequently carrying out the above-described cleaning procedures. It would thus be desirable to provide a solution to this problem that prevents the response loss and tailing that occurs when using helium as a carrier gas, and/or reduces or eliminates the need to clean the MS system by the above-described conventional techniques while still retaining the benefits of using helium as a carrier gas.

Hydrogen has also been employed as a carrier gas, but much more rarely than helium and other carrier gases. A number of significant disadvantages attend the use of hydrogen as a carrier gas. Hydrogen is highly combustible. The choice of column dimensions is severely limited with hydrogen due to its low viscosity. Much smaller columns are required to maintain a positive inlet pressure when the column outlet is an MS. The signal-to-noise ratio of a mass spectrum or chromatogram when using hydrogen as the carrier gas is much lower, resulting in detection limits that are five to ten times worse than when using helium as the carrier gas. The use of hydrogen can lead to degradation reactions of analytes in the ion source, resulting in a peak tail having a different composition than the apex of the associated peak. This comprises the spectral fidelity, which is an important factor in analyte identification when employing spectral library searches. Also, the presence of hydrogen in the sample inlet and the column can result in chemical reactions with analytes that change their structure.

In view of the foregoing, there is an ongoing need in mass spectrometry, including gas chromatography/mass spectrometry, for methods and apparatus for conditioning an MS system. There is also a need for methods and apparatus for in situ conditioning that is carried out at the MS system, whereby the need for conventional ex situ cleaning is eliminated or at least significantly reduced. There is also a need for methods and apparatus that make effective use of hydrogen and/or other gases in MS systems as an alternative to, or in conjunction with, more common gases such as helium.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for operating a mass spectrometer (MS) system includes introducing a sample and a carrier gas into an ionization chamber of the MS system; and flowing a conditioning gas into a mass spectrometer of the MS system, wherein the conditioning gas in the mass spectrometer does not substantially change the mass spectral characteristics of analytes of the sample, and the conditioning gas is different from the carrier gas.

According to another embodiment, a method for operating a mass spectrometer (MS) system includes flowing a conditioning gas into a mass spectrometer of the MS system without introducing a sample into the mass spectrometer, wherein the mass spectrometer is conditioned by the conditioning gas; and introducing a sample with a carrier gas into the conditioned mass spectrometer and collecting analytical data from the sample, wherein the carrier gas is different from the conditioning gas.

According to another embodiment, a method for operating a mass spectrometer (MS) system includes flowing a sample and a carrier gas through a column and into an ionization chamber of the MS system; and flowing a conditioning gas into a mass spectrometer of the MS system, wherein the conditioning gas is different from the carrier gas.

According to another embodiment, a method for operating a mass spectrometer (MS) system includes operating the MS system in an analytical mode by flowing a sample and a carrier gas through a column and into an ionization chamber of the MS system; ceasing operating the MS system in the analytical mode by ceasing the flowing of the sample; and operating the MS system in a conditioning mode to condition one or more components of the mass spectrometer by flowing a conditioning gas into the mass spectrometer, wherein the conditioning gas is different from the carrier gas. The conditioning gas may be, for example, hydrogen, argon, ammonia, and/or methane.

According to another embodiment, a method for operating a mass spectrometer (MS) system includes flowing a sample and a carrier gas through a column and into an ionization chamber of the MS system; while flowing the sample and the carrier gas, flowing a conditioning gas into a mass spectrometer of the MS system, wherein the conditioning gas is different from the carrier gas; and ionizing components of the sample in the ionization chamber. The conditioning gas may be, for example, hydrogen, argon, ammonia, and/or methane.

According to another embodiment, a method for operating a mass spectrometer (MS) system includes flowing a sample and a carrier gas through a column and into an ionization chamber of the MS system; while flowing the sample and the carrier gas, flowing an auxiliary gas into the ionization chamber, wherein the auxiliary gas is different from the carrier gas; and ionizing components of the sample in the ionization chamber. The carrier gas may be, for example, hydrogen, argon, ammonia, and/or methane.

According to another embodiment, a method for operating a mass spectrometer (MS) system includes flowing a sample and a carrier gas through a column and into an ionization chamber of the MS system, the carrier gas selected from the group consisting of hydrogen, argon, ammonia, and methane; while flowing the sample and the carrier gas, flowing an auxiliary gas into a mass spectrometer of the MS system, wherein the auxiliary gas is different from the carrier gas and is selected from the group consisting of helium, nitrogen, and argon; and ionizing components of the sample in the ionization chamber.

According to another embodiment, a mass spectrometer (MS) system, comprising a mass spectrometer and a conditioning gas system is configured for performing any of the above methods. The MS system may include a mass spectrometer and a conditioning system. The MS system may also include a gas chromatograph.

According to another embodiment, a mass spectrometer (MS) system includes a mass spectrometer including a sample interface and an ionization chamber communicating with the sample interface; a conditioning gas line configured for fluid communication with a conditioning gas source; a device or apparatus for operating in an analytical mode, configured for establishing a sample flow path through the sample interface and into the ionization chamber; and a device or apparatus for operating in a conditioning mode, configured for establishing a conditioning gas flow path from the conditioning gas source, through the conditioning gas line and into the mass spectrometer.

According to another embodiment, a mass spectrometer (MS) system includes a mass spectrometer including a sample interface and an ionization chamber communicating with the sample interface; a conditioning gas source; a conditioning gas line configured for fluid communication with a conditioning gas source and for directing a conditioning gas toward the mass spectrometer; and a device or apparatus for regulating respective flows of a carrier gas and the conditioning gas into the mass spectrometer.

According to another embodiment, a mass spectrometer (MS) system includes a mass spectrometer including a sample interface and an ionization chamber communicating with the sample interface, wherein the sample interface is configured for fluid communication with a carrier gas source and the carrier gas source is configured for supplying a carrier gas; an auxiliary gas line configured for fluid communication with a auxiliary gas source, wherein the auxiliary gas source is configured for supplying an auxiliary gas different from the carrier gas, and the auxiliary gas line is configured for adding the auxiliary gas to the carrier gas; and a device or apparatus for regulating respective flows of the carrier gas and the auxiliary gas into the ionization chamber such that the proportion of the auxiliary gas relative to the carrier gas flowing into the ionization chamber ranges from 0% to less than 100% by volume. The carrier gas may be hydrogen, argon, ammonia, and/or methane.

According to another embodiment, a computer-readable storage medium is provided that includes instructions for performing any of the above methods.

According to another embodiment, a mass spectrometer (MS) system is provided that includes the computer-readable storage medium.

In some embodiments, the conditioning gas may be or include hydrogen, argon, fluorine, oxygen, ammonia, and/or methane. In some embodiments, the carrier gas may be or include helium, nitrogen or argon. In some embodiments, the conditioning gas is or includes hydrogen and the carrier gas is or includes helium.

In other embodiments, the carrier gas is hydrogen, and an auxiliary gas such as, for example, helium, is added to the hydrogen.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
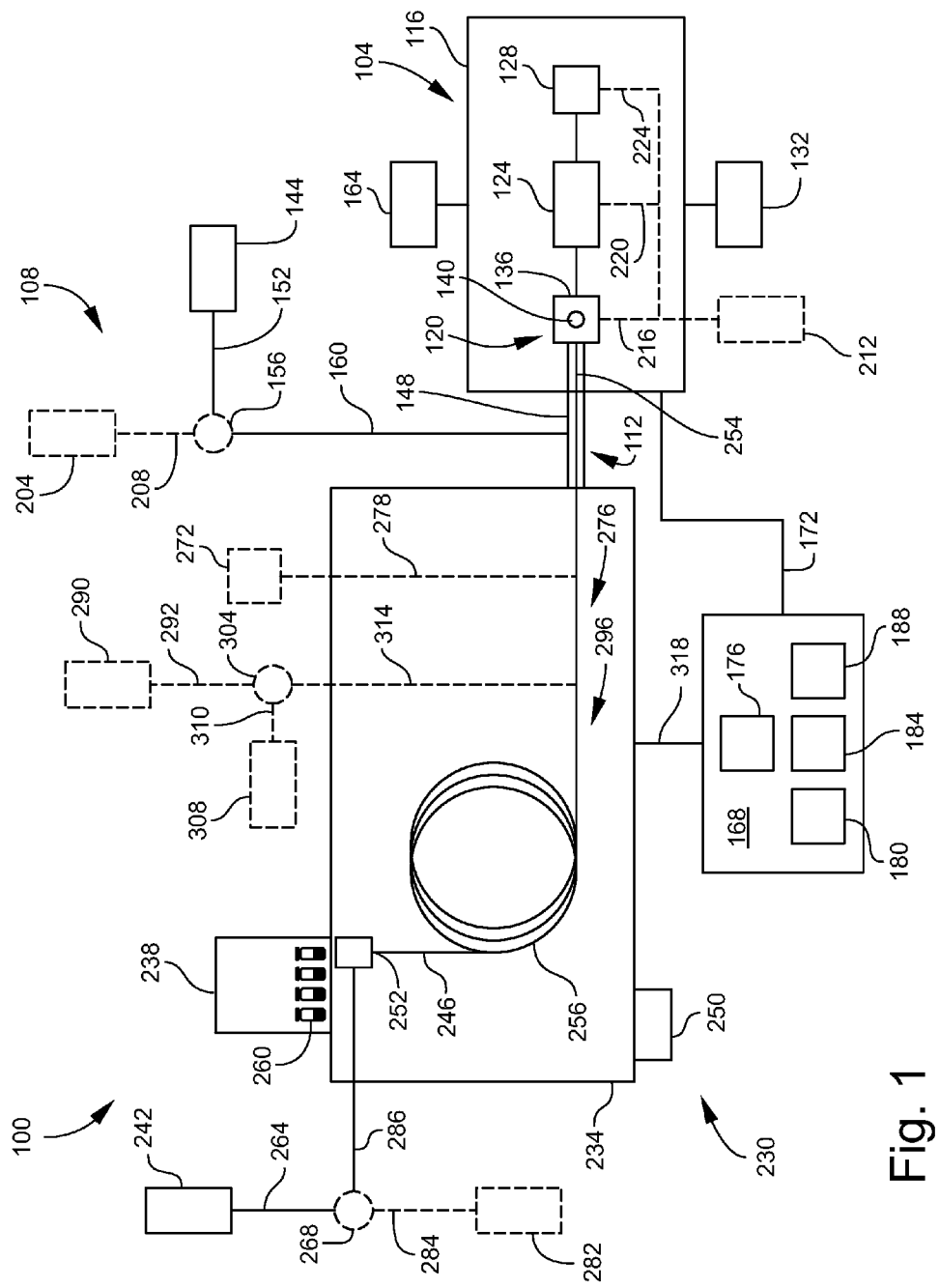
FIG. 1 is a schematic view of an example of a mass spectrometry (MS) system in accordance with the present disclosure.

As used herein, the term "mass spectrometer system" (or "MS system") refers to a system that includes a mass spectrometer with or without a gas chromatograph (GC) being operatively interfaced with the mass spectrometer. Thus, for convenience the term "MS system" may also encompass (or be used interchangeably with) the term "gas chromatograph/mass spectrometer system" (or "GC/MS system"), depending on the particular embodiment of interest.

In the context of the present disclosure, the term "analyte" refers generally to any sample molecule of interest to a researcher or user of an MS system—that is, a molecule on which an analysis is desired such as, for example, a chromatographic or chromatographic/mass spectral analysis. The term "sample" or "sample matrix" refers to any substance known or suspected of containing analytes. The sample may include a combination of analytes and non-analytes. The term "non-analytes" or "non-analytical components" in this context refers to components of the sample for which analysis is not of interest because such components do not have analytical value and/or impair (e.g., interfere with) the analysis of the desired analytes. Non-analytes may generally be any molecules not of interest such as contaminants or impurities. Examples of non-analytes may include, but are not limited to, water, oils, solvents or other media in which the desired analytes may be found, as well as stationary phase material that has bled from a chromatographic column. The source of non-analytes may be the sample being analyzed at the time of operating an MS system to acquire analytical data on the sample. Alternatively or additionally, non-analytes may be residual species already present in the mass spectrometer prior to operating the MS system to acquire analytical data at a given time, such residual species having accumulated as a result prior use(s) of the MS system.

For purposes of the present disclosure, the term "analyte" also refers to compounds that may be analyzed by the MS system for the purpose of providing a reference, standard, tuning vehicle, or calibrant.

The present disclosure describes various embodiments entailing the addition of a conditioning gas (or conditioning agent) to a mass spectrometer (MS) system to condition (or re-condition) the MS system in situ so as to improve or restore its performance. Without wishing to be bound by any particular theory at the present time, the conditioning gas may serve one or more of the following functions: cleaning one or more surfaces (e.g., walls, plates, electrodes, conduits) of one or more components of the MS system (e.g., ion source, mass analyzer(s), ion detector); reducing or removing non-analytes such as matrix components that have accumulated in the MS system after sample analysis, or that are accumulating in the MS system during sample analysis; preventing further accumulation of non-analytes during a sample analysis; accelerating the conditioning of the MS system after a vent/pump-down procedure; and restoring or creating an ion source condition (e.g., surface oxidation state or other surface metric) more optimal or consistent for MS analysis. The inventors have found hydrogen to be highly effective as a conditioning agent in an MS environment. Hydrogen rapidly diffuses and displaces surface contaminants. Hydrogen when dissociated or in higher excited, meta-stable or pseudo-Rydberg states (such as by electron impact or other processes) is very active and can reduce many adsorbed compounds, such as those that tend to become adsorbed on ion source surfaces and degrade operation. Moreover, hydrogen can alter metal oxidation states. The metal surfaces of an MS system are known to participate in a variety of reactions that affect the analytes and other introduced compounds, such as dehydration or reduction as occur in the ion source. By converting the metals from a range of oxidation states to a reproducible and fixed set, performance can be made more consistent. In the case of the ion source, spectral characteristics can be greatly stabilized. These conditioning attributes of hydrogen have not been fully appreciated by previous researchers, due to the above-noted challenges attending the use of hydrogen. More generally, the concept of adding a conditioning gas to an MS system has not been adequately investigated prior to the present work. This may be evidenced by the observation that, to date, efforts made toward improved conditioning techniques have largely been limited to enhancing the removability of components to facilitate conventional ex situ cleaning—that is, shutting down the MS system physically removing components from the MS system for the purpose of cleaning them—as well as exploring alternative compositions of surfaces of the ion source in an attempt to reduce the need for conventional ex situ cleaning.

Generally, the conditioning gas may be any gas suitable for performing one or more of the foregoing functions in an MS system or exhibiting the same or similar conditioning attributes as hydrogen. Thus, in addition to hydrogen, other examples of conditioning gases include, but are not limited to, argon, fluorine, oxygen, ammonia, methane, and combinations of two or more of hydrogen, argon, fluorine, oxygen, ammonia and methane. The specific conditioning gas(es) utilized may depend on whether the conditioning process is performed in an on-line mode or off-line mode; these modes are described below. The conditioning gas may be a single gas or a mixture of gases provided by gaseous or volatile liquid sources. In the present context, the term "gas" encompasses the term "vapor." The conditioning gas introduced into the MS system may be in addition to any other intentionally added gases such as, for example, a carrier gas for chromatography, reagent gases for chemical ionization, and collision gases for ion fragmentation in a collision cell or ion trap or for collisional cooling in an ion guide or ion trap. Alternatively, the conditioning gas may be added exclusively depending on its nature and the specific state of the MS system. The conditioning gas added to the MS system may be part of a blend that includes a carrier gas or some other gas (e.g., an auxiliary gas as described further below). Depending on the type of conditioning gas, the particular embodiment being implemented, or the stage of the MS system at which the conditioning gas is present, the conditioning gas molecules may be heated, electrically neutral, in a metastable, Rydberg or other excited state, or ionized.

In some embodiments, the MS system that is configured for carrying out in situ conditioning is part of a gas chromatograph/mass spectrometer (GC/MS) system and thus is interfaced with a gas chromatograph (GC). In such embodiments, the conditioning gas may be routed through a part of the GC prior to being introduced into the MS system. In some embodiments, the conditioning gas is introduced directly into the ion source. Moreover, the conditioning gas may be introduced into one or more locations of the MS system and/or the GC. For this purpose, more than one discrete source of conditioning gas (or at least more than one conditioning gas line) may be utilized.

In some embodiments, the MS or GC/MS system is configured for carrying out an off-line conditioning mode. In the off-line conditioning mode, the conditioning gas is introduced into the MS or GC/MS system during a time when the MS or GC/MS system is not being operated in an analytical mode, i.e., is not being operated to perform mass spectrometry or gas chromatography/mass spectrometry on a sample to acquire analytical data. In such embodiments, the MS or GC/MS system may be configured to switch between the analytical mode and the conditioning mode. Execution of the switch from one mode to the other may be entirely or partially manual, or entirely or partially automated such as in response evaluating one or more parameters as described further below. Generally, in the off-line mode, conditioning gas may added during any stage of operation not involving the acquisition of analytical data on a sample, such as warm-up, tuning, pump-down, venting, cool-down, etc. Moreover, the off-line mode may entail adding the conditioning gas while one or more components (e.g., the ion source) of the MS or GC/MS system are removed.

In other embodiments, the MS or GC/MS system is configured for carrying out an on-line (or dynamic) conditioning mode. In the on-line conditioning mode, the conditioning gas is introduced into the MS or GC/MS system while the MS or GC/MS system is being operated to perform mass spectrometry or gas chromatography/mass spectrometry on a sample. One or more parameters associated with the on-line conditioning mode may be adjusted dynamically in response to the operating conditions of the MS or GC/MS system. In some embodiments, the MS or GC/MS system is configured for carrying out both the off-line and on-line conditioning modes.

In addition to flowing the conditioning gas into the MS system, the conditioning mode may include maintaining one or more regions of the MS system or GC/MS system being subjected to the conditioning gas (e.g., ion source, mass analyzer, ion detector, column) at a desired temperature or within a desired temperature range. The conditioning process may be enhanced by heating the conditioning gas and/or the surfaces being treated by the conditioning gas. In addition, the conditioning mode may include operating the ion source to emit electrons into the ionization chamber. The presence of the electrons may enhance the conditioning process by one or more mechanisms, such as "activating" or generating secondary species from the conditioning gas that promote the cleaning of surfaces.

In another embodiment, a conditioning gas such as hydrogen is utilized as a carrier gas for transporting a sample through a GC column instead of a more traditional carrier gas such as helium. An auxiliary gas, such as helium, is added to the stream of hydrogen carrier gas at some point upstream of the ion source, and the mixed gas flow enters the ion source. This configuration has also been found to be effective as an on-line conditioning technique.

In the context of the present disclosure, the term "conditioning" generally refers to cleaning or otherwise bringing an ion source and/or other components or regions of a mass spectrometer to a condition that improves or optimizes the performance of the mass spectrometer. In one aspect, conditioning is accomplished by operating the MS system to flow a conditioning gas into a mass spectrometer of the MS system. The addition of the conditioning gas in the mass spectrometer does not substantially change the mass spectral characteristics (or spectral response) of analytes of a sample being analyzed by the MS system during an on-line conditioning process, or of a sample that would be analyzed by the MS system after an off-line conditioning process. That is, the spectral characteristics of the analytes remain substantially unchanged with or without the addition of the conditioning gas. Stated in another way, the conditioning gas does not substantially change the ion abundance ratios of analytes. Instead, the conditioning gas cleans the mass spectrometer and keeps non-analytes from accumulating in the mass spectrometer. For these purposes, in a typical embodiment contemplated for the on-line conditioning mode, the conditioning gas may be, for example, hydrogen, argon, or a blend (mixture) of hydrogen and argon. In the off-line conditioning mode, generally a wider range of conditioning gases are contemplated such as, for example, hydrogen, argon, fluorine, oxygen, ammonia, and/or methane.

The conditions or parameters under which the conditioning gas is added may be controlled to enable the conditioning gas to effect conditioning without substantially changing analyte spectral response. As an example, the concentration of the conditioning gas in the mass spectrometer may be controlled, such as by regulating the flow rate of the conditioning gas into the mass spectrometer. Regulation of the flow rate of the conditioning gas may be relative to other gases being flowed into the mass spectrometer. Other conditions or parameters may include the temperature of the conditioning gas, the temperature and/or pressure in the region or component of the mass spectrometer in which the conditioning gas is being utilized, and the extent to which the conditioning gas has been made energetic such as through operation of the ion source.

It thus can be seen that because the addition of the conditioning gas does not substantially change analyte spectral response, the addition of the conditioning gas does not cause chemical ionization (CI). Accordingly, in the context of the present disclosure, the conditioning gas is not a CI reagent gas.

In some embodiments in which the MS system includes a GC, the conditioning gas may be added to the mass spectrometer by flowing the conditioning gas through the analytical column of GC. It will be understood, however, that process of "conditioning" the mass spectrometer as taught in the present disclosure is not the same as the process of "conditioning" or "pre-conditioning" the analytical column. Conditioning or pre-conditioning the analytical column typically involves running a solvent through the column to activate components of the stationary phase and/or purging the column of impurities in preparation for a chromatographic experiment, and hence is a separate and different process unrelated to the presently disclosed conditioning process.

FIG. 1 is a schematic view of an example of a mass spectrometer (MS) system 100. The MS system 100 may generally include a mass spectrometer 104 and a conditioning gas system 108. The mass spectrometer 104 may include a sample source, a sample (or sample/carrier gas) inlet or interface 112, an MS housing 116, an ionization apparatus (or ion source) 120, a mass analyzer 124, an ion detector 128, and a vacuum system 132.

The sample source may be any device configured for providing a stream of sample material to the ion source 120 via the sample interface 112. As examples, the sample source may be associated with a batch volume, a sample probe, or a liquid handling system. The flow of the sample material to the ion source 120 may be effected by any means, such as pumping, capillary action, or an electrically-assisted technique. In hyphenated techniques, the sample source may be associated with the output of an analytical separation instrument such as a gas chromatograph (GC) instrument, a liquid chromatographic (LC) instrument, a capillary electrophoresis (CE) instrument, a capillary electrochromatography (CEC) instrument, or the like. In some embodiments, the sample may be introduced or loaded directly into the ion source 120, without having to flow the sample from a sample source and through a column or conduit. In these embodiments, the sample inlet or sample interface to the ion source 120 may be, for example, a direct insertion probe. Depending on the technique employed to introduce the sample directly into the ion source, a carrier gas may or may not be utilized to assist in the sample introduction.

The ion source 120 may be any apparatus suitable for producing analyte ions from a sample stream received from the sample source and directing the as-produced ions into the mass analyzer 124. For example, the ion source 120 may be an electron impact (EI) apparatus or a chemical ionization (CI) apparatus. The ion source 120 may also include the capability of switching between EI and CI modes of operation. The ion source 120 includes an ionization chamber 136 and an ionization device 140. In the case of EI or CI, the ionization device 140 is typically a filament configured for emitting electrons in a manner understood by persons skilled in the art. The present disclosure, however, is not limited to EI and CI, and may encompass various other modes of ionization now known or later developed. In some embodiments, the ion source 120 is not one that ionizes samples with plasma, such as an inductively coupled plasma (ICP) ion source, particularly for operating the on-line methods.

In the case of CI, the MS system 100 additionally includes a CI reagent gas source 144 that typically communicates with a conduit 148 of the sample interface 112 via a reagent gas line 152. The reagent gas source 144 may represent one or more containers for supplying one or more different types of reagent gases. The reagent gas may be any gas suitable for conducting CI in the ionization chamber 136 as appreciated by persons skilled in the art. Examples of reagent gases include, but are not limited to, methane, isobutane, ammonia, carbon dioxide, dichlorodifluoromethane, trimethylsilane, nitric oxide, and methyl amine. The flow of the reagent gas may be controlled by any means, such as a gas flow controller (or flow control module) 156. The flow controller 156 may, for example, include one or more valves, restrictors, mass flow controllers, pressure regulators, or the like. The flow controller 156 may be manually or electronically controlled. In some embodiments, the flow controller 156 may be a programmable electronic pneumatic controller (EPC) of known design and operation. In the illustrated example, the reagent gas is supplied to the ionization chamber 136 via a reagent gas path that runs from the reagent gas source 144, through the reagent gas line 152 to the flow controller 156, through an auxiliary gas line 160 to the conduit 148 (via a port of the conduit 148), and into the ionization chamber 136.

The mass analyzer 124 may be any device configured for separating, sorting or filtering analyte ions on the basis of their respective masses (i.e., mass-to-charge ratios, or m/z ratios). Examples of mass analyzers 124 include, but are not limited to, multipole electrode structures (e.g., mass filters, ion traps), time-of-flight (TOF) components, electrostatic analyzers (ESAs), and magnetic sectors. The mass analyzer 124 may include a system of more than one mass analyzer, particularly when ion fragmentation is desired. As examples, the mass analyzer 124 may be a tandem MS or MS$^n$ system, as appreciated by persons skilled in the art. As another example, the mass analyzer 124 may include a mass filter followed by a collision cell, which in turn is followed by another mass filter. As another example, the mass analyzer 124 may comprise an ion mobility spectrometer (IMS). In some embodiments, however, the MS system 100 does not comprise an IMS.

The ion detector 128 may be any device configured for collecting and measuring the flux (or current) of mass-discriminated ions outputted from the mass analyzer 124. Examples of ion detectors 128 include, but are not limited to, electron multipliers, photomultipliers, and Faraday cups.

The ion source 120, mass analyzer 124, and ion detector 128 are disposed in the MS housing 116 with which the vacuum system 132 is interfaced. The MS housing 116 and vacuum system 132 are structured to define successive vacuum stages in the mass spectrometer 104. By this configuration the ion source 120, depending on design, is maintained at a desired low pressure or vacuum level, and the mass analyzer 124 and ion detector 128 are maintained at desired vacuum levels. For a mass analyzer 124 that includes multiple components or modules such as noted above, each component or module may be maintained at a different vacuum level. As an example, a collision cell is typically held at a higher pressure than the evacuated mass filters that precede or succeed the collision cell. For the foregoing purposes, the vacuum system 132 typically includes one or more vacuum pumps that communicate with one or more vacuum stages via one or more exhaust ports of the MS housing 116.

The mass spectrometer 104 may also include a heating system 164. The heating system 164 may include one or more heating devices configured for controlling the respective temperatures of one or more components of the mass spectrometer 104, such as the sample interface 112, ionization chamber 136, mass analyzer 124, and ion detector 128. A given heating device may be configured for direct heating such as a resistive heating element, or indirect heating such as system for routing a heat exchanging medium.

The MS system 100 may also include a system controller (or system control module) 168. The system controller 168 may be configured for controlling and/or monitoring various aspects of the MS system 100, such as sample introduction into the ionization chamber 136, reagent gas introduction (if applicable) and selection of reagent gases, sample ionization, selection of EI or CI modes of operation, vacuum and pressure settings, temperature settings or varying temperature profiles implemented by the heating system 164, operating parameters of the mass analyzer 124 (e.g., applied electric and/or magnetic fields, collision/background gas introduction, timing of ion optics, and the like), acquisition and analysis of signals from the ion detector 128, generation and display of mass spectra or chromatograms, and so on. For these purposes, the system controller 168 is schematically illustrated as being in signal communication with the mass spectrometer 104 via a communication link 172. The communication link 172 may be representative of several communication links respectively interfacing with various components of the MS system 100. A given communication link may be wired or wireless. Also for these purposes, the system controller 168 may include one or more types of hardware, firmware and/or software, as well as one or more types of memory. In the illustrated example, the system controller 168 includes an electronic processor 176, a database 180 stored in memory, gas flow control software 184, and performance evaluation software 188, as described further below. The system controller 168 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor 176 (e.g., logic instructions embodied in software, data, and the like). The system controller 168 may include an operating system (e.g., Microsoft Windows® software) for controlling and managing various functions of the system controller 168. One or more components of the system controller 168 may be located remotely from the MS system 100 and communicate with the local portion of the system controller 168 over a wired or wireless communication link. In some embodiments, the system controller 168 may include or be part of a laboratory information management system (LIMS), e.g., as may be utilized in a hospital or other medical setting.

The conditioning gas system 108 is configured for directing a conditioning gas into the MS system 100. For this purpose, the conditioning gas system 108 may include a conditioning gas source in communication with a conditioning gas line, and a gas flow controller as appropriate. As noted above, the conditioning gas may be, for example, hydrogen, argon, ammonia, and/or methane. The conditioning gas system 108 may be configured for directing the conditioning gas to one or more locations of the MS system 100. Various alternatives are depicted by dashed blocks and lines in FIG. 1. Thus, in one embodiment, a conditioning gas source 204 and an associated conditioning gas line 208 communicate with the gas flow controller 156 that also regulates the flow of reagent gas from the reagent gas source 144. In this embodiment, the conditioning gas is flowed into the auxiliary gas line 160, through the conduit 148 and into the ionization chamber 136. In another embodiment, a conditioning gas source 212 and an associated conditioning gas line 216 communicate directly with the ionization chamber 136, whereby the conditioning gas is flowed directly into the ionization chamber 136. In another embodiment, the conditioning gas source 212 and an associated conditioning gas line 220 communicate directly with the mass analyzer 124, or with one or more components of a multi-component mass analyzer 124. For instance, the conditioning gas may be introduced into a collision cell, a mass filter, an ion guide, or two or more of such mass analyzer components. In another embodiment, the conditioning gas source 212 and an associated conditioning gas line 224 communicate directly with an appropriate region of the ion detector 128. The conditioning gas system 108 may include a single conditioning gas source 212 that communicates with one of the foregoing locations, or may include two or more conditioning gas sources 212 (or at least two or more conditioning gas lines 216, 220, 224) that respectively communicate with two or more of the foregoing locations. It will be noted that one conditioning gas source 212 is illustrated in FIG. 1 for simplicity; each of the conditioning gas lines 216, 220, 224 may be associated with a different conditioning gas source. It will also be noted that a gas flow controller (not shown) may be placed in communication with one or more of the conditioning gas lines 216, 220, 224, and may have the same or similar configuration as the gas flow controller 156 associated with the reagent gas source 144. Any of the gas flow controllers provided in the MS system 100 may be manually operated and/or controlled by the system controller 168, such as by the electronic processor 176 in accordance with instructions provided by the gas flow control software 184.

In all of the foregoing embodiments, the conditioning gas system 108 provides a conditioning gas flow path from the conditioning gas source(s) 204 and/or 212, through the conditioning gas line(s) 208, 216, 220 and/or 224, and into the mass spectrometer 104. The conditioning gas flow path runs either directly into one or more locations of the mass spectrometer 104 or from a location upstream of the mass spectrometer 104. In any of these embodiments, the conditioning gas may flow or diffuse from the MS component into which it first directly entered to one or more of the other MS components. For example, the conditioning gas supplied directly into a collision cell may flow or diffuse to a preceding and/or succeeding mass filter. For another example, the conditioning gas supplied directly into a component of the mass analyzer 124 may flow or diffuse into the ionization chamber 136 and/or the ion detector 128. In some embodiments (described further below), the conditioning gas flow path may be established while the MS system 100 is being actively operated in an analytical mode, i.e., while sample and ion flow paths are established in a direction generally from the ionization chamber 136 toward the mass analyzer 124. Even in these embodiments, a sufficient amount of the conditioning gas injected directly into the mass analyzer 124 may diffuse in the opposite direction into the ionization chamber 136 and be effective for conditioning/cleaning surfaces of the ionization chamber 136.

FIG. 1 also illustrates an embodiment in which the MS system 100 includes a gas chromatograph (GC, or GC system) 230 or, stated differently, is part of a gas chromatograph/mass spectrometer (GC/MS) system. In such an embodiment, the MS system 100 may alternatively be characterized as being interfaced with the GC 230 via the sample interface 112, which in this case may also be termed a GC/MS interface. The GC 230 may generally include a GC housing 234, a sample introduction device 238 typically mounted at the GC housing 234, a carrier gas source 242, a column (or GC column) 246 disposed in the GC housing 234, and a heating device 250.

The column 246 includes a column inlet 252 communicating with the sample introduction device 238 via a sealed fluid connector, and a column outlet 254 communicating with the ionization chamber 136. A portion of the column 246 may extend through the sample interface 112 and into the ionization chamber 136, such that the column outlet 254 is located in the ionization chamber 136. Alternatively or equivalently, the column 246 may be coupled to a transfer line via a sealed fluid connector, in which case the transfer line extends through the sample interface 112 and into the ionization chamber 136. The column 246 includes a stationary phase, which typically comprises a liquid or polymer held on a solid support or film lining the inside wall of the column 246. A variety of compositions may be selected for the stationary phase, and a range or porosities or densities may be selected for the stationary phase, as appreciated by persons skilled in the art. To conserve space while maintaining a desired length, the column 246 may include a coiled section 256.

The sample introduction device 238 typically includes a device for injecting the sample into the column inlet 252, and may include a device for vaporizing the sample. The sample may be a matrix that includes sample material to be analytically separated in the column 246 and one or more solvents. The sample introduction device 238 may be in fluid communication with a separate sample source (not shown) or may function as the sample source. For instance, the sample introduction device 238 may be configured to receive one or more sample containers 260, and may include a device (e.g., a carousel) for selecting a desired sample for injection into the column 246.

The carrier gas source 242 may communicate with the column inlet 252 via a carrier gas line 264. The carrier gas line 264 may be coupled to a portion of the sample introduction device 238 at a point upstream of the column inlet 252. The carrier gas may be any gas suitable for serving as an inert mobile phase that facilitates transport of the sample through the column 246 as appreciated by persons skilled in the art. Examples of carrier gases include, but are not limited to, helium, nitrogen, argon, or in some embodiments hydrogen. The flow of the carrier gas may be controlled by any means, such as a gas flow controller 268. The flow controller 268 may have the same or similar configuration as the flow controller 156 associated with the reagent gas source 144. In the illustrated example, the carrier gas is supplied to the column 246 via a carrier gas path that runs from the carrier gas source 242, through the carrier gas line 264 to the flow controller 268, and into the column inlet 252 (possibly via the sample introduction device 238 as noted above).

The heating device 250 may have any configuration suitable for maintaining the column 246 at a desired temperature setting or for varying the temperature of the column 246 according to a desired (i.e., predetermined) temperature profile (or temperature program). In one example, the GC housing 234 is (or contains) an oven, and the heating device 250 is configured for heating the interior of the oven through which the column 246 extends. In another example, the heating device 250 is configured for heating the column 246 directly. For instance, the heating device 250 may include a resistive heating element mounted in thermal contact with the column 246.

When the GC is included, the MS system 100 may also include additional means for analyzing the components of the sample that are separated by the column 246, i.e., an analyzing instrument that is in addition to the mass spectrometer 104. Thus, in the illustrated embodiment the MS system 100 includes an optional gas detector 272 of any suitable type, which is typically positioned outside the GC housing 234. The gas detector 272 may be the type capable of producing a spectrum or chromatogram, such as a flame ionization detector (FID) or thermal conductivity detector (TCD). The gas detector 272 may communicate with a section 276 of the column 246 between the coiled section 256 and the column outlet 254 via a gas outlet line 278. A flow splitter (not shown) may be located in-line with the column 246 at this section 276 for this purpose. By this configuration, the sample/gas flow in the column 246 from the coiled section 256 is split into a first output flow directed into the ionization chamber 136 and a second output flow directed via the gas outlet line 278 into the gas detector 272.

With the GC 230 coupled to the MS system 100, additional embodiments are presented for configuring the conditioning gas system 108 to direct conditioning gas into the MS system 100. Generally, these additional embodiments entail introducing the conditioning gas at one or more locations upstream of the ionization chamber 136, by establishing one or more conditioning gas flow paths that run at least partially through the GC housing 234. In some embodiments, the conditioning gas flow path(s) may run through at least a portion of the column 246. Various alternatives are depicted by dashed blocks and lines in FIG. 1. Thus, in one embodiment, a conditioning gas source 282 and an associated conditioning gas line 284 communicate with the gas flow controller 268 that also regulates the flow of carrier gas from the carrier gas source 242. In this embodiment, the conditioning gas is flowed from the flow controller 268 into a common gas inlet line 286 and into the column inlet 252. The flow controller 268 may be utilized to regulate the respective flows (e.g., flow rates) of the carrier gas and the conditioning gas into the column 246. Depending on the particular conditioning strategy being implemented, the proportion of the carrier gas relative to the conditioning gas flowing into the column 246 generally ranges from 0% to less than 100% by volume. That is, the flow controller 268 may be operated to shut off the flow of carrier gas completely while the conditioning gas is flowed into the column 246, or to mix the carrier gas and the conditioning gas wherein both gases flow through the gas inlet line 286 in desired proportions. In another example, the proportion of the conditioning gas in the mixed flow ranges from 0.02% to 50%. In another example, the proportion of the conditioning gas ranges from 0.05% to 40%. In another example, the proportion of the conditioning gas ranges from 0.25% to 10%. These exemplary ranges may be employed in other embodiments in which the conditioning gas is introduced elsewhere in the MS system 100, and more generally apply to regulating the flow of conditioning gas into the mass spectrometer 104. Moreover, these exemplary ranges may be employed in various embodiments entailing either on-line mode or off-line mode.

In another embodiment, a conditioning gas source (not shown) and associated conditioning gas line (not shown) communicate with a section (not shown) of the column 246 between the column inlet 252 and the column outlet 254, such as between the column inlet 252 and the coiled section 256, at the coiled section 256, or between the coiled section 256 and the column outlet 254. By way of example, in FIG. 1 a conditioning gas source 290 and associated conditioning gas line 292 communicate with a section 296 of the column 246 between the coiled section 256 and the column outlet 254 (or between the coiled section 256 and the sample interface 112). Any structure or device suitable for merging the respective gas flows at a desired column section may be utilized, such as a tee connection, a union, or the like. As in other embodiments, a suitable flow controller 304 may be provided in-line with the conditioning gas line 292 to regulate the flow of conditioning gas. As in other embodiments in which the conditioning gas is added to the carrier gas, the proportion of the conditioning gas may be regulated in accordance with the examples of ranges set forth above.

The conditioning gas system 108 may include a single conditioning gas source that communicates with one of the foregoing locations of the GC 230, or may include two or more conditioning gas sources (or at least two or more conditioning gas lines) that respectively communicate with two or more of the foregoing locations of the GC 230, or with two of more of the above-described locations of the GC 230 and the MS system 100. As in the case of other flow controllers described above, any of the flow controllers (e.g., 268, 304) associated with the GC 230 may be manually operated and/or controlled by the system controller 168, such as by the electronic processor 176 in accordance with instructions provided by the gas flow control software 184.

In some embodiments, a given conditioning gas source 204, 212, 282, 290 may include a blend of the conditioning gas and an auxiliary gas. For example, the conditioning gas source 204, 212, 282, 290 may be provided in the form of a single tank that contains the blend, such that the MS system 100 does not need to provide a device for mixing the conditioning gas and the auxiliary gas together. The proportion of the conditioning gas relative to the auxiliary gas contained in the conditioning gas source 204, 212, 282, 290 may range from 0% to less than 100% by volume. In another example, the proportion of the conditioning gas relative to the auxiliary gas ranges from 0.05% to 20%. In another example, the proportion of the conditioning gas relative to the auxiliary gas ranges from 0.25% to 10%. The composition of the auxiliary gas may be the same as or different from that of the carrier gas being utilized. The auxiliary gas may generally be any inert gas (i.e., a gas that does not react with the sample or otherwise adversely affect the performance of the mass spectrometer 104) that is different from the conditioning gas. Examples of auxiliary gases include, but are not limited to, helium, nitrogen, and argon. The composition of the auxiliary gas may be the same as that of the carrier gas also being utilized in the MS system 100, or may be different. Some examples of uses of the auxiliary gas are described in the EXAMPLES below.

In another embodiment, an auxiliary gas source 308 and associated auxiliary gas line 310 are provided to enable the conditioning gas to be blended with the auxiliary gas. Thus, the flow controller 304 may be configured for regulating the respective flows of the auxiliary gas and the conditioning gas such that the proportion of the auxiliary gas relative to the conditioning gas in the mixed flow ranges from 0% to less than 100% by volume. In another example, the proportion of the auxiliary gas relative to the conditioning gas ranges from 0.05% to 80%. In another example, the proportion of the auxiliary gas relative to the conditioning gas ranges from 0.25% to 20%. In the illustrated example, the auxiliary gas line 310 communicates with the flow controller 304 with which the conditioning gas source 290 also communicates. In this example, the conditioning gas—or a blend or mixture of the conditioning gas and the auxiliary gas—is flowed to the column section 296 via a common gas inlet line 314. It will be understood that any of the other conditioning gas sources described herein and/or illustrated in FIG. 1 may likewise be associated with an auxiliary gas source for establishing a mixed flow of conditioning gas and auxiliary gas to a given location of the MS system 100.

In addition to interfacing with components of the mass spectrometer 104 and the conditioning gas system 108, the system controller 168 may be configured for controlling and/or monitoring various aspects of the GC 230, such as sample introduction into the column 246, column leakage events, pressure settings, temperature settings or varying temperature profiles implemented by the heating device 250, operation of the gas detector 272 (if provided), acquisition and analysis of signals from the gas detector 272, generation and display of spectra or chromatograms derived from the gas detector 272, and so on. For these purposes, the system controller 168 is schematically illustrated as being in signal communication with the GC 230 via a communication link 318, which may be wired or wireless and may represent one or more dedicated communication links to individual components of the GC 230. It can be seen that the system controller 168 schematically depicted in FIG. 1 may represent one or more means or devices for coordinating or synchronizing the various operations of the mass spectrometer 104 and the GC 230, as well as the conditioning gas system 108.

The MS system 100 includes means (or apparatus) for operating the MS system 100 in an analytical mode. In the analytical mode, the MS system 100 processes one or more samples to produce one or more mass spectra or chromatograms from which information regarding analytes of the sample(s) may be obtained. In some embodiments, the means for operating in the analytical mode may be configured for establishing a sample flow path through the sample interface 112 and into the ionization chamber 136. As an example, the sample is introduced into the ionization chamber 136 and the ionization device 140 operated to produce analyte ions from the sample. The analyte ions are transported into the mass analyzer 124, which sorts the ions according to mass—and, depending on design, possibly performs one or more iterations of ion fragmentation—as appreciated by persons skilled in the art. The resulting mass-discriminated ions are then transported to the ion detector 128, which is typically configured to convert the ion currents into electrical signals. The electrical signals are transmitted to a data analyzer, schematically represented by the system controller 168, for processing and generation of a mass spectrum or chromatogram. Accordingly, the means for operating in the analytical mode may include one or more of the following components: the sample interface 112; the ionization chamber 136; other components of the MS system 100 utilized in the processing of samples and production of mass spectra or chromatograms; one or more gas flow controllers as needed, which may be operated by manual (user) input, or may be semi-automated or fully automated by electronic or computerized control; and/or electronic hardware, firmware and/or software modules as schematically represented by the system controller 168 in FIG. 1. Manual input may entail physically manipulating a valve or other device. Manual input may alternatively or additionally entail pushing a button, operating a switch, or entering information on a control panel that communicates with or is associated with the system controller 168, in response to which the electronic processor 176 or other component of the system controller 168 transmits a control signal to an appropriate component of the means for operating in the analytical mode.

In embodiments in which the MS system 100 is interfaced with the GC 230, the analytical mode may include operating the sample introduction device 238 to inject a sample and carrier gas into the column 246, thereby establishing a flow of the sample and carrier gas through the column 246. In this case, the sample (or sample/carrier gas) flow path is defined in part by the column 246. Different components of the sample are separated by the stationary phase of the column 246 according to known chromatographic retention principles, and the resulting mixture of separated analyte fractions and carrier gas is flowed through the column 246, through the sample interface 112, and into the ionization chamber 136. The sample is then processed in the MS system 100 in the manner described above. Accordingly, in these embodiments the means for operating in the analytical mode may include one or more of the following components: the sample introduction device 238, the carrier gas source 242; the carrier gas line 264; and/or the column 246.

The MS system 100 also includes means (or apparatus) for operating the MS system 100 in a conditioning mode. In the conditioning mode, the MS system 100 is operated to flow a conditioning gas into the mass spectrometer 104 via one or more conditioning gas flow paths described above. In some embodiments, the means for operating in the conditioning mode may be configured for establishing a conditioning gas flow path from the conditioning gas source 204 and/or 212, through the conditioning gas line 208, 216, 220 and/or 224, and into the mass spectrometer 104. Accordingly, the means for operating in the conditioning mode may include one or more of the following components: the conditioning gas system 108, the conditioning gas source 204 and/or 212; the conditioning gas line 208, 216, 220 and/or 224, and any other gas conduits as needed to route the conditioning gas to one or more desired locations of the mass spectrometer 104; one or more gas flow controllers (e.g., 156) as needed, which may be manually operated, semi-automated or fully automated as described above; and/or electronic hardware, firmware and/or software modules as schematically represented by the system controller 168 in FIG. 1. In embodiments in which the MS system 100 is interfaced with the GC 230, the means for operating in the conditioning mode may include alternative or additional conditioning gas sources 282 and/or 290, associated conditioning gas lines 284 and/or 292 and any other gas conduits as needed; and/or other flow controllers (e.g., 268, 304). The means for operating in the conditioning mode may also include one or more auxiliary gas sources 308 and associated auxiliary gas lines 310 as described above.

In some embodiments, the effectiveness of the conditioning gas may be optimized by adding thermal energy to the conditioning gas and/or controlling its temperature. Accordingly, depending the conditioning gas flow path through the MS system 100, the means for operating in the conditioning mode may also be configured for controlling one or more of the following temperatures: the temperature of the column 246 and/or an interior of the GC housing 234 (e.g., an oven); the temperature of the sample interface 112; the temperature of the ionization chamber 136; the temperature of the mass analyzer 124; and/or the temperature of the ion detector 128. Temperature control may thus be accomplished by operating the heating device 250 and/or the heating system 164, which may be controlled by the system controller 168 and may follow a programmed temperature profile. In one example, the means for operating in the conditioning mode is configured for maintaining the ionization chamber 136 at a temperature up to the failure limits of the metal surfaces of the ionization chamber 136. In another example, the means for operating in the conditioning mode is configured for maintaining the ionization chamber 136 at a temperature ranging from −20° C. to 800° C.

In some embodiments, the effectiveness of the conditioning gas may be optimized by adding energy to the conditioning gas to excite (or energize) the conditioning gas molecules to an energetic state (e.g., a Rydberg or metastable state) or to ionize the conditioning gas molecules. The ionization device 140 may, for example, be operated for this purpose to produce electrons that interact with the conditioning gas molecules.

The means for operating the MS system 100 in the conditioning mode may be configured for regulating respective flows (e.g., flow rates) of the carrier gas and the conditioning gas into the column inlet 252 or into the mass spectrometer 104). The proportion of the carrier gas relative to the conditioning gas flowing into the column inlet 252 may range from 0% to less than 100%. Alternatively or additionally, the means for operating the MS system 100 in the conditioning mode may be configured for regulating respective flows of the auxiliary gas and the conditioning gas. The proportion of the auxiliary gas relative to the conditioning gas flowing through a particular gas line may range from 0% to less than 100%. The means for operating the MS system 100 in the conditioning mode may configured for determining whether the MS system 100 should be operated in the conditioning mode, or for regulating respective flows of the conditioning gas and the carrier gas into the mass spectrometer 104, based on comparing a chromatogram produced from the ion detector 128 from an analysis of a sample with a chromatogram produced from the gas detector 272 from the same analysis.

The means for operating the MS system 100 in the conditioning mode may be configured for off-line operation, on-line operation, or both. In off-line embodiments, the means for operating in the conditioning mode may include means (or apparatus) for switching the MS system 100 between the analytical mode and the conditioning mode. The means for switching may include one or more gas flow controllers and/or the system controller 168 as described above.

The means for operating in the off-line conditioning mode may be configured for evaluating one or more parameters of the MS system 100 and, based on the value of the parameter, determining whether the MS system 100 should be operated in the conditioning mode (or, equivalently, should be switched from the analytical mode to the conditioning mode). Examples of parameters that may be evaluated include, but are not limited to, the number of times the MS system 100 or a component thereof (e.g., mass spectrometer 104, ion source 120, column 246) has been operated in the analytical mode prior to evaluating the parameter (or since the last time the parameter was evaluated, or since the last time the conditioning mode was implemented); the amount of time that has elapsed prior to evaluating the parameter (or since the parameter was last evaluated, or since the conditioning mode was last implemented); a quality of a chromatogram (or mass spectrum) produced by the MS system under predetermined operating conditions; a measurement of an abundance of ions of one or more selected mass-to-charge ratios taken while operating in the analytical mode or conditioning mode; and/or the presence of stationary phase material separated from a stationary phase support of the column (i.e., evidence of column bleed). The quality of the chromatogram may include any metric (e.g., signal-to-noise ratio) indicative of a degradation in signal response or other performance criterion of the MS system 100. Parameters such as the quality of the chromatogram and abundance of contaminant ions may be compared to reference parameters stored in the database 180 of the system controller 168 to assist in the determination as to whether the conditioning mode should be run. Measurements of the abundance of selected ions may be done while operating in the conditioning mode to enable adjustment of certain operating parameters of the conditioning mode, such as the level of conditioning gas being added. The evaluation of one or more parameters of the MS system 100 for the purpose of determining whether to operate in the conditioning mode may be performed or managed by the performance evaluation software 188 of the system controller 168.

Alternatively or additionally, one or more of the above parameters may be evaluated manually by a user of the MS system 100. As examples, the user may keep track of the age and/or number of uses of one or more components of the MS system 100 that are known to improve or restore the performance of the MS system 100 after being subjected to the conditioning process. The user may make a visual inspection of a chromatogram or mass spectrum obtained from a sample analysis or a background analysis, and determine that the MS system 100 needs to be conditioned. Alternatively or additionally, the MS system 100 may be configured to enable the user to switch the MS system 100 to the conditioning mode at any desired time, or in accordance with a predetermined maintenance schedule.

If a determination is made that the MS system 100 should be operated in the conditioning mode, the means for operating in the off-line conditioning mode may be configured for taking an action based on (or in response to) that determination. As examples, the action may include switching the operation of the MS system 100 to the conditioning mode, scheduling a time for switching the operation of the MS system 100 to the conditioning mode, modifying a pre-scheduled time for switching the operation of the MS system 100 to the conditioning mode, and/or producing a user-readable indication that the MS system 100 should be operated in the conditioning mode. A user-readable indication may include, for example, an audible or visual alarm, a visual indication or message displayed on a user control panel of the MS system 100 or on a display screen communicating with the MS system 100, an electronic mail message sent to a user, etc.

In on-line embodiments, the means for operating in the conditioning mode may include means (or apparatus) for regulating respective flows of the carrier gas and the conditioning gas into the mass spectrometer 104 while the MS system 100 is actively performing a sample analysis. The means for regulating may include one or more gas flow controllers and/or the system controller 168 as described above. The means for regulating may be configured for regulating the respective flows such that the proportion of the conditioning gas flowing into the mass spectrometer ranges from greater than 0% to less than 100% by volume. In another example, the proportion of the conditioning gas ranges from 0.02% to 50%. In another example, the proportion of the conditioning gas ranges from 0.05% to 40%. In another example, the proportion of the conditioning gas ranges from 0.25% to 10%. As previously notes, these ranges may also apply to the off-line mode. The means for regulating may be configured for maintaining the flow of the conditioning gas at a constant flow rate while the temperature of the column 246 is being varied directly or indirectly by the heating device 250. For example, the system controller 268 may monitor the temperature and cause one or more flow controllers to adjust gas flow rate as needed.

Like the means for operating in the off-line conditioning mode described above, the means for regulating respective flows of the carrier gas and the conditioning gas into the mass spectrometer 104 while in the on-line mode may be based on evaluating one or more parameters of the MS system 100. In addition to the parameters described above, other examples of parameters that may be evaluated include, but are not limited to, a measurement of an abundance of ions of one or more selected mass-to-charge ratios taken while the MS system 100 is being operated to make a sample analysis; the composition of a sample matrix flowing or to be flowed through the column 246; the composition of a stationary phase supported in the column 246; an inside diameter of the column 246; and/or the reactivity of one or more components of the sample matrix with the conditioning gas. As noted above, the evaluation of the parameter(s) may be assisted by the performance evaluation software 188 and/or the use of data stored in the database 180 of the system controller 168.

Figure 2:
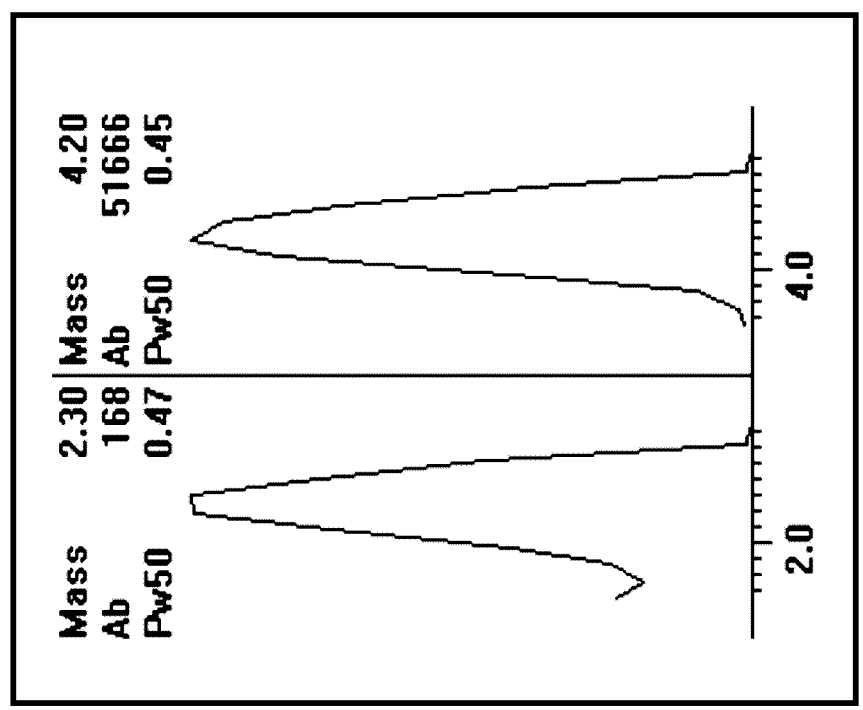
FIG. 2 illustrates a mass spectral measurement of a conditioning gas and a carrier gas through an MS system, the ratio of abundances of which may be utilized to determine the amount of conditioning gas to be provided to the MS system in accordance with the present disclosure.

One of the challenges associated with adding a conditioning gas to the MS system 100 is knowing how the conditioning gas is being added relative to the carrier gas. This is especially true when implementing lower gas flows (e.g., 0.005 mL/min). In some embodiments, the relative amount of added conditioning gas may be chosen based on the rate at which contaminant(s) is being introduced into the ion source 120. In general, larger amounts of conditioning gas are added for higher amounts of contaminant(s). For various experiments, particularly routine experiments, it is desirable to be able to set the level of conditioning gas consistently. In some embodiments, the level of conditioning gas is set based on the ratio of the abundance of carrier gas to the abundance of conditioning gas. In some embodiments, the amounts (e.g., flow rates, pressures) of conditioning gas and carrier gas are electronically controlled by the MS system 100, such as by the system controller 168 illustrated in FIG. 1. In such embodiments, the level of conditioning gas may be set automatically as part of an auto-tuning function of the MS system 100. FIG. 2 illustrates a mass spectral measurement of a conditioning gas (in this example, hydrogen, m/z=2) and a carrier gas (in this example, helium, m/z=4) being run through an MS system 100. Specifically, the measurement of FIG. 2 was obtained from the experiment described in Example 7 below. Accordingly, the means for regulating respective flows of the carrier gas and the conditioning gas into the mass spectrometer 104 may be configured for regulating based on a desired ratio of the abundance of conditioning gas ions to the abundance of carrier gas ions as measured by operating the ion source 120, the mass analyzer 124, and the ion detector 128. Moreover, the means for regulating the respective flows may be configured for comparing a measured ratio of the abundance of conditioning gas ions to the abundance of carrier gas ions with the desired ratio to determine whether a ratio difference between measured ratio and the desired ratio falls outside a desired range, and adjusting the flow of the conditioning gas relative to the carrier gas into the mass spectrometer 104 to maintain the ratio difference within the desired range. Desired ratios, for example, may be correlated to certain experiments, and/or different stages of a given experiment, and provided in look-up tables stored in the database 180 and accessible by hardware, firmware and/or software components of the system controller 168.

In some embodiments, such as in EXAMPLE 8 below, a conditioning gas such as hydrogen is utilized as the carrier gas for transporting the sample through the column 246, and an auxiliary gas such as helium is added to the hydrogen or other carrier gas either upstream of or at the mass spectrometer 104. The conditioning gas system 108 or other means or device may be utilized to regulate the flow of the auxiliary gas into the mass spectrometer 104 relative to the flow of the conditioning gas into the ionization chamber 136. Many of the above-described evaluation tasks may be performed in these embodiments. The mass spectrometer 104 may be operated to measure a ratio of the abundance of carrier gas ions to the abundance of auxiliary gas ions, and the flow of the auxiliary gas relative to the flow of the conditioning gas may be regulated based on the measured ratio.

Example 1

Off-Line Conditioning

Figure 3A:
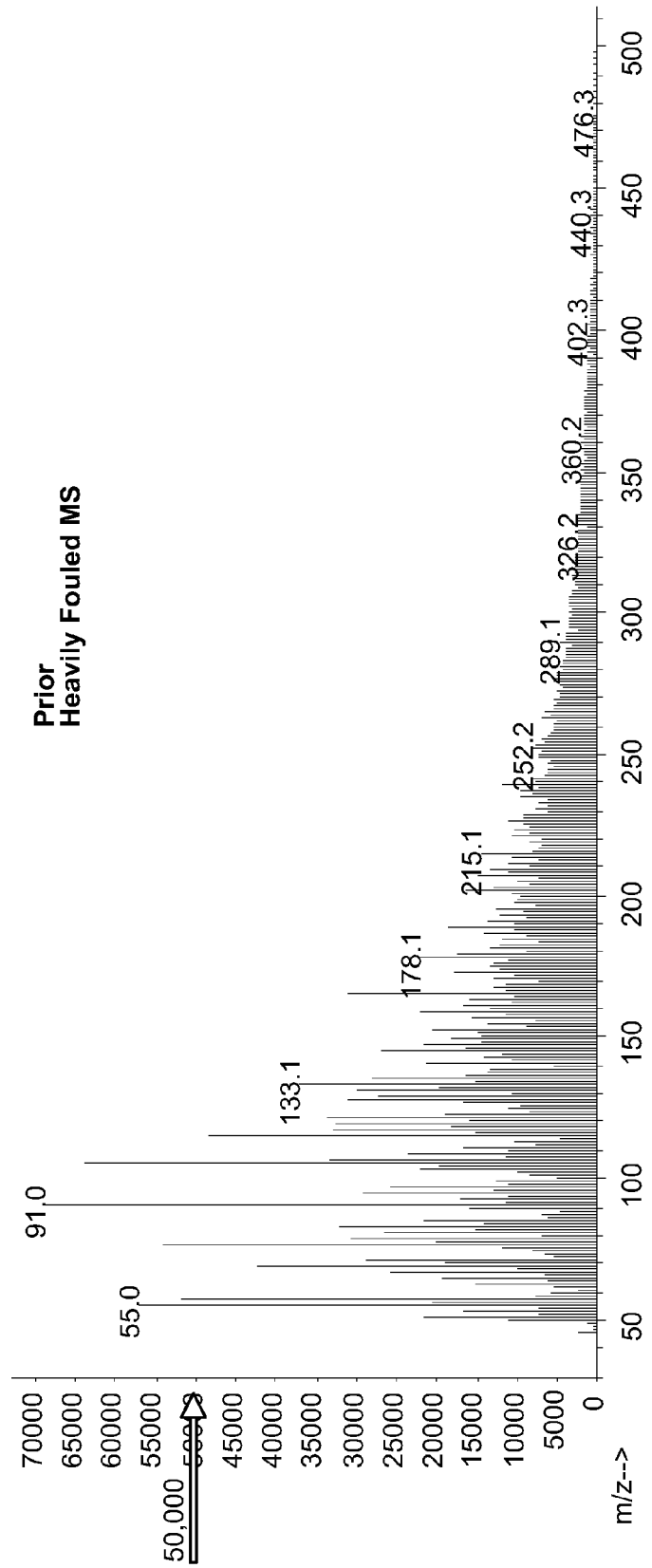
FIG. 3A illustrates a mass spectrum indicative of heavy fouling of an MS system.
Figure 3B:
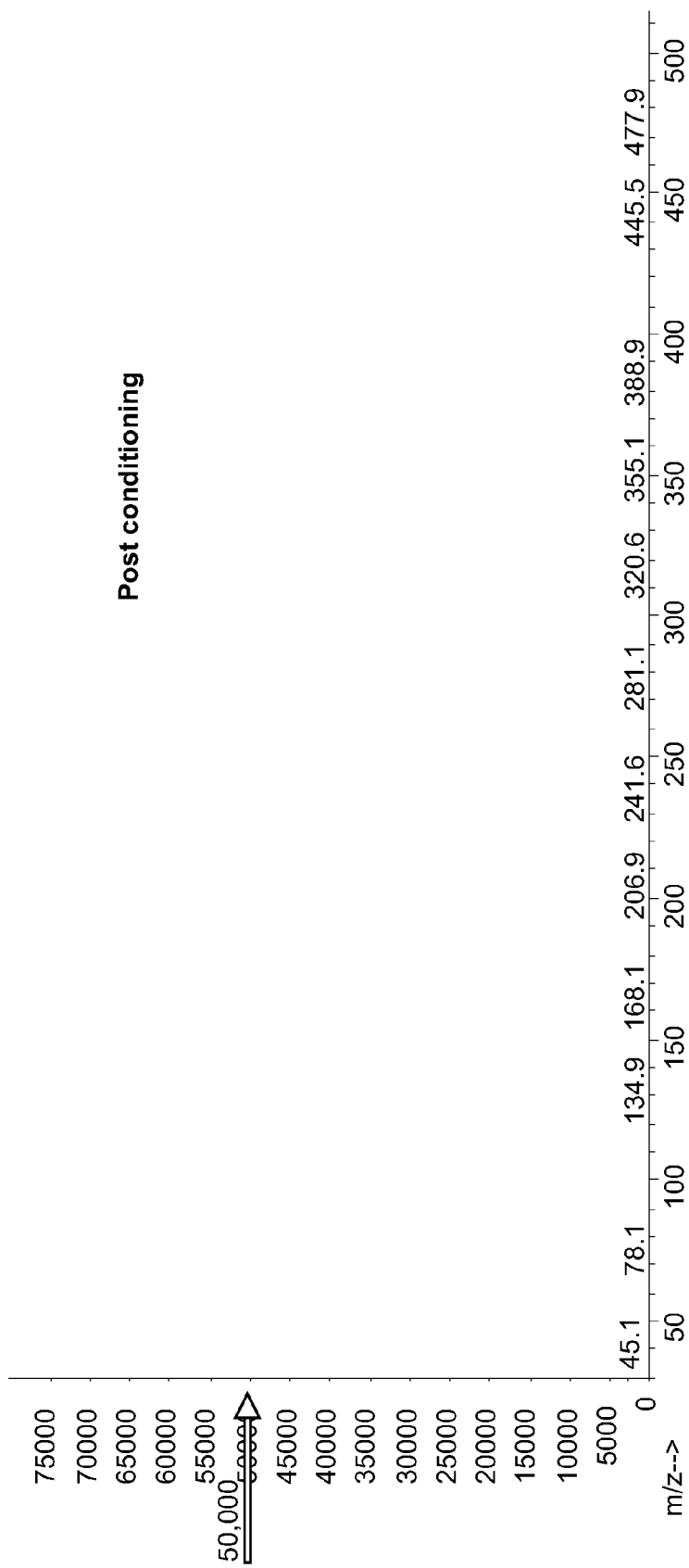
FIG. 3B illustrates a mass spectrum generated from the same MS system as in FIG. 3A, but after subjecting the MS system to a conditioning process in accordance with the present disclosure.
Figure 3C:
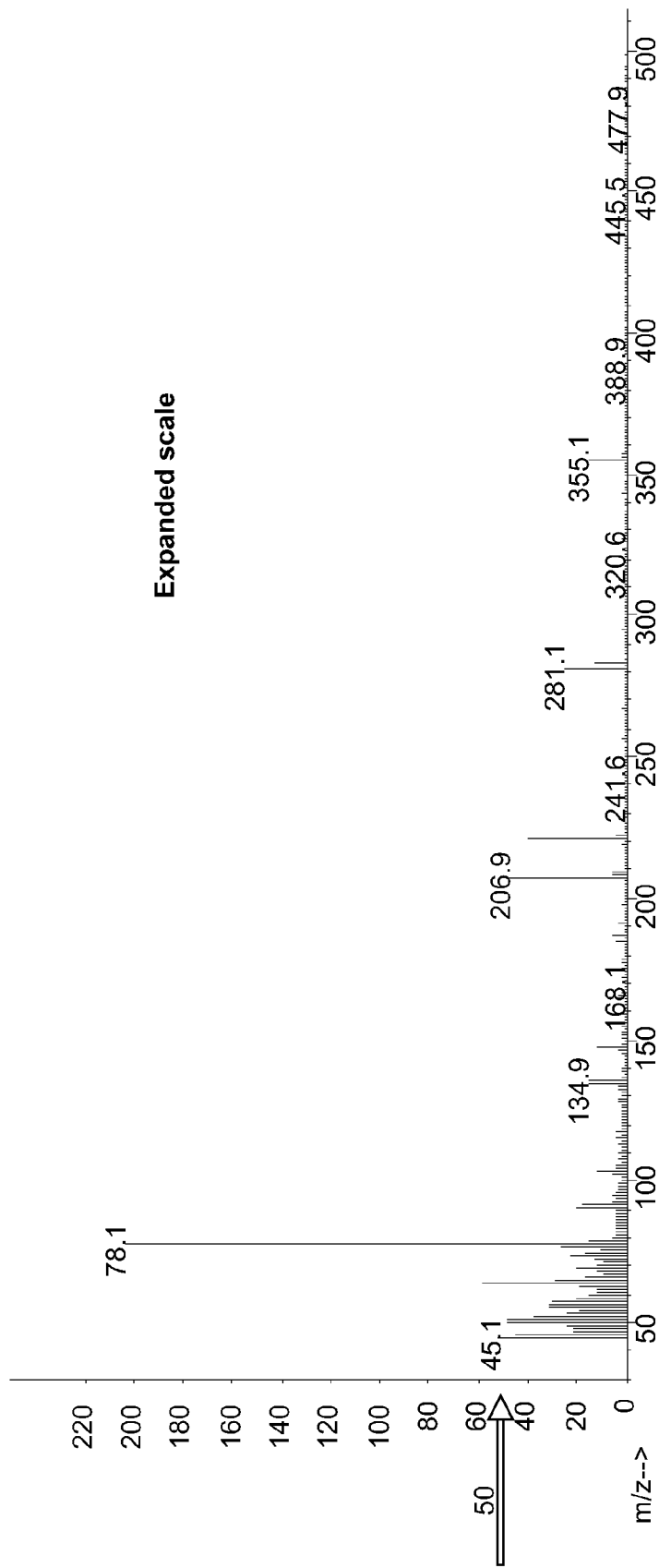
FIG. 3C illustrates the same mass spectrum as FIG. 3B, but on an expanded scale.

In this Example, a heavily-fouled MS system 100 consistent with that shown in FIG. 1, and with a GC 230 connected thereto, was subjected to an off-line conditioning process. Hydrogen was selected as the conditioning gas. A stream of hydrogen was introduced through the port of the sample interface 112 normally utilized for CI reagent gas and thereby conducted into the ionization chamber 136 and quadrupole of the mass spectrometer 104. The flow rate of the added hydrogen was 0.1 mL/min. The temperature of the ion source was 350° C., and the temperature of the quadrupole was 200° C. Hydrogen flow took place for sixteen hours, with the filament in continuous operation at 150 µA. Prior to conditioning the MS system 100 was run with the mass spectrometer 104 active, but without a sample, to analyze the background species suspected as contaminating the MS system 100. FIG. 3A is the resulting mass spectrum. The ion masses shown as being abundant are those typically associated with non-analytical or background molecules. FIG. 3B is a background mass spectrum generated after conditioning. At the same scale as the spectrum of FIG. 3A, the background species (e.g., m/z=45.1, 78.1, 134.9, etc.) appear to have been eliminated. FIG. 3C is the same mass spectrum as FIG. 3B, but on an expanded scale. FIG. 3C demonstrates a significant reduction in the abundance of the background species.

Example 2

Off-Line Conditioning

Figure 4A:
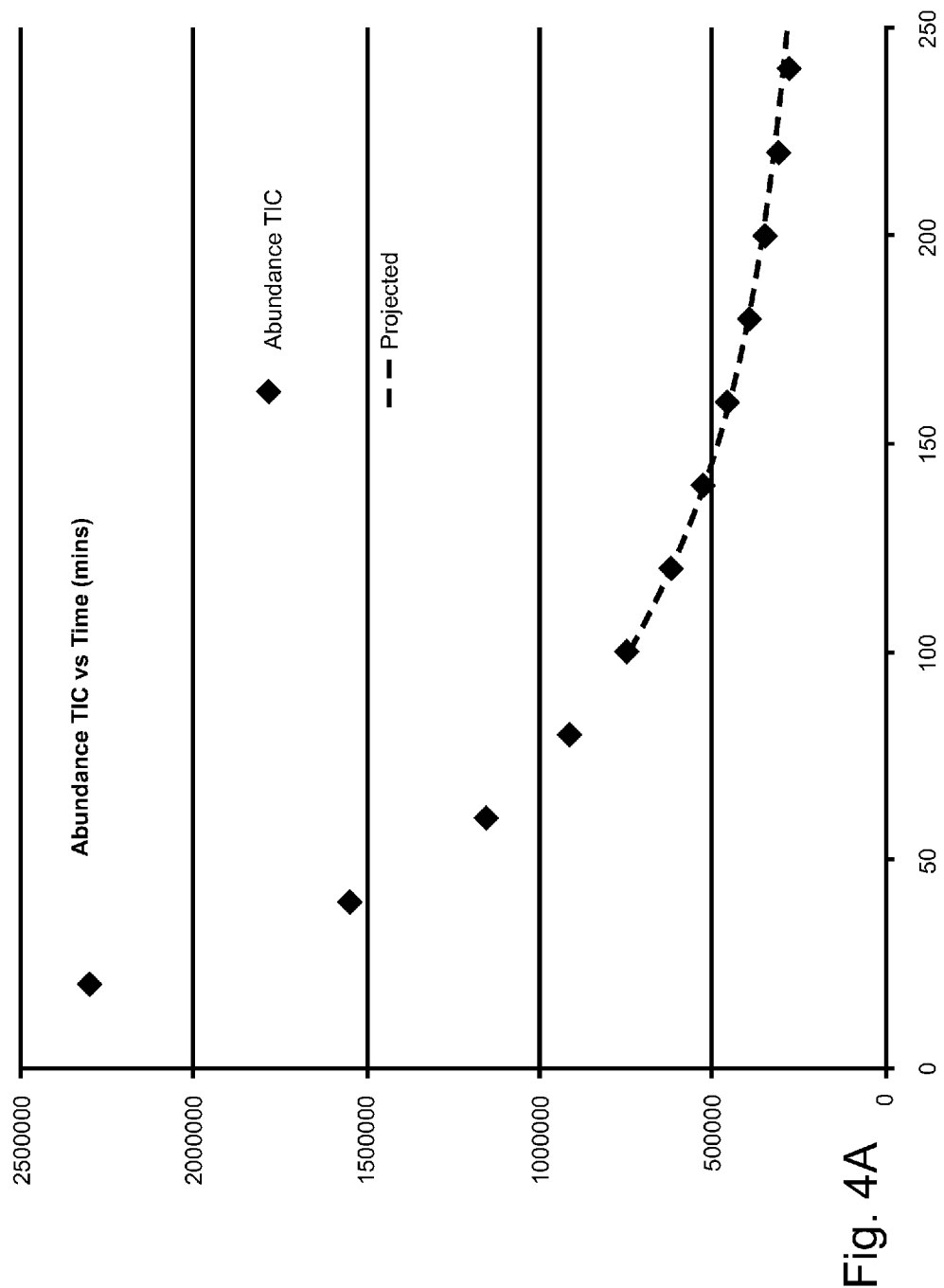
FIG. 4A is a Reconstructed Total Ion Chromatogram (RTIC, or TIC) as a function of time generated from running an MS system without any conditioning process.
Figure 4B:
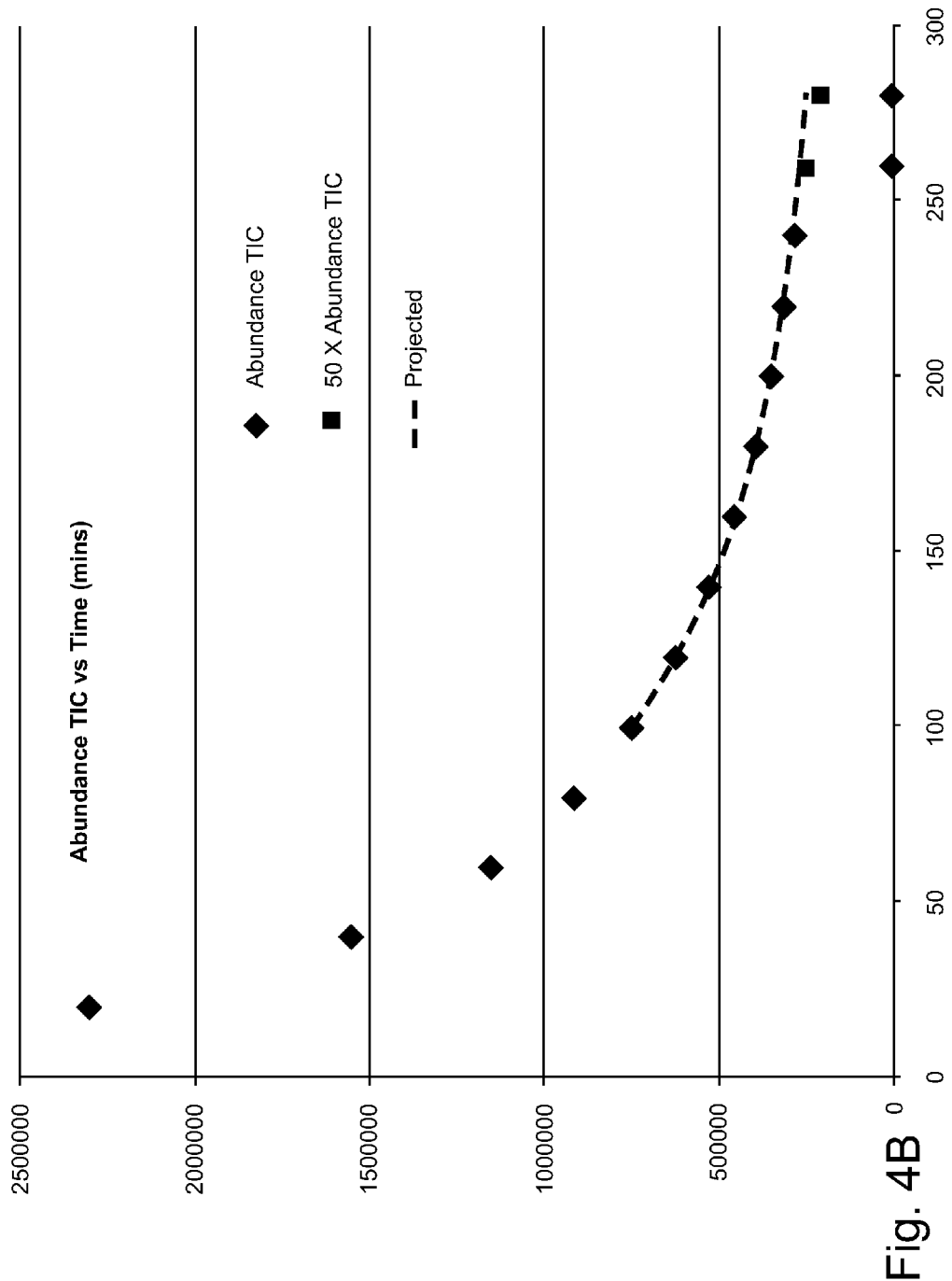
FIG. 4B is another RTIC of the same MS system as in FIG. 4A, but after 240 minutes the MS system was treated to an off-line conditioning process for two hours using hydrogen as the conditioning agent, in accordance with the present disclosure.
Figure 5A:
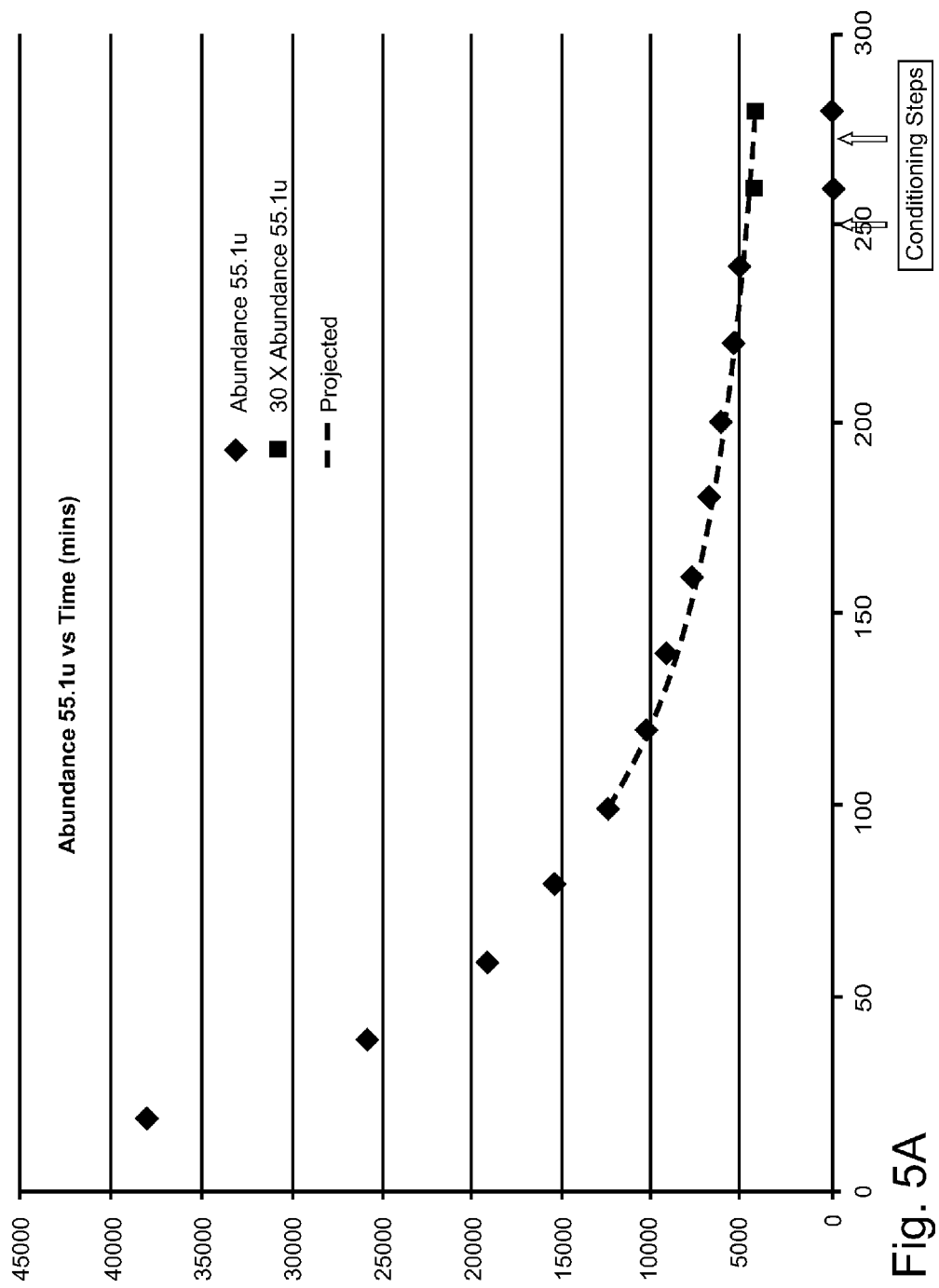
FIGS. 5A-5E are ion chromatograms as a function of time for the individual ion masses 55-$u$, 105-$u$, 91-$u$, 215-$u$ and 207-$u$, respectively; the chromatograms were generated from running an MS system and treating the MS system to the conditioning process after about 250 and 270 minutes.
Figure 5B:
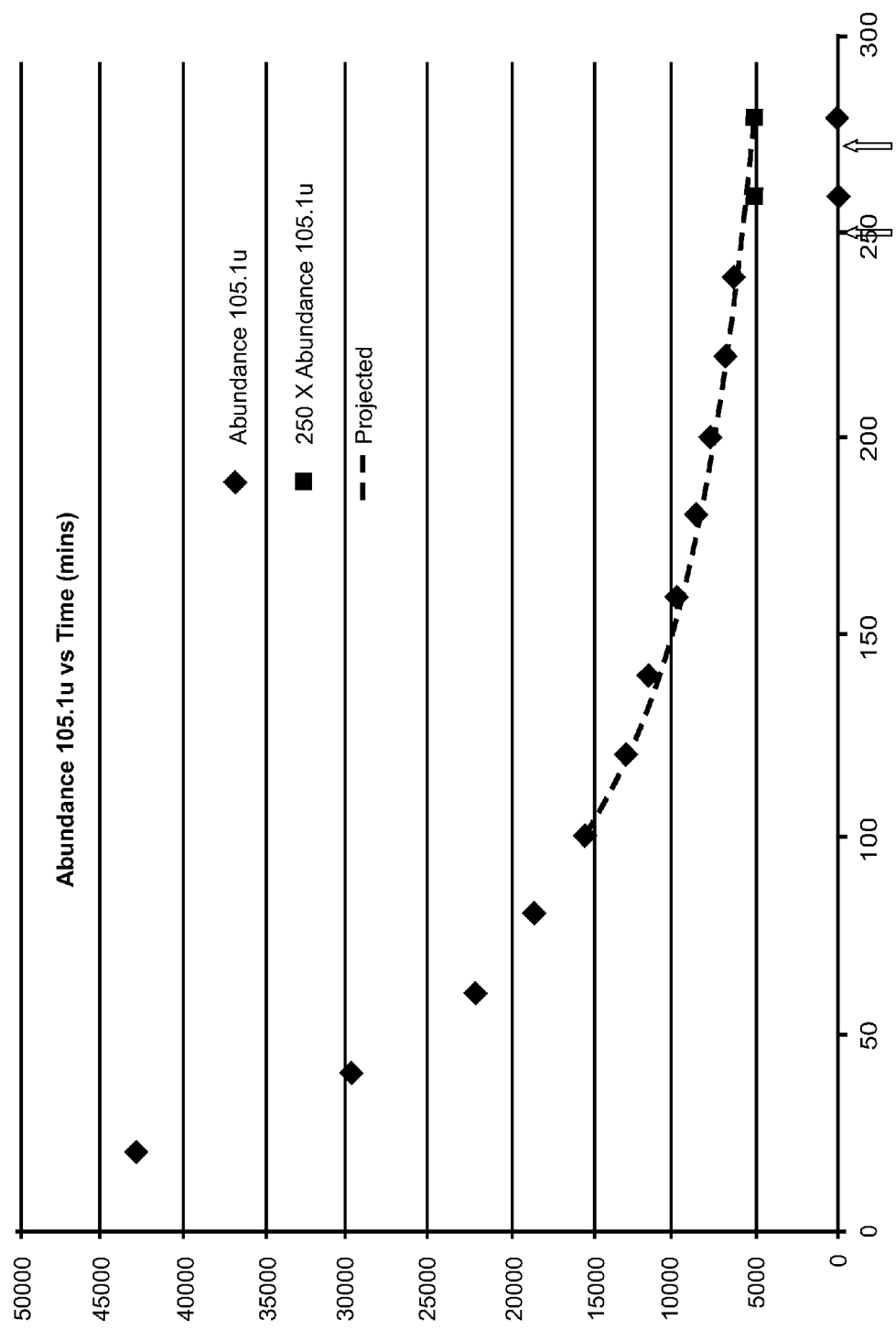
Figure 5C:
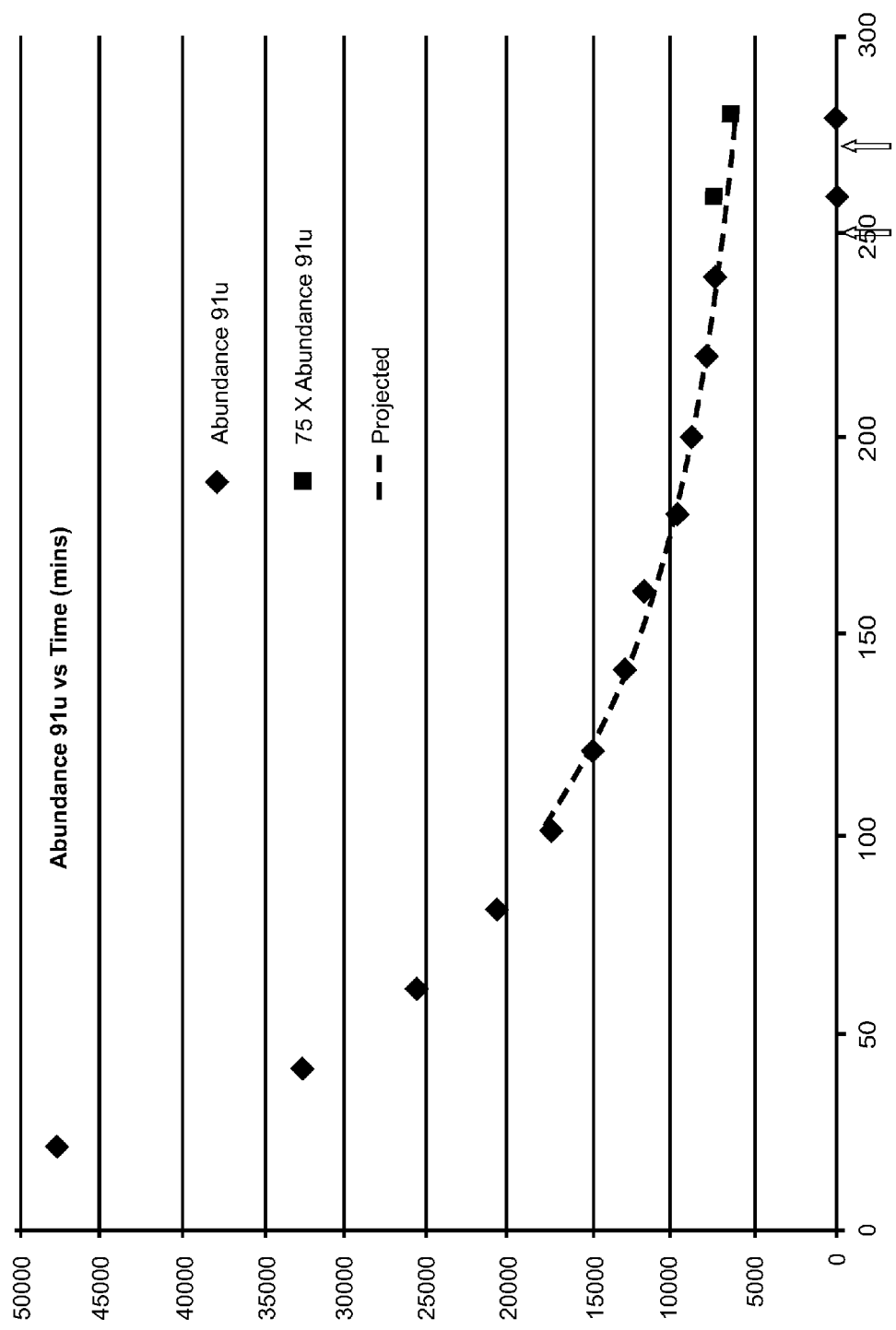
Figure 5D:
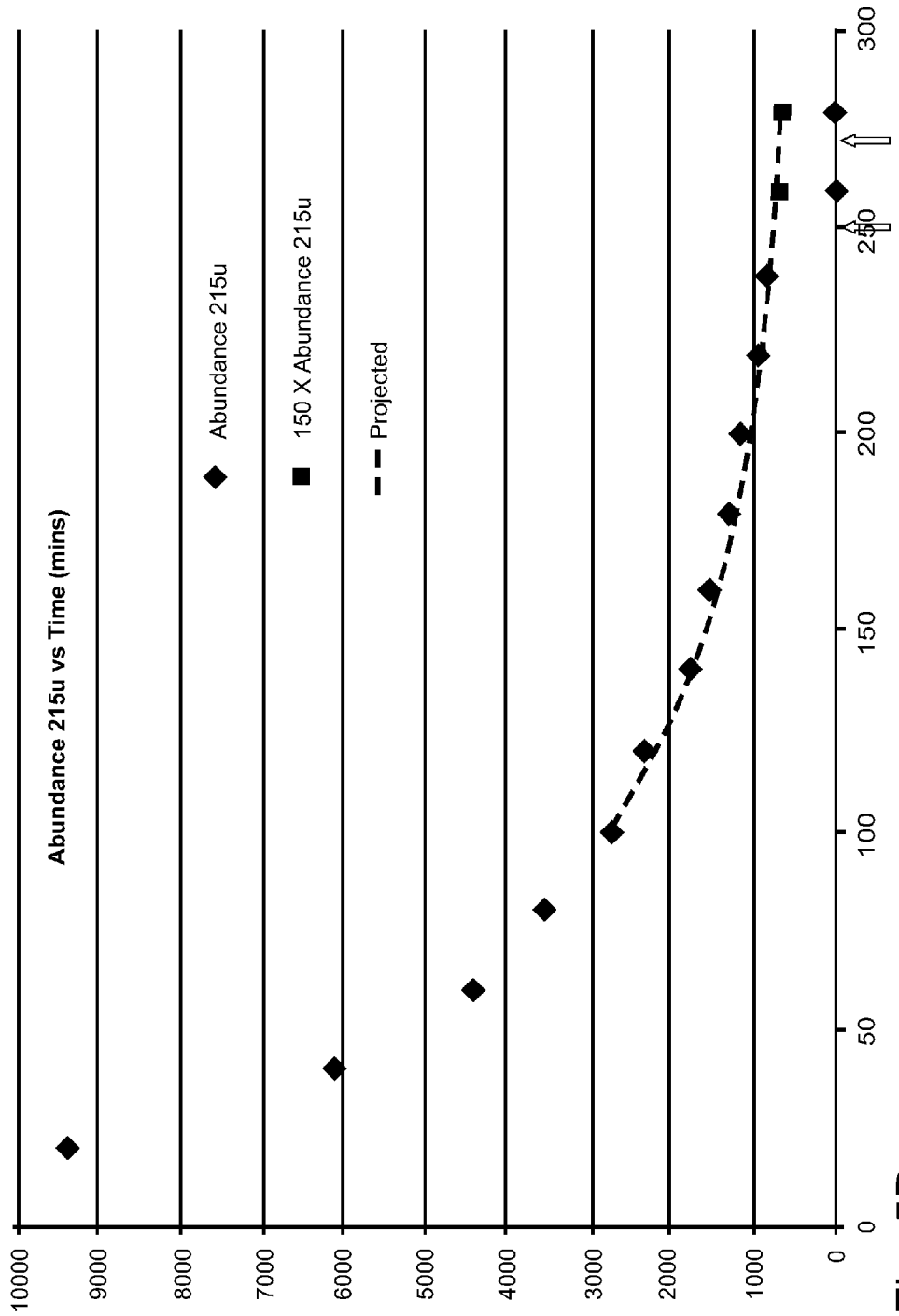
Figure 5E:
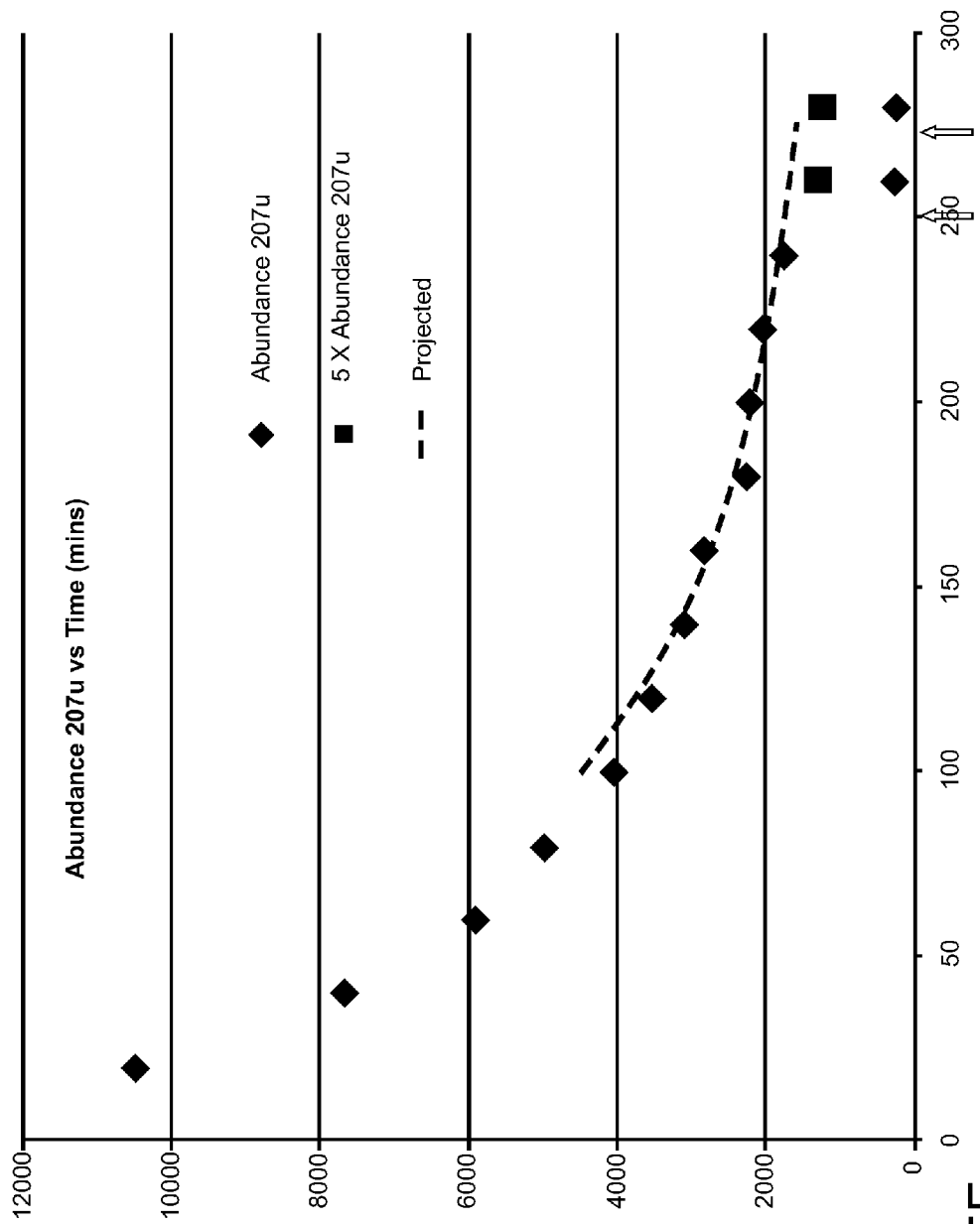

FIG. 4A is a Reconstructed Total Ion Chromatogram (RTIC, or TIC) as a function of time (minutes) generated from running an MS system 100 consistent with that illustrated in FIG. 1, without any conditioning process. FIG. 4A shows that without the conditioning process disclosed herein, continued use of the MS system 100 results in a slow improvement over a period of hours. As also shown in FIG. 4A, the system reaches an asymptotic state at which additional time of use leads to little improvement in background. FIG. 4B is another RTIC of the same MS system 100, but after 240 minutes the MS system 100 was treated to the off-line conditioning process for two hours using hydrogen as the conditioning agent. The background was then re-examined and found to have dropped by 50-fold over the projected RTIC value, as shown in FIG. 4B. A subsequent conditioning process at 270 minutes provided a slight improvement, as also shown in FIG. 4B.

Example 3

Off-Line Conditioning

FIGS. 5A-5E are ion chromatograms as a function of time for the individual ion masses 55-*u* (from hydrocarbon substances in the MS system 100), 105-*u* (from aromatic components), 91-*u* (from aromatic components), 215-*u* (from heavier, sample matrix-related components), and 207-*u* (from the GC capillary column connected to the system), respectively. These chromatograms were generated from running an MS system 100 consistent with that illustrated in FIG. 1, and treating the MS system 100 to the conditioning process after about 250 and 270 minutes. FIGS. 5A-5E demonstrate that not all ions have the same origin or behavior under the conditioning process, such that monitoring and modification of the conditioning process in a given MS system 100 may be advisable. The smallest gains were achieved for the 207-*u* ion as this ion is constantly being renewed from the column, which suggests that the condition process should be carried out more frequently to remove this component.

Example 4

Off-Line Conditioning

Figure 6A:
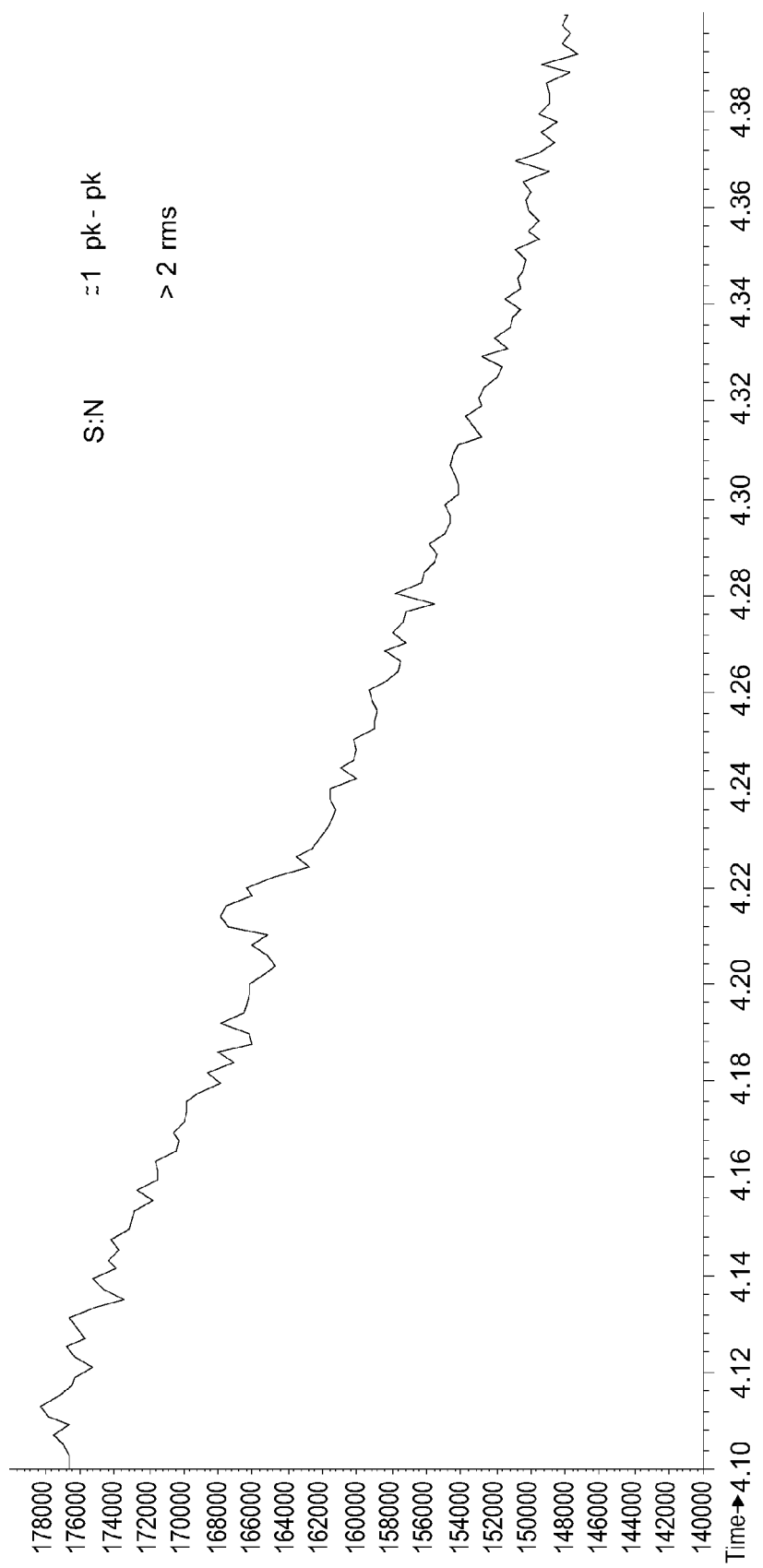
FIG. 6A is a reconstructed ion chromatogram for selected ion monitoring (SIM) acquisitions of octafluoronaphthalene in a contaminated MS system.
Figure 6B:
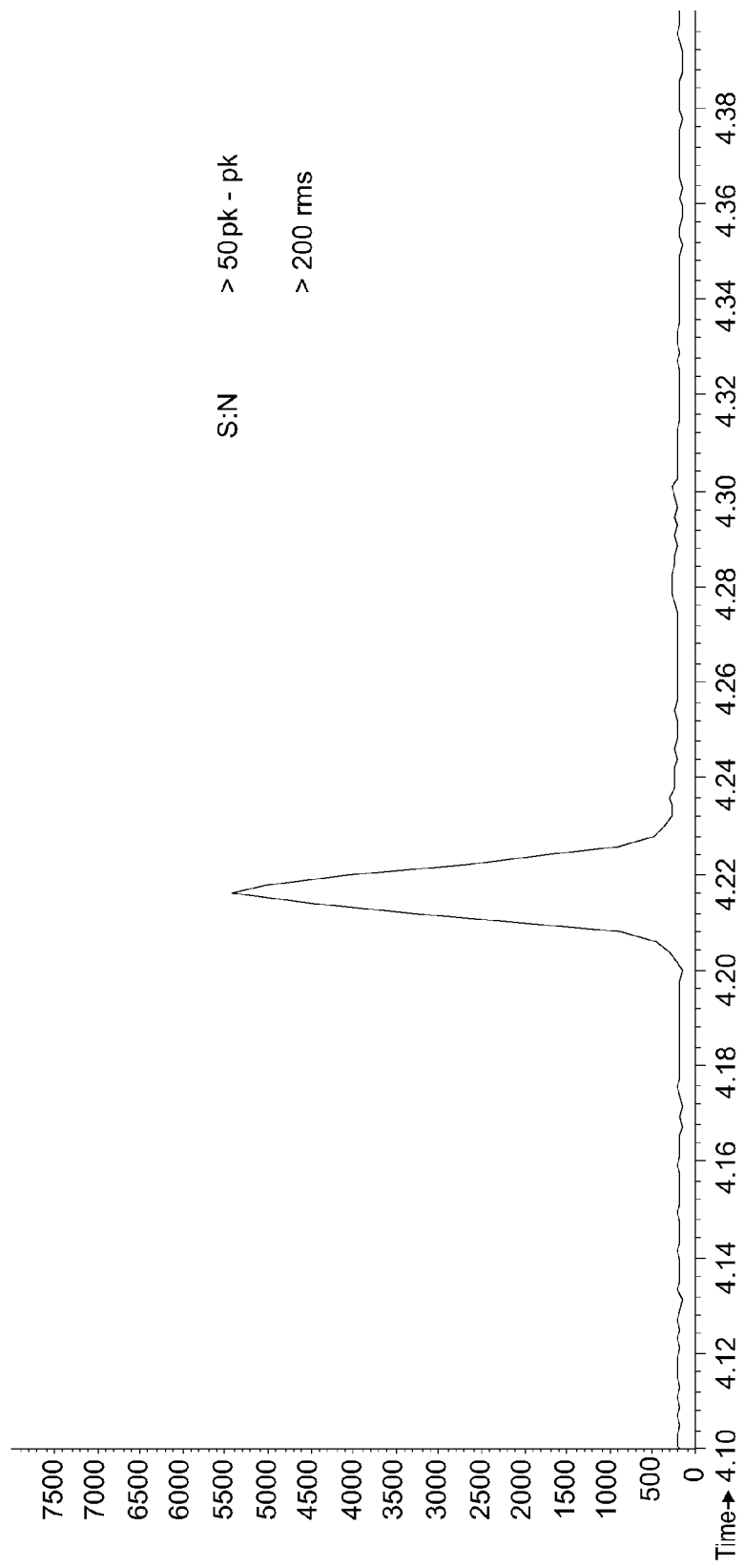
FIG. 6B is a reconstructed ion chromatogram for SIM acquisitions of octafluoronaphthalene in the same MS system as in FIG. 6A, but after the MS system was treated to an off-line conditioning process using hydrogen as the conditioning agent, in accordance with the present disclosure.

FIG. 6A is a reconstructed ion chromatogram for selected ion monitoring (SIM) acquisitions of octafluoronaphthalene in a contaminated MS system 100. The analyte is barely discernable as a "bump" near 4.216 minutes, and as indicated by the signal-to-noise (S/N) ratio. FIG. 6B is a reconstructed ion chromatogram for SIM acquisitions of octafluoronaphthalene in the same MS system 100 as in FIG. 6A, but after treatment to the off-line conditioning process using hydrogen as the conditioning agent. The background noise was significantly removed, leaving a clear peak without a tail, and a 50-fold increase in the S/N is indicated. FIGS. 6A and 6B demonstrate that application of the conditioning process can enhance the detection of an analyte by lowering the background around an ion of interest, or raising or restoring performance.

Example 5

On-Line Conditioning

This Example describes an analysis of a sample of three n-alkane hydrocarbons in isooctane to test the effect of the addition of hydrogen to the helium entering the mass spectrometer.

Figure 7:
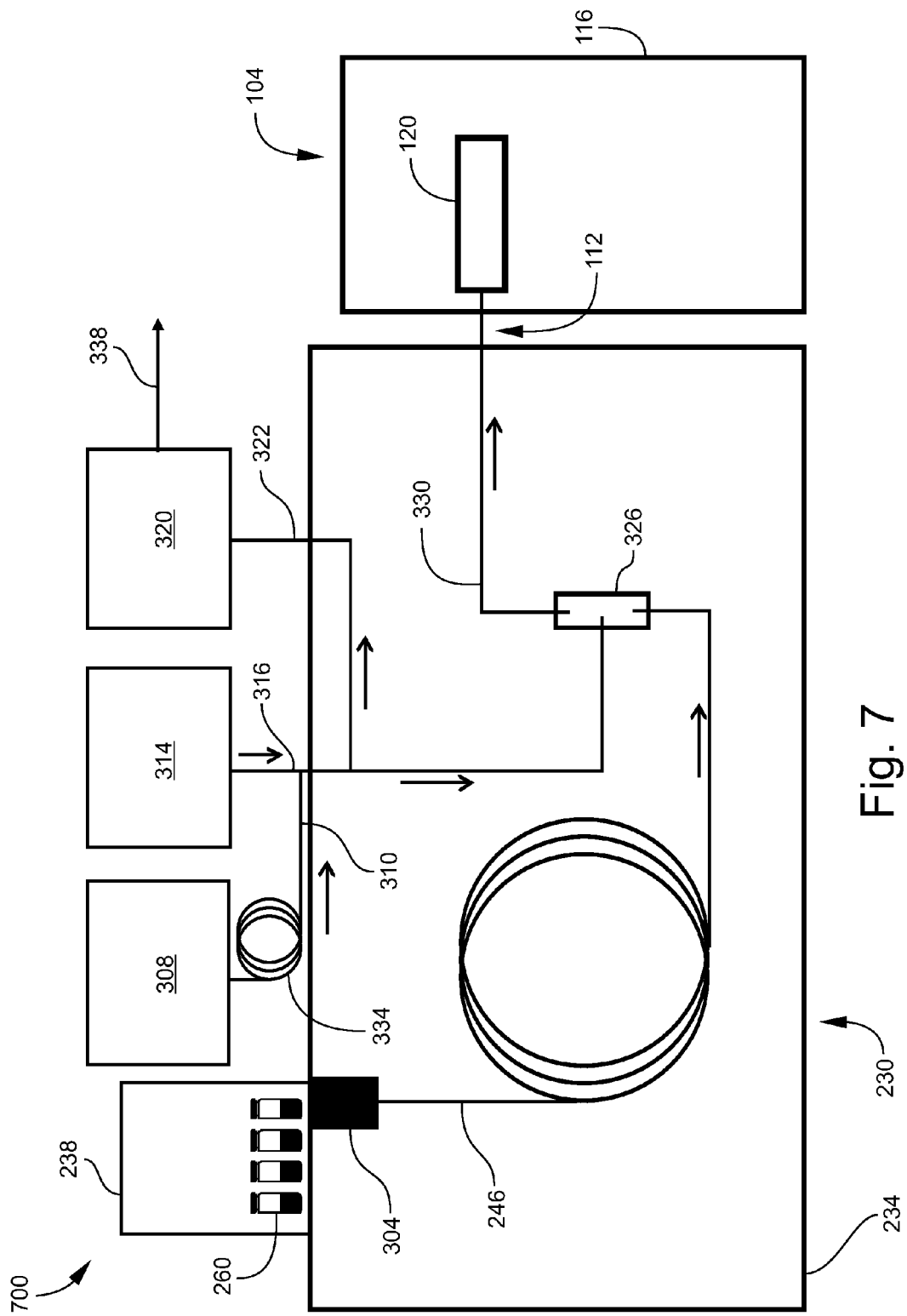
FIG. 7 is a schematic view of an example of an MS system configured for on-line conditioning in accordance with the present disclosure.

FIG. 7 is a schematic view of an example of an MS system 700 configured in particular for on-line conditioning and utilized in this Example. The MS system 700 includes many of the same components as the MS system 100 illustrated in FIG. 1, although for simplicity some of these components are not illustrated in FIG. 7. As between FIG. 1 and FIG. 7, similar components are designated by the same reference numerals. The MS system 700 illustrated in FIG. 7 includes a mass spectrometer 104 and a GC 230 connected thereto. The mass spectrometer 104 includes an ion source 120. The GC 230 includes a sample introduction device 238 equipped with a split/splitless inlet 304, and a column 246. The MS system 700 further includes a first flow controller 308 for the conditioning gas and an associated conditioning gas line 310, a second flow controller 314 for an auxiliary gas and an associated auxiliary gas line 316, and third flow controller 320 and an associated gas outlet line 322. The flow controllers 308, 314, 320 utilized in this Example were programmable EPCs. The conditioning gas line 310 is connected to the auxiliary gas line 316 at a point outside the GC housing 234 by any suitable plumbing structure such as a union (not shown). The gas outlet line 322 is connected to the auxiliary gas line 316 at a point inside the GC housing 234 by any suitable plumbing structure such as a union (not shown). The outlet of the column 246 is connected to a purged union 326. A gas transfer line 330 interconnects the purged union 326 and the ion source 120. The gas transfer line 330 may be considered as an extension of the column 246 or alternatively as a separate gas line.

In this Example, the carrier gas was helium, the conditioning gas was hydrogen, and the auxiliary gas was helium. The helium carrier gas was supplied to the inlet of the column 246 at a pressure of about 12.5 psi. The purged union 326 facilitated the addition of the stream of hydrogen and auxiliary helium to the sample/helium stream flowing from the column 246. The first flow controller 308 supplied hydrogen at 10.12 psi through a restrictor 334, after which the flow rate was 0.067 mL/min. The second flow controller 314 supplied helium at 3.76 psi at a flow rate of 8.9 mL/min to regulate the pressure in the purged union 326. The third flow controller 320 was plumbed backwards through a restrictor (not shown) into the mixed helium/hydrogen stream from the first and second flow controllers 308, 314 to vent part of the helium/hydrogen mixture (arrow 338) at a constant flow of 8.362 mL/min. The pressure of the helium/hydrogen mixture at the third flow controller 320 was 2.0 psi. During the chromatographic run, the helium stream from the column 246 flowed into the purged union 326 at a flow rate of 1.2 mL/min, and the inlet pressure of the helium carrier gas into the column 246 and the pressures in the first and second flow controllers 308, 314 were all programmed to maintain constant flow at the above-indicated levels throughout the temperature program.

With all flow controllers 308, 314, 320 turned on, the helium/hydrogen mixture flowed into the purged union 326 at flow rates of 0.6 mL/min (He) and 0.005 mL/min ($H_2$). The resulting helium/hydrogen mixture entered the ion source 120 at 1.805 mL/min. If the first flow controller 308 is turned off (i.e., without the 0.005-mL/min hydrogen being a part of the stream entering the ion source 120), then only the 1.8 mL/min of helium would enter the ion source 120. Thus, by the configuration illustrated in FIG. 7, samples can be easily run with or without implementing the conditioning process employed in this Example (i.e., turning the hydrogen flow on or off).

To test the effect of the addition of hydrogen to the helium entering the mass spectrometer 104, multiple analyses of a sample of three n-alkane hydrocarbons—specifically n-tetradecane ($n-C_{14}$), n-pentadecane ($n-C_{15}$), and n-hexadecane ($n-C_{16}$)—in isooctane, each at a concentration of 10 ng/µL, were performed both with and without the addition of the hydrogen. This sample was chosen because it is a high concentration of relatively non-polar compounds that exhibit very few if any activity problems.

TABLE 1 below lists the instrument parameters for this Example.

TABLE 1

| Instrument Parameters | | | |
|---|---|---|---|
| Ramp | ° C./min | ° C. | Hold min |
| Initial | | 90 | 0.5 |
| Ramp 1 | 20 | 325 | 2.75 |
| Runtime | 15 min | | |
| Postrun | 325° C./min for 3.5 min | | |
| Inlet | Split/Splitless | | |
| Temp | 280° C. | | |
| Mode | Pulsed Splitless, Constant Flow | | |
| Flow | 1.2 mL/min | | |
| Pulse Press | 25 psi | | |
| Pulse Time | 0.5 min | | |
| Purge Time | 0.5 min | | |
| Purge Flow | 50 mL/min | | |
| Column | DB-5MSUI part # (122-5512UI) 15 m x 0.25 mm id x 0.25 µm film | | |
| Outlet Pressure | Programmed for constant MSD restrictor flow (3.75 psig initial) | | |
| Injection volume | 1 µL | | |
| MSD | Agilent 5975C | | |
| Solvent Delay | 2 min | | |
| Acquisition Mode | SIM | | |
| SIM Ions | 71, 85, 207 | | |
| Dwell | 10 msec | | |
| TID | ON | | |
| Quad Temp | 180° C. | | |
| Source Temp | 230° C. | | |
| Transfer Line | 300° C. | | |
| Tune | Atune, Gain 1 | | |
| Backflush Device | Post-column Purged Union with overpressure vent | | |
| MSD restrictor | 1.0 m x 0.15 mm id inert fused silica tubing | | |
| Restrictor Flow | 1.8 mL/min Constant Flow | | |
| Backflush | 3.5 min, 325° C., 23.3 psig | | |
| $H_2$ Addition | Added to makeup | | |
| $H_2$ Restrictor | 3.0 m x 0.05 mm id fused silica tubing | | |
| $H_2$ Pressure | Programmed for constant flow of 5 µL/min $H_2$ into MSD | | |

Figure 8:
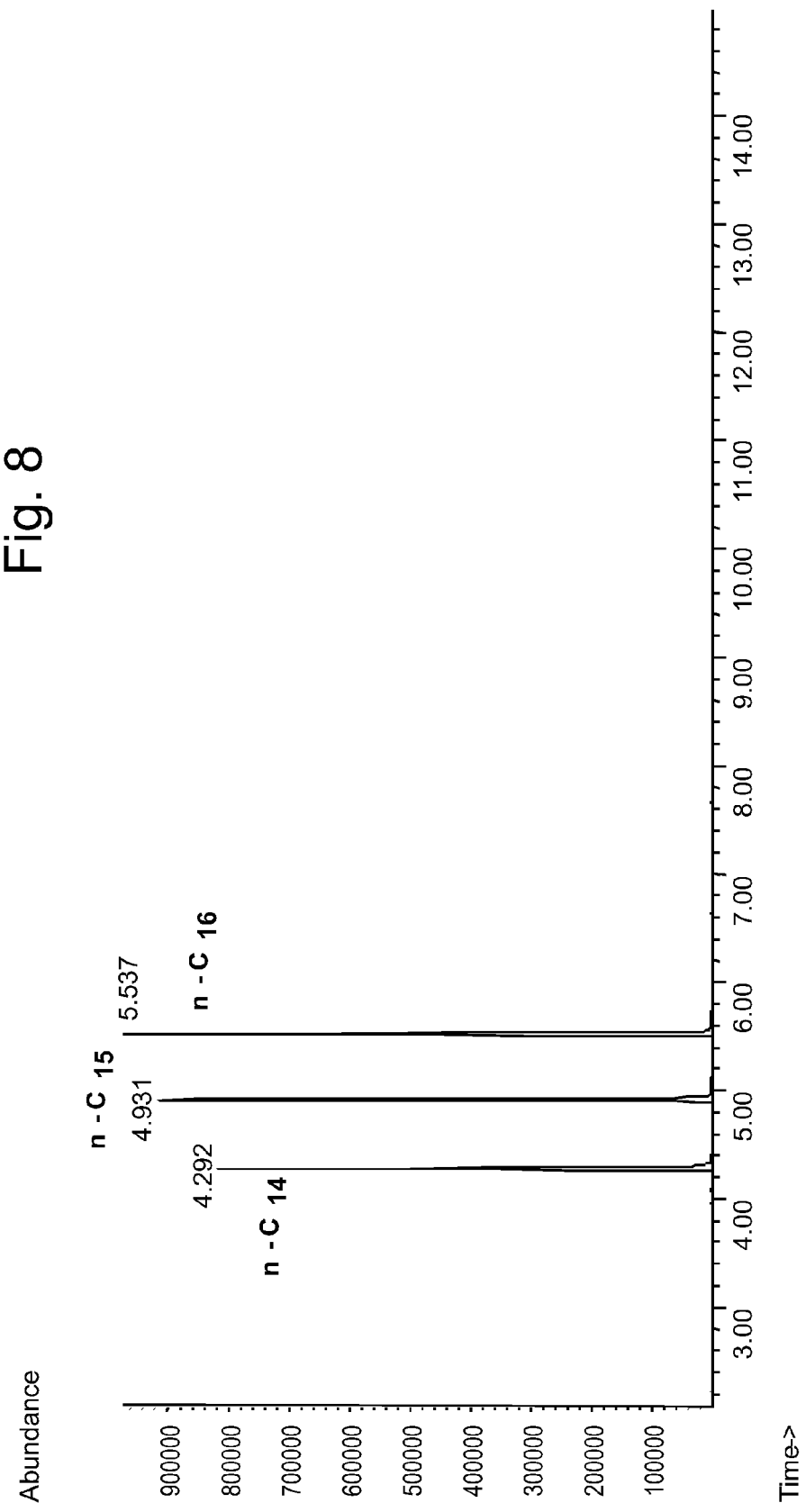
FIG. 8 is chromatogram obtained from an analysis of a sample of three n-alkane hydrocarbons, n-tetradecane (n-$C_{14}$), n-pentadecane (n-$C_{15}$) and n-hexadecane (n-$C_{16}$), run through the MS system illustrated in FIG. 7.

FIG. 8 is a TIC that was typical of this Example when hydrogen was added.

A series of twenty-two replicate runs of the sample were made with no hydrogen added as a control. Because the column 246 was programmed up to 325° C. and was a relatively new column, the source contamination from column bleed was expected to make the response of serial injections drop. This degradation in performance was in fact observed as shown in the response data provided in TABLE 2 below.

TABLE 2

Raw Integrator Areas for 22 Consecutive
Runs of the Sample with No Hydrogen Added

| run # | n-$C_{14}$ area | n-$C_{15}$ area | n-$C_{16}$ area |
|---|---|---|---|
| 1 | 6527940 | 6684730 | 67316710 |
| 2 | 6163040 | 6365260 | 6411940 |
| 3 | 6068450 | 6265900 | 6323490 |
| 4 | 5985550 | 6192020 | 6253440 |
| 5 | 5920670 | 6126290 | 6178460 |
| 6 | 5913440 | 6103720 | 6171680 |
| 7 | 5925520 | 6112470 | 6168160 |
| 8 | 5858280 | 6047730 | 6099580 |
| 9 | 5871950 | 6049400 | 6121840 |
| 10 | 5812020 | 5989770 | 6056490 |
| 11 | 5820170 | 6004660 | 6047150 |
| 12 | 5748320 | 5937110 | 6000790 |
| 13 | 5761850 | 5940150 | 6009640 |
| 14 | 5718320 | 5896430 | 5957680 |
| 15 | 5726420 | 5906800 | 5961500 |
| 16 | 5725410 | 5909500 | 5978280 |
| 17 | 5704120 | 5894010 | 5944330 |
| 18 | 5658460 | 5836330 | 5909420 |
| 19 | 5588440 | 5766990 | 5836070 |
| 20 | 5548320 | 5731290 | 5806550 |
| 21 | 5577990 | 5766070 | 5833330 |
| 22 | 5536550 | 5723560 | 5785420 |

Figure 9:
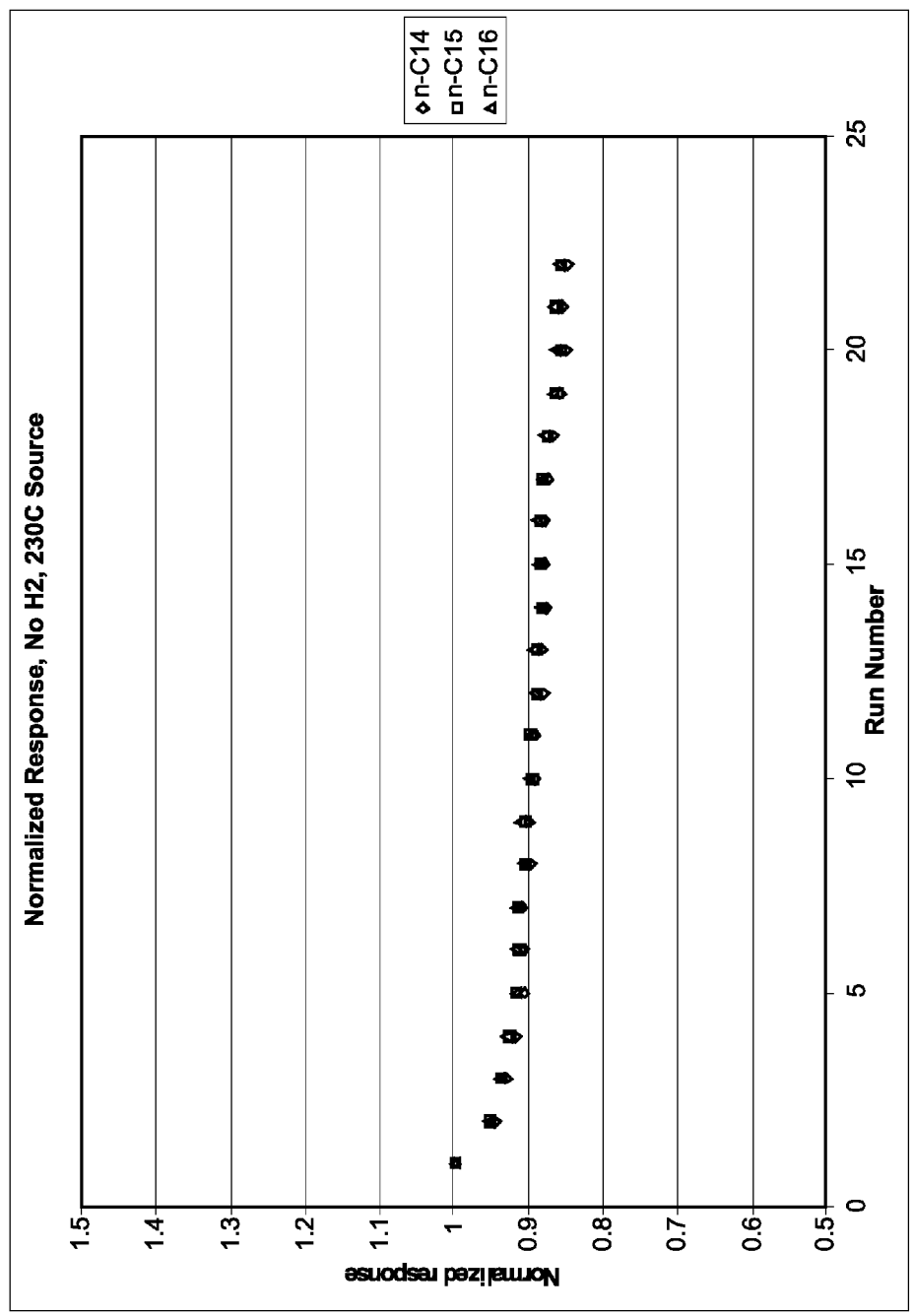
FIG. 9 is a plot of raw integrator areas for twenty-two consecutive runs of the sample of FIG. 8 without a conditioning gas being added, normalized to the first injection and plotted for the three compounds.

FIG. 9 is a plot of the data from TABLE 2, normalized to the first injection and plotted for the three compounds. FIG. 9 shows that the response falls 15% for all three compounds.

Figure 10:
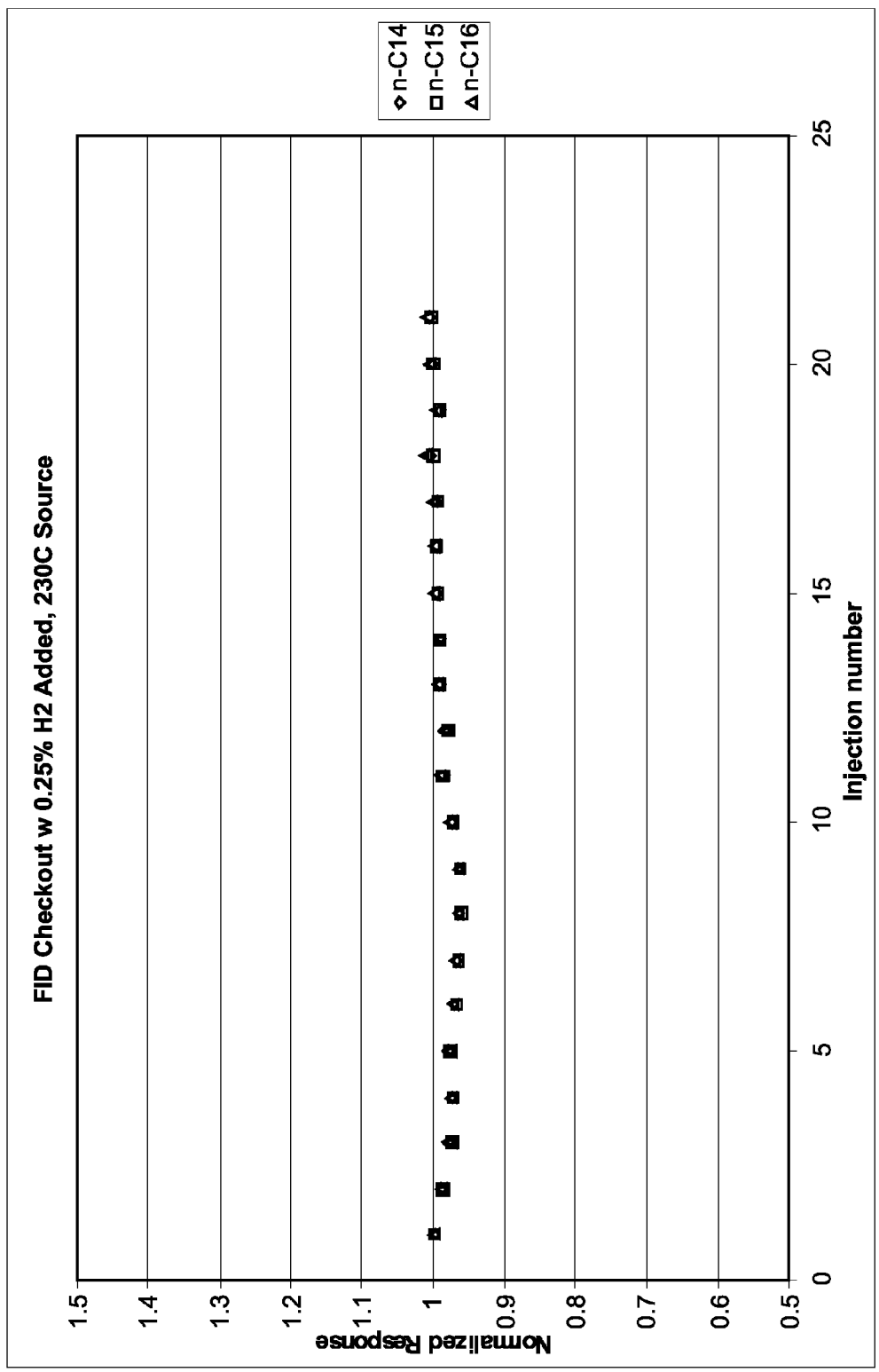
FIG. 10 is a plot of raw integrator areas for twenty-one consecutive runs of the sample of FIG. 8 with a conditioning gas being added, normalized to the first injection and plotted for the three compounds.

The series of analyses was repeated, but this time with the hydrogen added at 0.005 mL/min as described above. The response data is provided in TABLE 3 below. FIG. 10 is a plot of the data from TABLE 3, normalized to the first injection and plotted for the three compounds. TABLE 3 and FIG. 10 demonstrate that the response now remained constant for all three compounds, thus demonstrating that added hydrogen eliminated the degradation in the response.

TABLE 3

Raw Integrator Areas for 21 Consecutive Runs
of the Sample with 5 μL/min Hydrogen Added

| run # | n-$C_{14}$ area | n-$C_{15}$ area | n-$C_{16}$ area |
|---|---|---|---|
| 1 | 5650320 | 5795110 | 5814900 |
| 2 | 5590770 | 5714370 | 5751740 |
| 3 | 5529930 | 5650690 | 5680710 |
| 4 | 5511490 | 5634980 | 5669660 |
| 5 | 5530050 | 5658120 | 5687170 |
| 6 | 5498250 | 5611980 | 5650740 |
| 7 | 5471190 | 5596170 | 5633590 |
| 8 | 5445580 | 5570350 | 5609500 |
| 9 | 5448140 | 5573710 | 5609970 |
| 10 | 5505020 | 5629310 | 5677190 |
| 11 | 5578850 | 5715670 | 5760110 |
| 12 | 5556950 | 5680140 | 5714160 |
| 13 | 5604790 | 5740080 | 5786420 |
| 14 | 5602550 | 5742070 | 5766270 |
| 15 | 5622990 | 5766140 | 5806920 |
| 16 | 5631060 | 5770860 | 5804230 |
| 17 | 5634590 | 5760410 | 5819640 |
| 18 | 5683250 | 5807250 | 5871830 |
| 19 | 5598700 | 5740670 | 5794060 |
| 20 | 5661630 | 5797440 | 5843810 |
| 21 | 5681120 | 5813190 | 5860870 |

Example 6

On-Line Conditioning

This Example described an analysis of a sample of semi-volatile pollutants. Some of these compounds are polar and exhibit activity problems.

Figure 11:
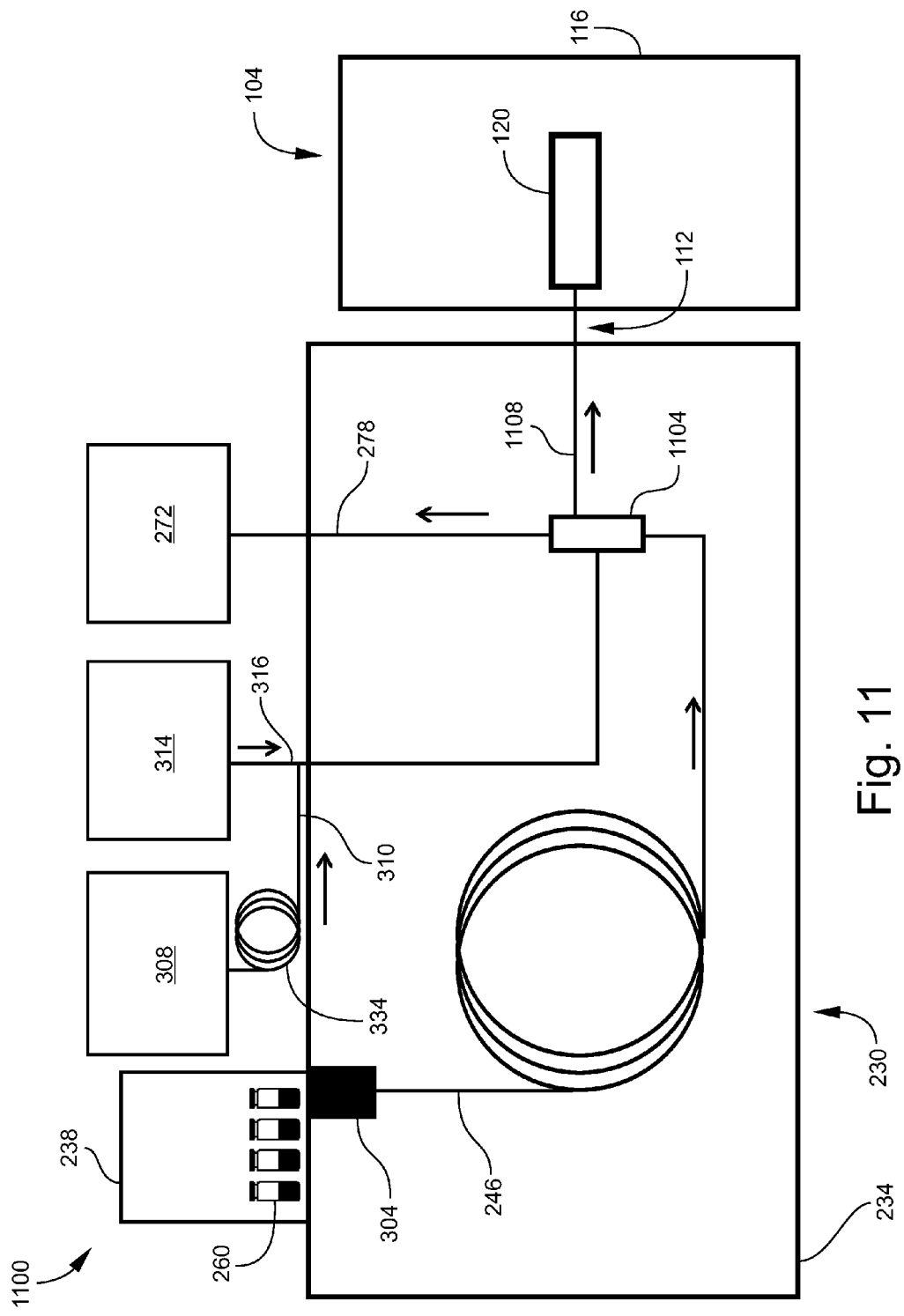
FIG. 11 is a schematic view of another example of an MS system configured for on-line conditioning in accordance with the present disclosure.

FIG. 11 is a schematic view of another example of an MS system 1100 configured in particular for on-line conditioning and utilized in this Example. The MS system 1100 includes many of the same components as the MS system 100 illustrated in FIG. 1, although for simplicity some of these components are not illustrated in FIG. 11. As compared with FIG. 1 and FIG. 7, similar components are designated in FIG. 11 by the same reference numerals. The MS system 1100 illustrated in FIG. 11 includes a first flow controller 308 for the conditioning gas and an associated conditioning gas line 310, and a second flow controller 314 for an auxiliary gas and an associated auxiliary gas line 316. The flow controllers 308, 314 utilized in this Example were programmable EPCs. The conditioning gas line 310 is connected to the auxiliary gas line 316 at a point outside the GC housing 234 by any suitable plumbing structure such as a union (not shown). In this Example, the analytes are at a very low concentration of 200 pg/μL. Because there can be chromatographic losses of some of the active compounds at low levels, the MS system 1100 utilized a deactivated post-column flow splitter 1104 and an FID 272 located outside the GC housing 234. Accordingly, the outlet of the column 246 is connected to the purged splitter 1104. A first gas outlet line 1108 interconnects the purged splitter 1104 and the ion source 120. The first gas outlet line 1108 may be considered as an extension of the column 246 or alternatively as a separate gas transfer line. A second gas outlet line 278 interconnects the purged splitter 1104 and the FID 272. The flow splitter 1104 divides the column effluent equally between the mass spectrometer 104 and the FID 272. The FID response is very stable and does not change with time. The FID 272 therefore makes an excellent reference for tracking response changes in the mass spectrometer 104, even for compounds with variable degrees of loss in the inlet.

In this Example, the carrier gas was helium, the conditioning gas was hydrogen, and the auxiliary gas was helium. The helium carrier gas was supplied to the inlet of the column 246 at a pressure of about 25 psi and flowed through the column 246 at a constant rate of 0.95 mL/min. The first flow controller 308 supplied hydrogen through a restrictor 334, after which the flow rate was 0.08 mL/min. The second flow controller 314 supplied helium as a make-up gas to the flow splitter 1104 at a constant pressure of 2 psig and at a flow rate of 3.05 mL/min. As a result, the helium flowed to the mass spectrometer 104 and the FID 272 each at 2 mL/min. Because the restrictors (not shown) from the flow splitter 1104 to the mass spectrometer 104 and FID 272 are in the oven (the heated GC housing 234) and the flow splitter 1104 is maintained at constant pressure by the second flow controller 314, the flow of helium to each of the mass spectrometer 104 and FID 272 dropped from 2 mL/min at the initial oven temperature of 40° C. to 0.67 mL/min at 320° C. The amount of hydrogen reaching the mass spectrometer 104, however, stayed constant at 0.04 mL/min. Thus, by the configuration illustrated in FIG. 11, samples can be easily run with or without implementing the conditioning process employed in this Example (i.e., turning the hydrogen flow on or off).

TABLE 4 below lists the instrument parameters for this Example.

TABLE 4

Instrument Parameters

| | | | |
|---|---|---|---|
| Ramp | ° C./min | ° C. | Hold min |
| Initial | | 40 | 2.5 |
| Ramp 1 | 25 | 320 | 2.8 |
| Runtime | 16.5 min | | |
| Postrun | n/a ° C./min for 0 min | | |
| Inlet | Multimode | | |
| Temp | 320° C. | | |
| Mode | Pulsed Splitless, Constant Flow | | |
| Flow | 0.95 mL/min (adj to lock) | | |
| Pulse Press | 25 psi | | |
| Pulse Time | 1.4 min | | |
| Purge Time | 1.4 min | | |
| Purge Flow | 50 mL/min | | |
| Column | DB-5MSUI part # (121-5523UI) 20 m × 0.18 mm id × 0.36 μm film | | |
| Outlet Pressure | Constant at 2 psig | | |
| Injection volume | 1 μL | | |
| MSD | Agilent 5975C | | |
| Solvent Delay | 3.2 min | | |
| Acquisition Mode | SIM | | |
| SIM Ions | 59 ions in 17 Groups | | |
| Dwell | 5 to 50 msec | | |
| TID | ON | | |
| Quad Temp | 180° C. | | |
| Source Temp | 350° C. | | |
| Transfer Line | 320° C. | | |
| Tune | Atune, Gain 1 | | |
| Backflush Device | Post-column P3-way splitter with overpressure vent | | |
| MSD Restrictor | Inert fused silica tubing | | |
| FID Restrictor | 0.53 m × 0.18 mm id | | |
| Restrictor Flows | 2.0 mL/min at 40 C. | | |
| $H_2$ Addition | Added to makeup | | |
| $H_2$ Flow | 2% of the total flow to each detector | | |

Figure 12:
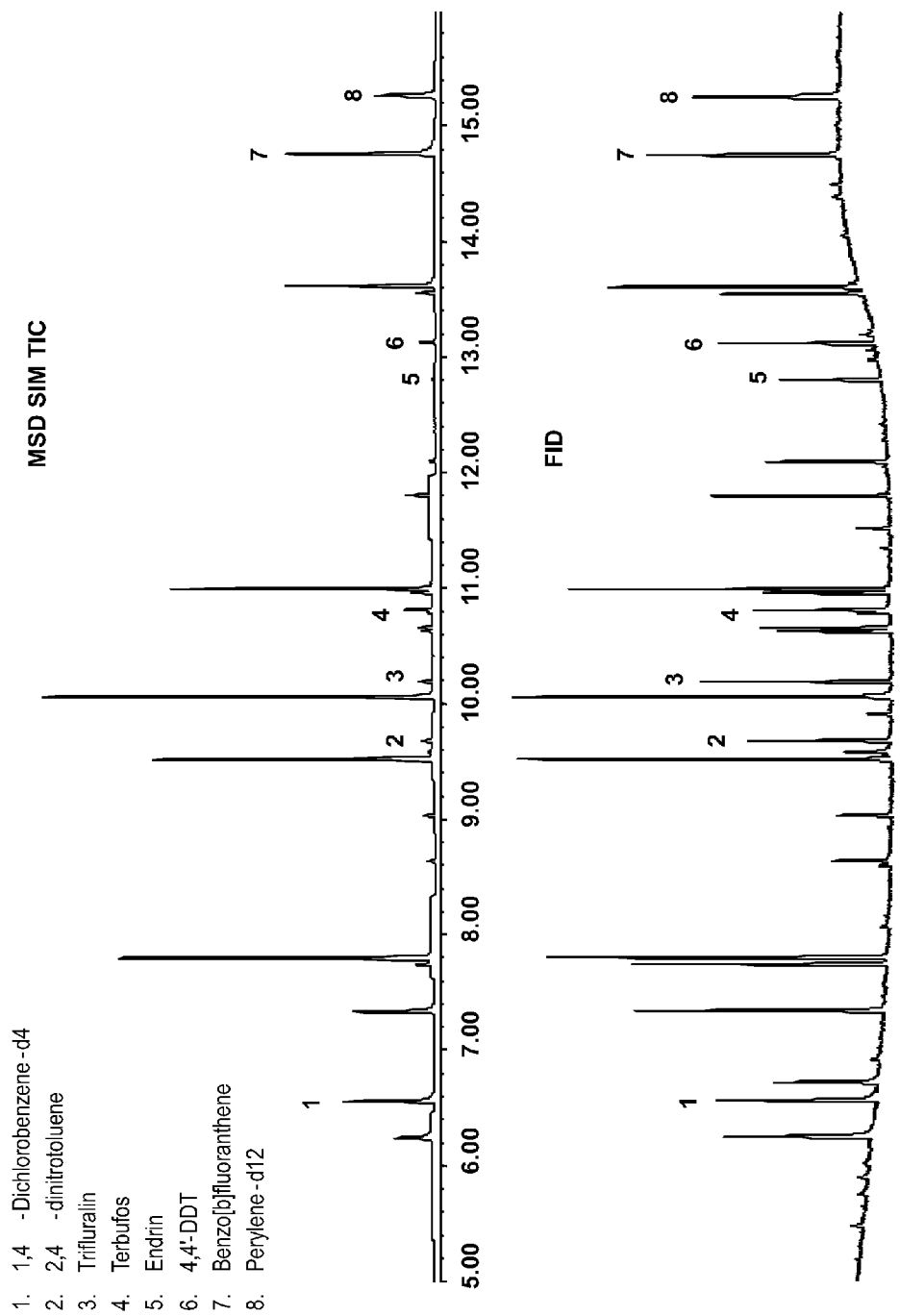
FIG. 12 is an MS SIM TIC and an FID chromatogram obtained from an analysis of a sample of eight pollutants run through the MS system illustrated in FIG. 11.

FIG. 12 is an MS SIM TIC and an FID chromatogram obtained from this Example with hydrogen added. The eight compounds of the sample are listed. All compounds were present at 200 pg into the column 246 and thus at 100 pg to the mass spectrometer 104 and FID 272 each.

Figure 13:
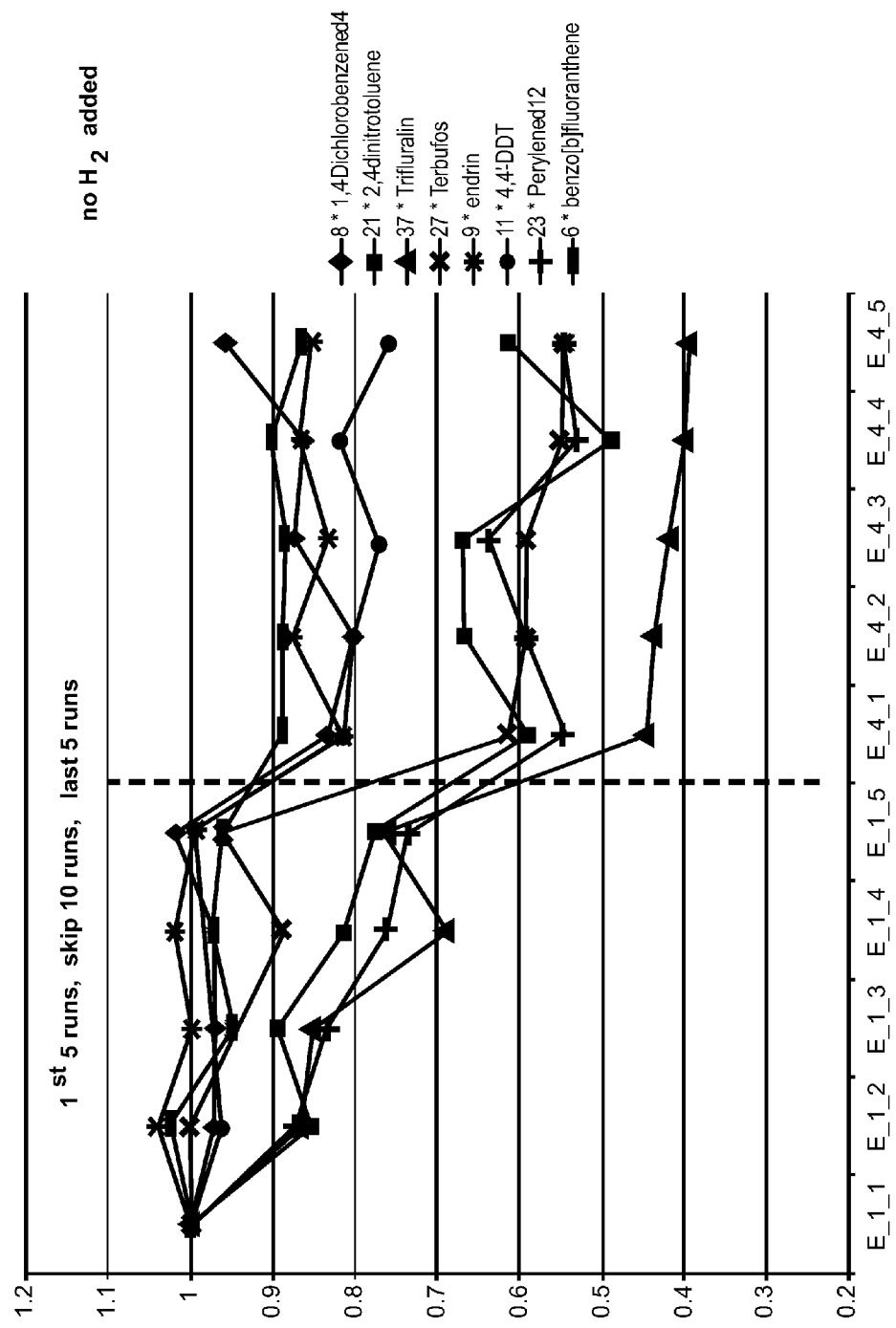
FIG. 13 is a plot of mass spectrometer-to-flame ionization detector (MS:FID) area ratios for the first five and last five of twenty consecutive analyses of the sample of FIG. 12, without a conditioning gas being added in accordance with the present disclosure, wherein the ratios for each compound are normalized to that of the first injection.

A series of twenty replicate runs of the sample were made with no hydrogen added as a control. The areas measured by the mass spectrometer 104 were divided by the areas measured by the FID 272. The ratios were then normalized to that of the first injection and plotted. To make the extent of any drop in responses clearer the normalized ratios from only the first five and last five injections are plotted. FIG. 13 is a plot of this data. Because the column 246 was programmed up to 320° C. and was a relatively new column, the source contamination from column bleed was expected to make the ratios of serial injections drop. This degradation in performance was in fact observed as shown in FIG. 13. In the worst case, Trifluralin, the drop in the MS signal was 60%.

Figure 14:
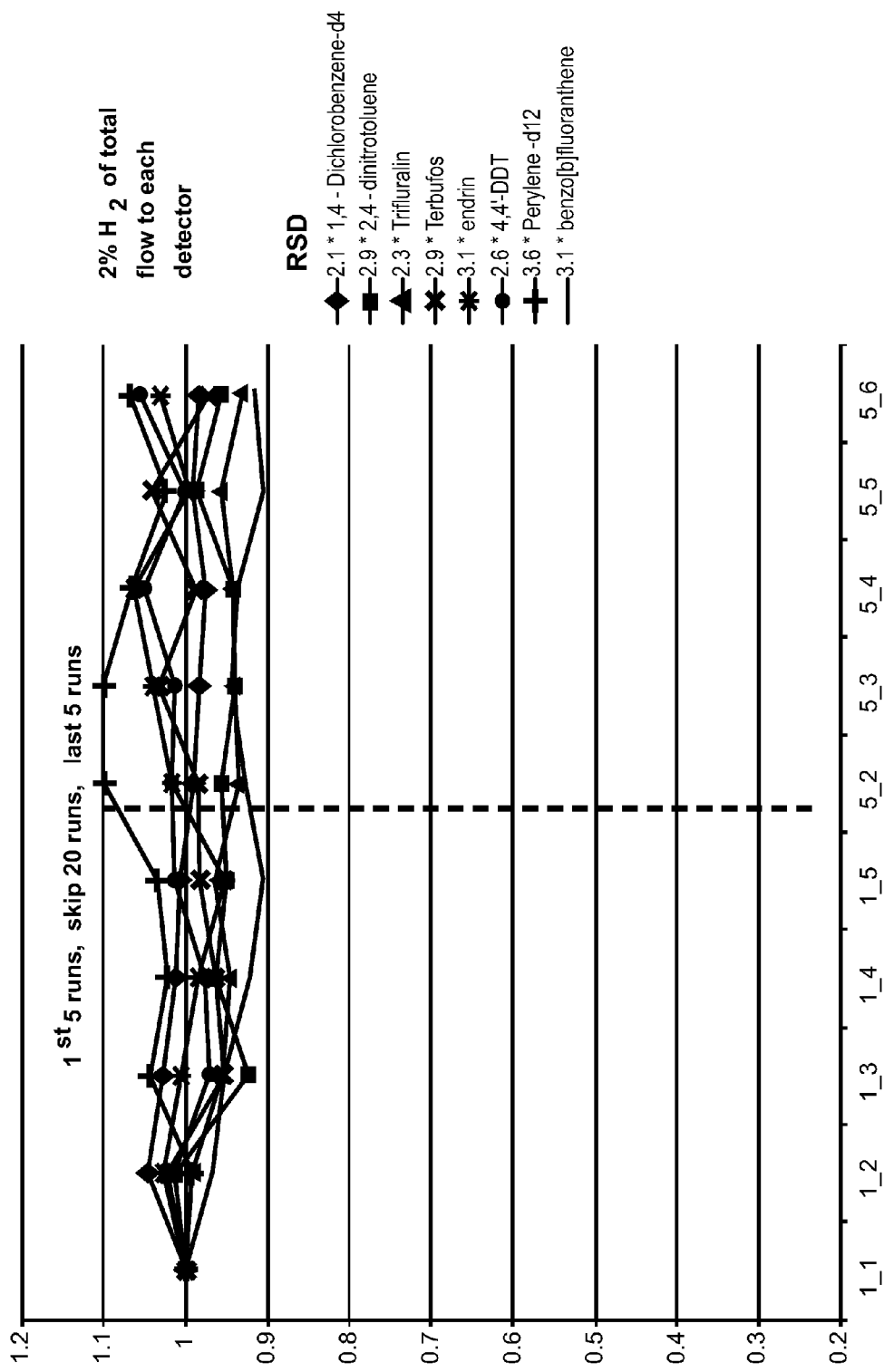
FIG. 14 is a plot of MS:FID area ratios for the first five and last five of thirty consecutive analyses of the sample of FIG. 12, with a conditioning gas being added, wherein the ratios for each compound are normalized to that of the first injection.

FIG. 14 shows the results of the same experiment, except this time with the hydrogen added at 40 μL/min to each of the mass spectrometer 104 and FID 272. As seen in FIG. 14, the added hydrogen eliminates the drop in response.

Example 7

On-Line Conditioning

This Example describes an analysis of a sample of a mixture of solvents including water. This Example was particularly intended to determine the effect of the presently disclosed conditioning process on the reduced MS response that results from the injection of samples containing large amounts of water. For instance, this problem is observed when employing aqueous headspace injections.

Figure 15:
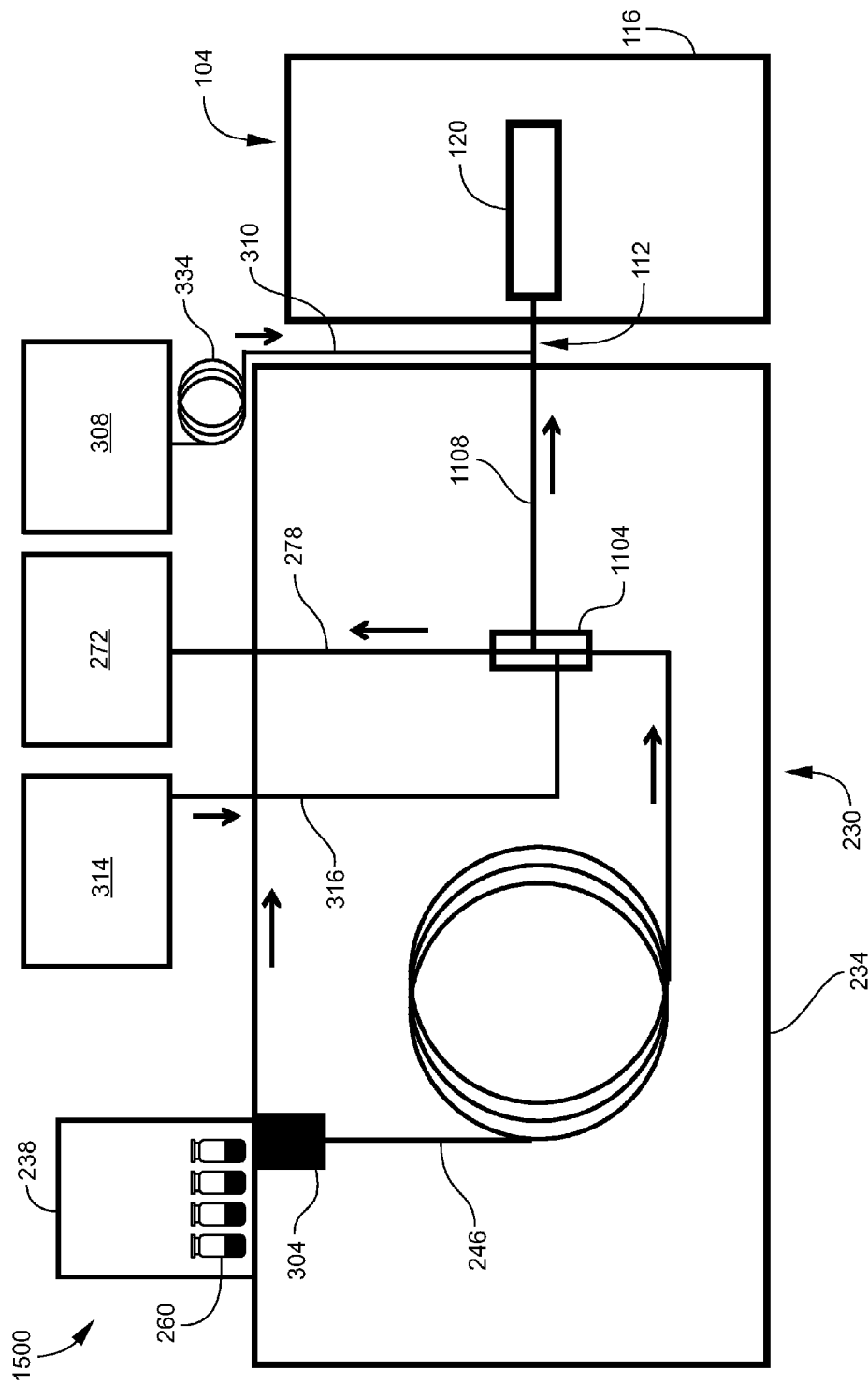
FIG. 15 is a schematic view of another example of an MS system configured for on-line conditioning in accordance with the present disclosure.

FIG. 15 is a schematic view of another example of an MS system 1500 configured in particular for on-line conditioning and utilized in this Example. The MS system 1500 includes many of the same components as the MS system 100 illustrated in FIG. 1, although for simplicity some of these components are not illustrated in FIG. 15. As compared with FIGS. 1, 7 and 11, similar components are designated in FIG. 15 by the same reference numerals. The MS system 1500 illustrated in FIG. 15 includes a first flow controller 308 for the conditioning gas and an associated conditioning gas line 310, and a second flow controller 314 for an auxiliary gas and an associated auxiliary gas line 316. The flow controllers 308, 314 utilized in this Example were programmable EPCs. The MS system 1500 further includes a purged flow splitter 1104 in the GC housing 234 and an FID 272 outside the GC housing 234. Accordingly, the outlet of the column 246 is connected to the purged splitter 1104. A first gas outlet line 1108 interconnects the purged splitter 1104 and the ion source 120. The first gas outlet line 1108 may be considered as an extension of the column 246 or alternatively as a separate gas transfer line. The conditioning gas line 310 is connected to a conduit of the GC/MS interface 112 that coaxially surrounds the first gas outlet line 1108, such that the conditioning gas flows through the annular space defined between the first gas outlet line 1108 and the conduit. The conditioning gas line 310 is connected to a port of the conduit normally utilized for introducing CI reagent gases into the ion source 120. A second gas outlet line 278 interconnects the purged splitter 1104 and the FID 272. The flow splitter 1104 divides the column effluent equally between the mass spectrometer 104 and the FID 272.

In this Example, the carrier gas was helium, the conditioning gas was hydrogen, and the auxiliary gas was helium. The helium carrier gas was supplied to the inlet of the column 246 at a pressure of about 14 psi and flowed through the column 246 at a constant rate of 1.0 mL/min. The first flow controller 308 supplied hydrogen through a restrictor 334, after which the flow rate was 0.07 mL/min. The second flow controller 314 supplied helium to the flow splitter 1104 at a constant pressure of 3.8 psig and at a flow rate of 5 mL/min. As a result, the helium flowed to the mass spectrometer 104 and the FID 272 each at 3 mL/min (at an initial oven temperature of 40° C.). Because the restrictors (not shown) from the flow splitter 1104 to the mass spectrometer 104 and FID 272 are in the oven (the heated GC housing 234) and the flow splitter 1104 is maintained at constant pressure by the second flow controller 314, the flow of helium to each of the mass spectrometer 104 and FID 272 dropped from 3 mL/min at the initial oven temperature of 40° C. to 1.36 mL/min at 220° C. The amount of hydrogen reaching the mass spectrometer 104, however, stayed constant at 0.07 mL/min. Thus, by the configuration illustrated in FIG. 15, samples can be easily run with or without implementing the conditioning process employed in this Example (i.e., turning the hydrogen flow on or off). In this Example, the injection solvent for the mixture of solvents was water. The injection was a 20:1 split injection of 1 μL of the mixture, putting 50 nL (50 μg) of water into the ion source 120 with each injection.

TABLE 5 below lists the instrument parameters for this Example.

TABLE 5

Instrument Parameters

| | °C./min | °C. | Hold min |
|---|---|---|---|
| Ramp | | | |
| Initial | | 40 | 1 |
| Ramp 1 | 10 | 220 | 2 |
| Runtime | 21 min | | |
| Inlet | Split/Splitless | | |
| Temp | 280° C. | | |
| Mode | Split, Constant Flow | | |
| Flow | 1.0 mL/min | | |
| Inlet Press | 14 psi | | |
| Split Flow | 20 mL/min | | |
| Column | DB-5MSUI part # (122-5536UI) | | |
| | 30 m × 0.25 mm id × 0.5 µm film | | |
| Outlet Pressure | Constant at 3.8 psig | | |
| Injection volume | 1 µL | | |
| MSD | Agilent 5975C | | |
| Solvent Delay | 0 min | | |
| Acquisition Mode | SIM | | |
| SIM Ions | 17 ions in 3 Groups | | |
| Dwell | 25 msec | | |
| TID | OFF | | |
| Quad Temp | 180° C. | | |
| Source Temp | 300° C. | | |
| Transfer Line | 260° C. | | |
| Tune | Atune, Gain 1 | | |
| Splitter Device | Post-column 2-way splitter | | |
| Splitter Pressure | Constant at 3.8 psig | | |
| Restrictors | Inert fused silica tubing | | |
| MSD Restrictor | 0.95 mm × 0.15 mm id | | |
| FID Restrictor | 0.35 m × 0.15 mm id | | |
| Restrictor Flows | 3.0 mL/min at 40 C. | | |
| $H_2$ Addition | Added at source | | |
| $H_2$ Flow | 70 µL/min | | |
| $H_2$ Restrictor | 25 mm × 0.015 mm id | | |

Figure 16:
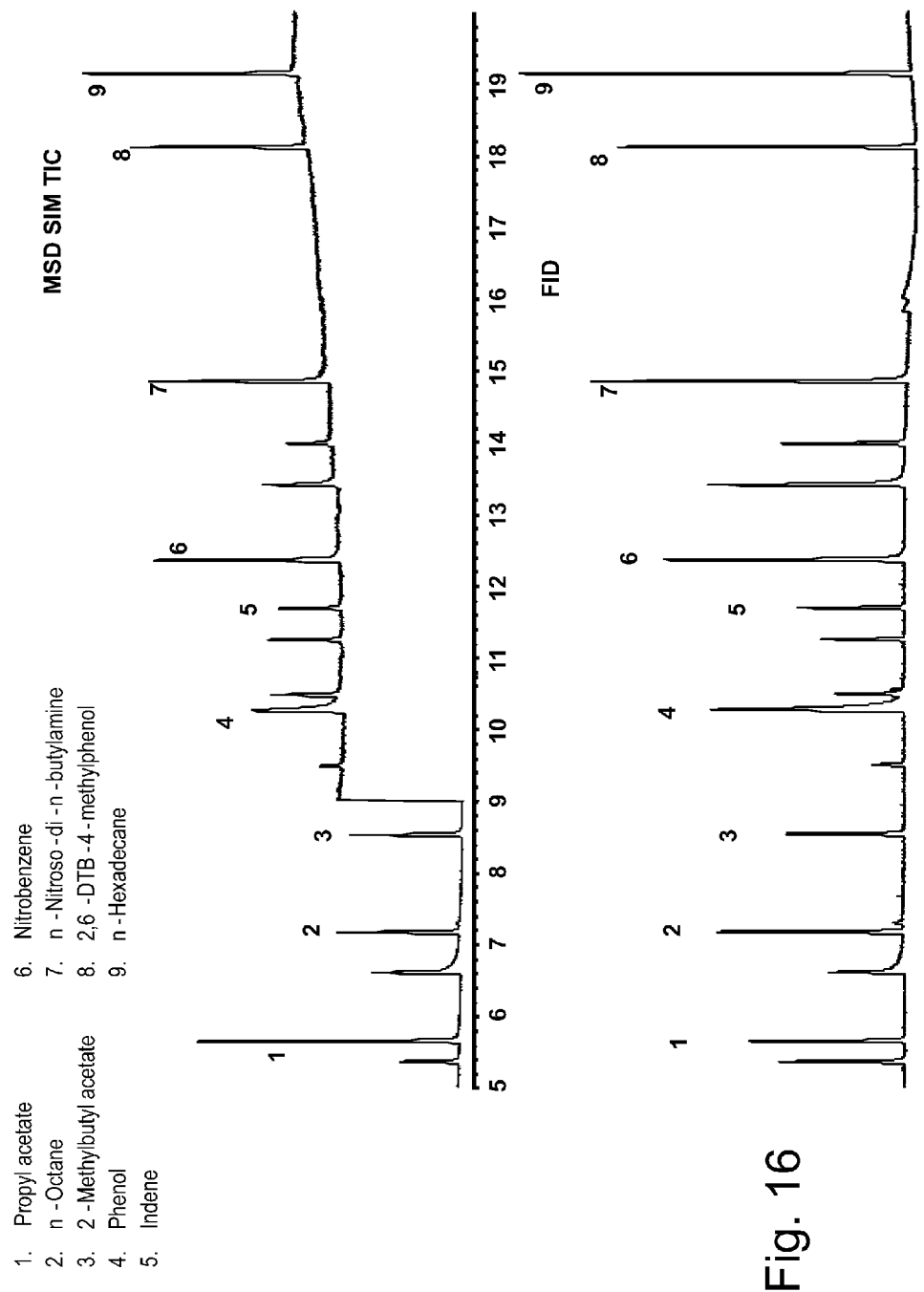
FIG. 16 is an MS SIM TIC and an FID chromatogram obtained from an analysis of a sample of nine solvent compounds run through the MS system illustrated in FIG. 15.

FIG. 16 is an MS SIM TIC and an FID chromatogram obtained from this Example with hydrogen added. The nine solvent compounds of the sample are listed. All compounds were present at 1 ng into the column 246 and thus at 500 pg to the mass spectrometer and FID each.

Figure 17:
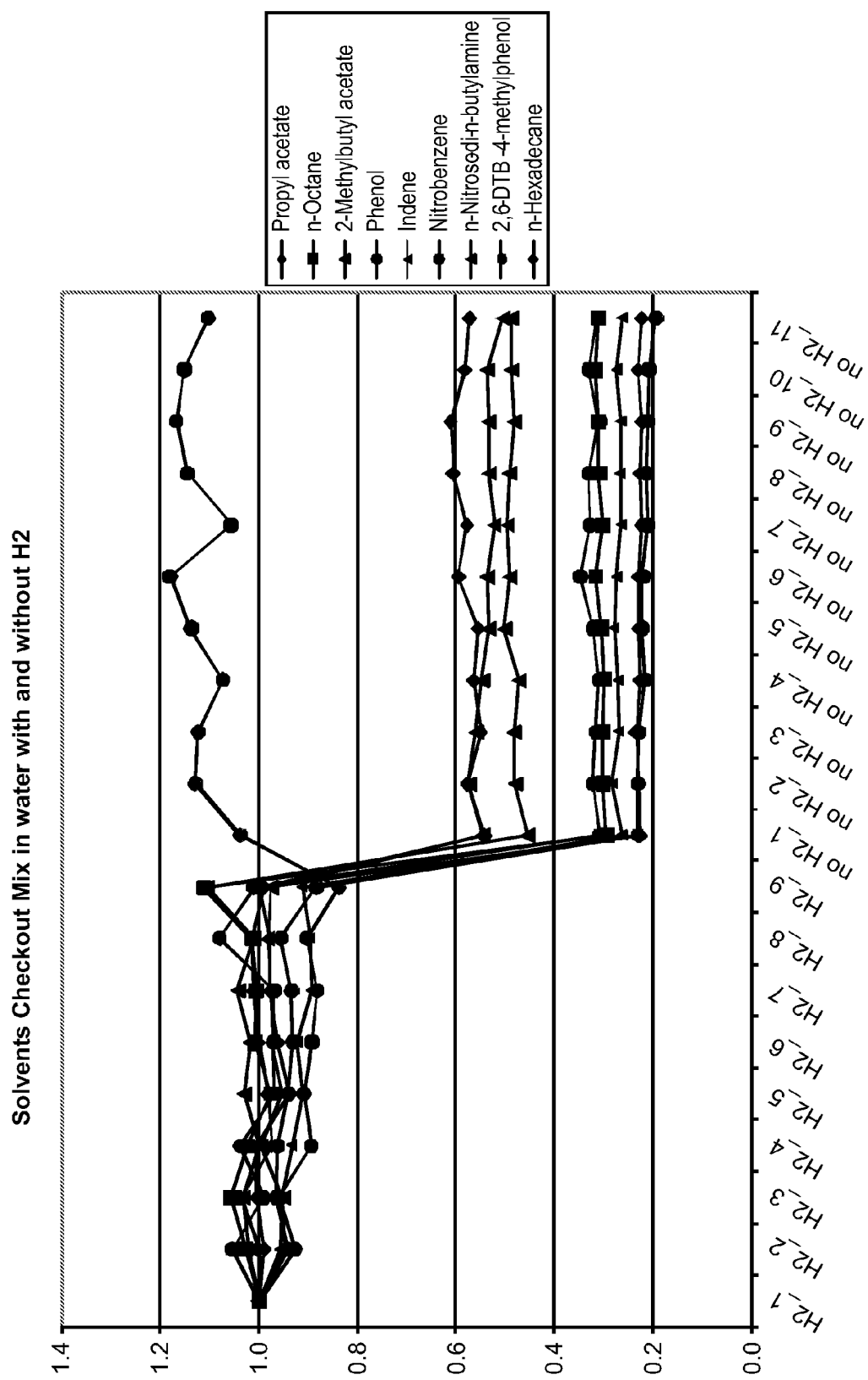
FIG. 17 is a plot of mass spectrometer-to-flame ionization detector (MS:FID) area ratios for nine consecutive analyses of the sample of FIG. 16 with a conditioning gas added in accordance with the present disclosure, followed by eleven consecutive analyses of the sample without the conditioning gas being added, wherein the ratios for each compound are normalized to that of the first injection made with the hydrogen added.

A series of nine replicate runs of the sample were made with hydrogen added, followed by eleven replicate runs of the sample made with no hydrogen added as a control. The areas measured by the mass spectrometer 104 were divided by the areas measured by the FID 272. The ratios were then normalized to that of the first injection made with hydrogen added and plotted. FIG. 17 is a plot of this data. As shown in FIG. 17, in the absence of hydrogen the MS response signals were suppressed between 40% and 75% for all compounds except nitrobenzene. By comparison, the presence of hydrogen significantly improved the MS performance. FIG. 17 thus demonstrates the improvement in performance with samples with which water is injected.

Example 8

On-Line Conditioning

Figure 18:
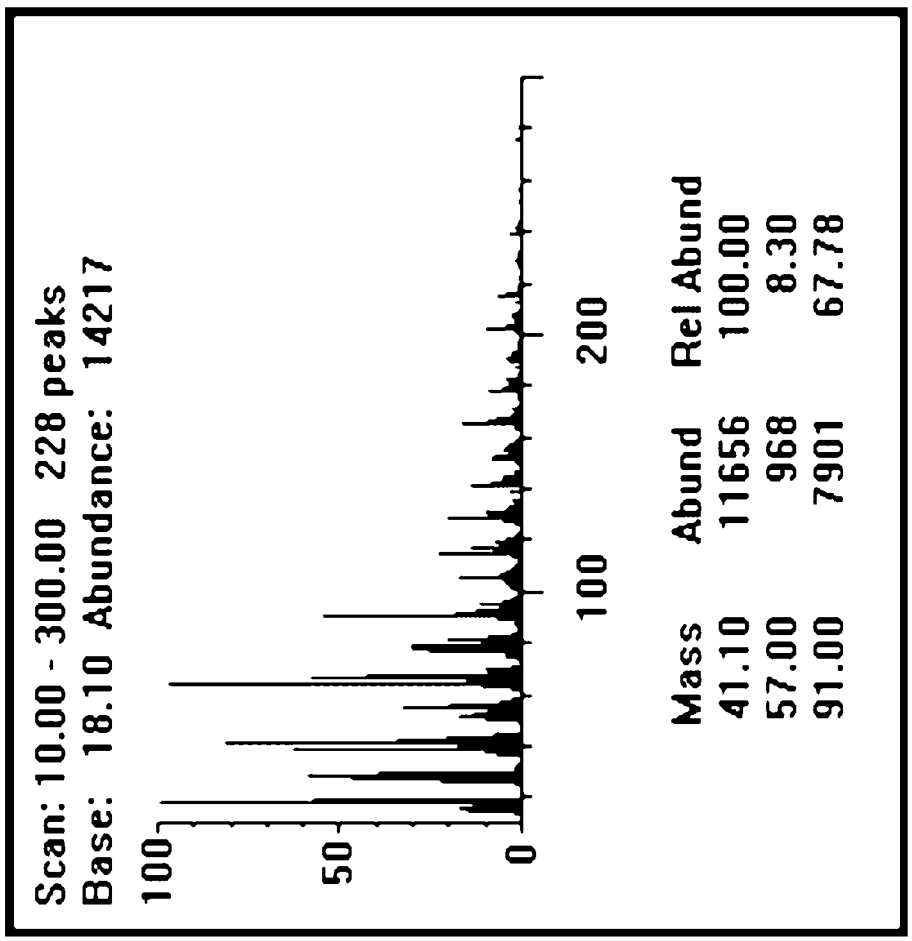
FIG. 18 shows a typical spectrum of background ion masses observed when employing only hydrogen as the carrier gas in a typical GC/MS system.
Figure 20:
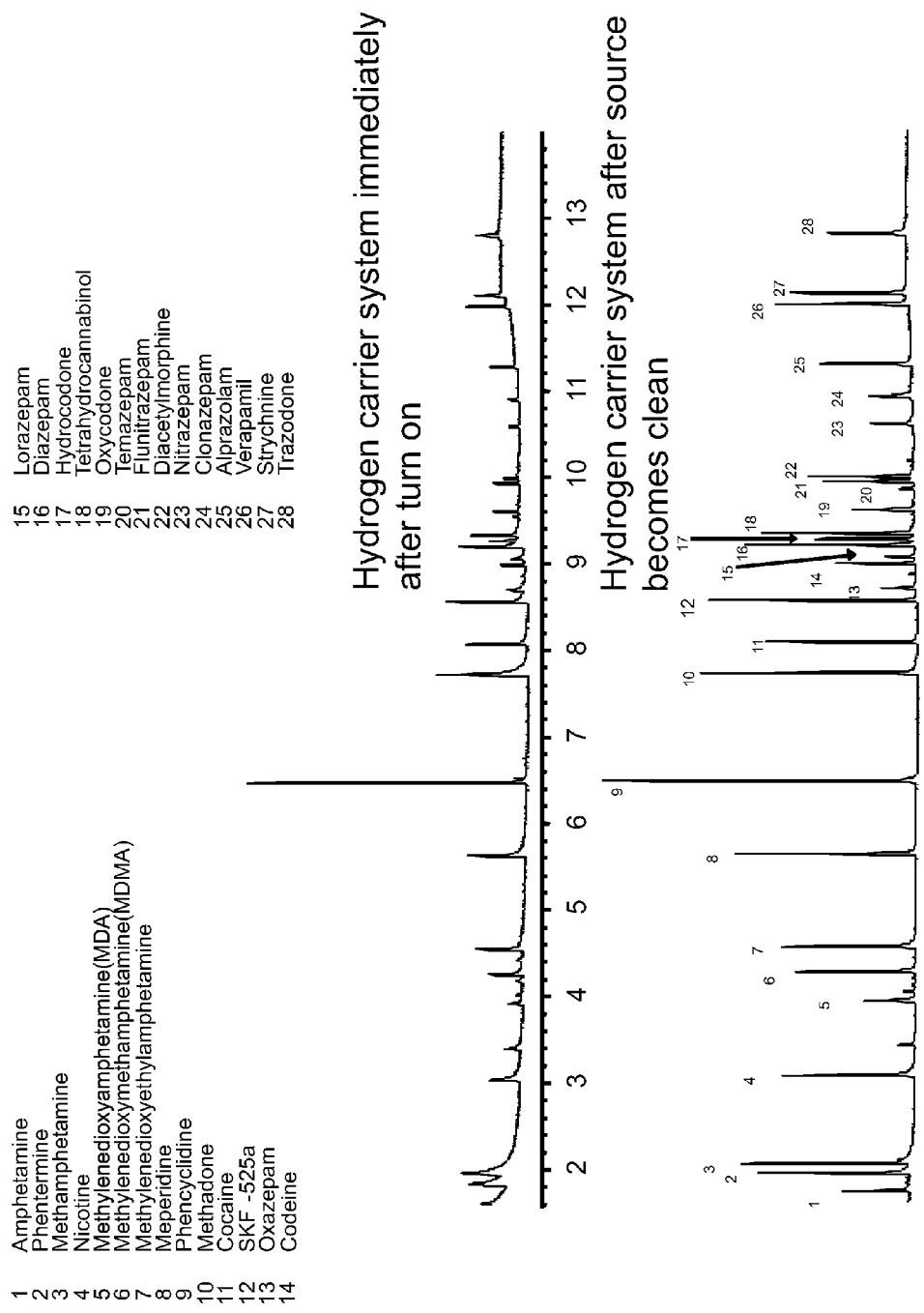
FIG. 20 shows two TICs obtained from a chromatographic run of sample of twenty-eight compounds through the MS system illustrated in FIG. 19, utilizing hydrogen as a carrier gas and helium as a post-column auxiliary, wherein the upper TIC was shortly after the chromatographic run was initiated and the lower TIC was acquired after the MS system became clean.

In this Example, the relative amounts of hydrogen and helium were reversed, and hydrogen was utilized as the carrier gas for running a sample through the column. It has been observed that when setting up a GC/MS system with hydrogen as the carrier gas, as soon as the ion source is turned on, a very high background of many ions is observed. FIG. 18 shows a typical spectrum of background ion masses observed when employing only hydrogen as the carrier gas in a typical GC/MS system. The high background is accompanied by a poor S/N ratio and poor peak shapes, as seen in the TIC for the analytes (FIG. 20). This background takes a very long time to come down. It often takes a few weeks of operation before the background drops to a level at which the peak shape and S/N performance are acceptable.

In this Example, the addition of helium into the hydrogen gas stream at a point upstream of the ion source was found to facilitate cleaning the ion source during use. The flow of helium was maintained for over 30 chromatographic runs, and was found to greatly improve the background in one day instead of a few weeks. It is believed that the presence of the helium in the ion source may increase the effectiveness of the hydrogen as a conditioning agent. Without wishing to be bound by any one particular theory, it is possible the partial pressure of helium in the presence of hydrogen provides a higher overall pressure inside the source which increases the opportunity for surface related phenomena related to the "cleaning" or surface conditioning. This is because species such as metastable helium are also generated, which may assist in the conditioning activity, as well as the possibility of other charge-exchange or dissociated species that may be absent in pure hydrogen.

Figure 19:
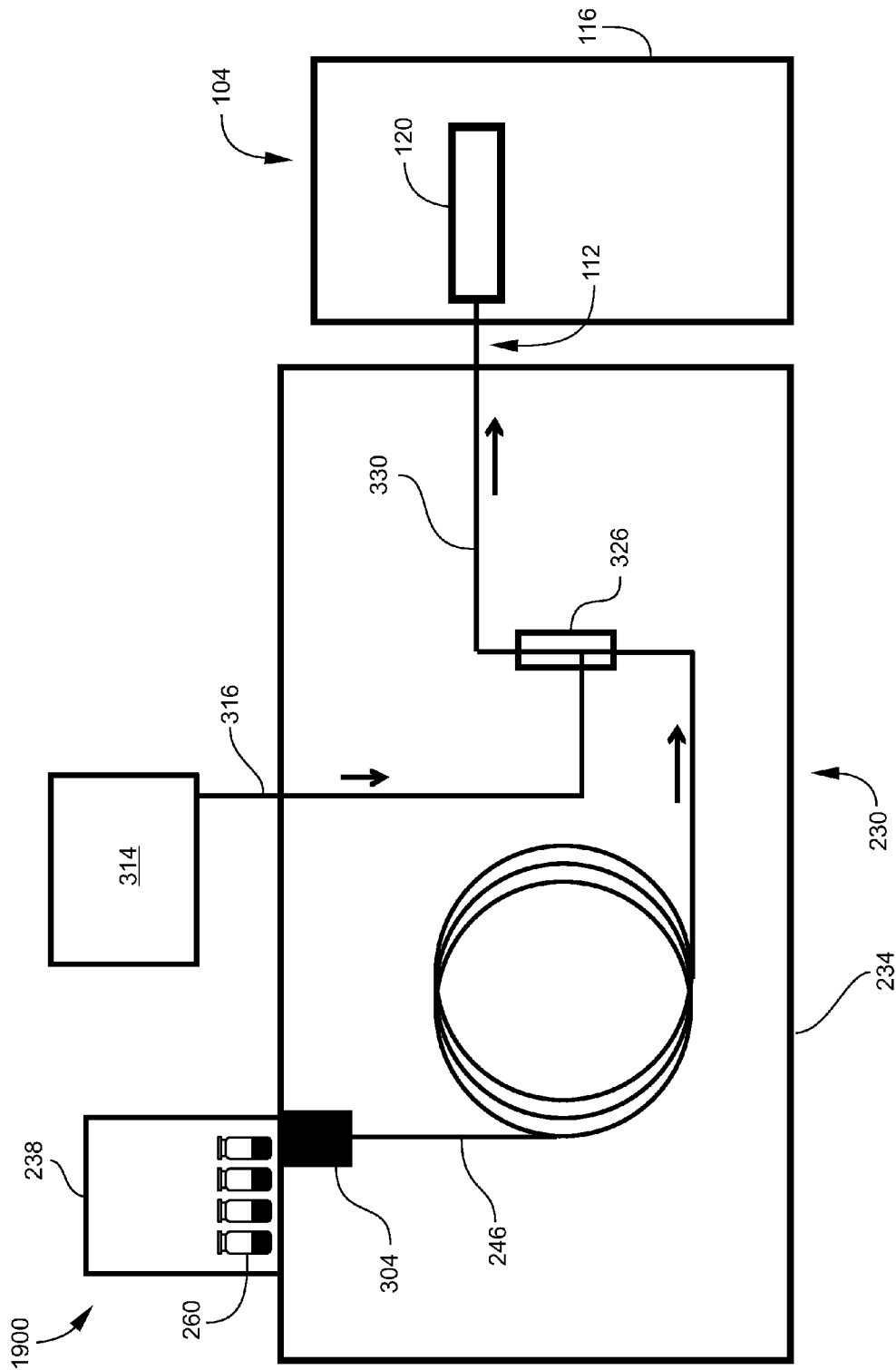
FIG. 19 is a schematic view of another example of an MS system configured for on-line conditioning in accordance with the present disclosure.

FIG. 19 is a schematic view of another example of an MS system 1900 configured in particular for on-line conditioning and utilized in this Example. The MS system 1900 includes many of the same components as the MS system 100 illustrated in FIG. 1, although for simplicity some of these components are not illustrated in FIG. 19. As compared with FIGS. 1, 7, 11 and 15, similar components are designated in FIG. 19 by the same reference numerals. The MS system 1900 illustrated in FIG. 19 a conditioning gas source that in this Example also serves as the carrier gas source (not shown) communicating with the inlet of the column 246. That is, the hydrogen serves the dual roles of a carrier gas for the sample and a conditioning gas for the MS system 1900. The MS system 1900 further includes a flow controller 314 for an auxiliary gas (helium in this Example) and an associated auxiliary gas line 316. The flow controller 314 utilized in this Example was a programmable EPC. The MS system 1900 further includes a purged union 326 in the GC housing 234 to which the outlet of the column 246 and the auxiliary gas line 316 are connected. A gas transfer line 330 interconnects the purged union 326 and the ion source 120. The gas transfer line 330 may be considered as an extension of the column 246 or alternatively as a separate gas line. The hydrogen carrier gas was supplied to the inlet of the column 246 at a pressure of about 14 psi and flowed through the column 246 at a constant rate of 1.11 mL/min. The purged union facilitated 326 the addition of the stream of helium to the sample/hydrogen stream flowing from the column 246. The flow controller 314 supplied helium at a flow rate of 0.13 mL/min. During the chromatographic run, the hydrogen/helium mixture flowed into the ion source 120 at 1.24 mL/min.

TABLE 6 below lists the instrument parameters for this Example.

TABLE 6

Instrument Parameters

| | °C./min | °C. | Hold min |
|---|---|---|---|
| Ramp | | | |
| Initial | | 90 | 0.0 |
| Ramp 1 | 20 | 325 | 2.5 |
| Runtime | 14.5 min | | |
| Inlet | Split/Splitless | | |
| Temp | 280° C. | | |
| Mode | Pulsed Splitless, Constant Pressure | | |
| Pulse Pressure | 40 psig $H_2$ until 0.75 min | | |
| Pressure | 14.0 psig $H_2$ | | |
| Purge Flow | 50 mL/min | | |
| Purge time | 0.75 min | | |
| Septum Purge | Switched, 3 mL/min | | |
| Column | DB-5MSUI part # (121-5522UI) | | |
| | 20 m × 0.18 mm id × 0.18 µm film | | |

TABLE 6-continued

Instrument Parameters

| | |
|---|---|
| Initial Flow | 1.16 mL/min |
| Outlet Pressure | Vacuum |
| Injection volume | 1 μL |
| MSD | Agilent 5975C |
| Solvent Delay | 1.5 min |
| Acquisition Mode | Scan |
| Scan Range | 40 to 570 |
| Threshold | 0 |
| Sampling | 1 |
| Quad Temp | 150° C. |
| Source Temp | 300° C. |
| Transfer Line | 300° C. |
| Tune | Gain Normalized 1X |
| He Addition | Added with purged union |
| He Flow | 130 mL/min |
| He Restrictor | 0.5 m × 0.05 mm id |

FIG. 20 shows two TICs obtained from this Example. The top trace was acquired shortly after the chromatographic run was initiated. The bottom trace was acquired after the MS system 1900 became clean after about twenty-four hours and with the helium flow turned on. The sample was a toxicology test mix of twenty-eight compounds, which are listed in FIG. 20. The improvement in S/N ratio and peak shape as a result of the addition of the helium to the hydrogen carrier gas is clearly evident from FIG. 20. As noted above, this cleaning effect may occur in a few days instead of a few weeks.

Exemplary Embodiments

Exemplary embodiments provided in accordance with the presently disclosed subject matter include, but are not limited to, the following:

1. A mass spectrometer (MS) system, comprising:
a mass spectrometer comprising a sample interface and an ionization chamber communicating with the sample interface;
a conditioning gas line configured for supplying a conditioning gas;
means for operating in an analytical mode, configured for establishing a sample flow path through the sample interface and into the ionization chamber; and
means for operating in a conditioning mode, configured for establishing a conditioning gas flow path through the conditioning gas line and into the mass spectrometer.

2. The MS system of embodiment 1, comprising a gas chromatograph (GC) housing communicating with the sample interface, wherein the sample gas flow path runs from the GC housing into the sample interface.

3. The MS system of embodiment 2, wherein the conditioning gas line communicates with the sample interface from a location in the GC housing.

4. The MS system of embodiment 1, comprising a column, the column comprising a column inlet and a column outlet, wherein the column inlet communicates with the conditioning gas line, the column outlet communicates with the ionization chamber via the sample interface, and the conditioning gas flow path runs into the column inlet and through the column.

5. The MS system of embodiment 4, comprising a carrier gas source communicating with the column, wherein the means for operating in the conditioning mode is configured for regulating respective flows of the carrier gas and the conditioning gas into the column inlet, and the proportion of the carrier gas relative to the conditioning gas flowing into the column inlet ranges from 0% to less than 100%.

6. The MS system of embodiment 4, wherein the column extends through the sample interface, the sample interface comprises a conduit communicating with the ionization chamber, the conditioning gas line communicates with the conduit, and the conditioning gas flow path runs through the conduit.

7. The MS system of embodiment 6, comprising an auxiliary gas line configured for supplying a reagent gas for chemical ionization and communicating with the conduit, and a flow control device communicating with the auxiliary gas line, wherein:
the conditioning gas line communicates with the flow control device;
the means for operating in the analytical mode is configured for operating the flow control device to establish a reagent gas flow path through the auxiliary gas line, through the conduit and into the ionization chamber; and
the means for operating in the conditioning mode is configured for operating the flow control device to establish the conditioning gas flow path from the conditioning gas line, through the auxiliary gas line, through the conduit and into the ionization chamber.

8. The MS system of embodiment 4, wherein the conditioning gas line communicates directly with the mass spectrometer separately from the column.

9. The MS system of embodiment 4, comprising a flow splitter communicating with the column, a gas outlet line communicating with the flow splitter, a gas detector communicating with the gas outlet line, a mass analyzer communicating with the ionization chamber, and an ion detector communicating with the mass analyzer, wherein the flow splitter is configured for splitting a sample/gas flow in the column into a first output flow directed into the ionization chamber and a second output flow directed via the gas outlet line into the gas detector, and the means for operating in the conditioning mode is configured for determining whether the MS system should be operated in the conditioning mode based on comparing a chromatogram or other analytical data produced from the ion detector from an analysis of a sample with a chromatogram or other analytical data produced from the gas detector from the same analysis.

10. The MS system of embodiment 1, comprising a column, the column comprising a column inlet and a column outlet, wherein the column outlet communicates with the ionization chamber via the sample interface, the conditioning gas line communicates with a section of the column between the column inlet and the column outlet, and the conditioning gas flow path runs into the section and through the column.

11. The MS system of embodiment 1, comprising an auxiliary gas source communicating with the conditioning gas line for supplying an auxiliary gas different from the conditioning gas, wherein the means for operating in the conditioning mode is configured for regulating respective flows of the auxiliary gas and the conditioning gas.

12. The MS system of embodiment 1, wherein the means for operating in the conditioning mode is configured for maintaining the ionization chamber at a temperature ranging from −20 to 800° C.

13. The MS system of embodiment 12, wherein the means for operating in the conditioning mode is configured for operating an ionization device to excite the conditioning gas in the ionization chamber.

14. The MS system of embodiment 1, wherein the means for operating in the conditioning mode is configured for controlling a temperature selected from the group consisting of: a temperature of a housing communicating with the sample interface; a temperature of a column communicating with the sample interface; a temperature of the sample interface; a temperature of the ionization chamber; a temperature of a mass analyzer communicating with the ionization chamber; a temperature of a detector of the mass spectrometer; and a combination of two of more of the foregoing.

15. The MS system of embodiment 1, wherein the means for operating in the conditioning mode comprises a device selected from the group consisting of a manual user input, an electronic processor, a logic instruction executable by an electronic processor residing in a local memory of the MS system or a remote memory accessible by the electronic processor, or a combination of two or more of the foregoing.

16. The MS system of embodiment 1, wherein the means for operating in the conditioning mode is configured for evaluating a parameter of the MS system and, based on the parameter, determining whether the MS system should be operated in the conditioning mode.

17. The MS system of embodiment 16, wherein the parameter is selected from the group consisting of: a number of times a component of the MS system has been operated in the analytical mode prior to evaluating the parameter; an amount of time elapsed prior to evaluating the parameter; a quality of a chromatogram, mass spectrum or other analytical data produced by the MS system under predetermined operating conditions; a signal-to-noise ratio of a chromatogram, mass spectrum or other analytical data produced by the MS system under predetermined operating conditions; a measurement of an abundance of ions of one or more selected mass-to-charge ratios taken while operating in the conditioning mode; the presence of stationary phase material separated from a stationary phase support of the column; and a combination of two or more of the foregoing.

18. The MS system of embodiment 16, wherein the means for operating in the analytical mode is configured for taking an action based on determining whether the MS system should be operated in the conditioning mode, and the action is selected from the group consisting of switching the operation of the MS system to the conditioning mode, scheduling a time for switching the operation of the MS system to the conditioning mode, modifying a pre-scheduled time for switching the operation of the MS system to the conditioning mode, producing a user-readable indication that the MS system should be operated in the conditioning mode, and a combination of two of more of the foregoing.

19. The MS system of embodiment 1, comprising a mass analyzer communicating with the ionization chamber and an ion detector communicating with the mass analyzer, wherein the means for operating in the conditioning mode comprises means for monitoring a chromatogram, mass spectrum or other analytical data produced from the ion detector while operating in the conditioning mode.

20. A method for operating a mass spectrometer (MS) system, the method comprising:
operating the MS system in an analytical mode by introducing a sample and a carrier gas into an ionization chamber of the MS system;
ceasing operating the MS system in the analytical mode by ceasing the flowing of the sample; and
operating the MS system in a conditioning mode to condition one or more components of a mass spectrometer of the MS system by flowing a conditioning gas into the mass spectrometer, wherein the conditioning gas is different from the carrier gas.

21. The method of embodiment 20, wherein the carrier gas is selected from the group consisting of helium, nitrogen, and argon.

22. The method of embodiment 20 or 21, wherein the conditioning gas is flowed from a source containing a blend of the conditioning gas and an auxiliary gas different from the conditioning gas.

23. The method of embodiment 22, wherein the proportion of the conditioning gas relative to the auxiliary gas in the source ranges from 0% to less than 100% by volume.

24. The method of embodiment 22, wherein the auxiliary gas is the same as the carrier gas.

25. The method of any one of embodiments 20-24, wherein ceasing operating in the analytical mode comprises ceasing the flowing of the carrier gas.

26. The method of any one of embodiments 20-24, wherein ceasing operating in the analytical mode comprises reducing a flow rate of the carrier gas, and operating in the conditioning mode comprises continuing to flow the carrier gas at the reduced flow rate.

27. The method of any one of embodiments 20-26, wherein flowing the conditioning gas into the mass spectrometer comprises a step selected from the group consisting of: flowing the conditioning gas with the carrier gas into a column inlet of a column communicating with the ionization chamber; flowing the conditioning gas into a section of the column between the column inlet and a column outlet of the column; flowing the conditioning gas into a conduit of a sample interface of the MS system through which the column extends, wherein conduit and the column communicate separately with the ionization chamber; flowing the conditioning gas directly into the mass spectrometer via a gas line separate from the column; and a combination of two or more of the foregoing.

28. The method of any one of embodiments 20-27, wherein the conditioning gas is flowed through a column and into the ionization chamber, and comprising regulating respective flows of the carrier gas and the conditioning gas such that the proportion of the carrier gas flowing into the column inlet ranges from 0% to less than 100%.

29. The method of any one of embodiments 20-27, wherein a column communicates with the ionization chamber, and the conditioning gas is flowed into a section of the column between a column inlet and a column outlet of the column, through the column and into the ionization chamber, and comprising regulating the flow of the conditioning gas and an auxiliary gas into the section.

30. The method of embodiment 29, wherein the auxiliary gas is the same as the carrier gas.

31. The method of any one of embodiments 20-27, wherein the MS system comprises a sample interface through which the column extends, and the interface comprises a conduit communicating with the ionization chamber, and wherein operating in the conditioning mode comprises flowing the conditioning gas through the conduit and into the ionization chamber, operating in the analytical mode comprises flowing a reagent gas through the conduit and into the ionization chamber to perform chemical ionization, and ceasing operating in the analytical mode comprises ceasing the flowing of the reagent gas into the conduit, wherein the reagent gas is different from the conditioning gas.

32. The method of any one of embodiments 20-31, wherein operating in the conditioning mode comprises maintaining the ionization chamber at a temperature ranging from −20 to 800° C.

33. The method of embodiment 32, wherein operating in the conditioning mode comprises exciting the conditioning gas in the ionization chamber.

34. The method of any one of embodiments 20-33, wherein operating in the conditioning mode comprises controlling a temperature selected from the group consisting of: a temperature of a housing in which a column is disposed, wherein the column communicates with the ionization chamber; a temperature of the column; a temperature of a sample interface through which the column extends; a temperature of the ionization chamber; a temperature of the mass analyzer; a temperature of a detector of the mass spectrometer; and a combination of two of more of the foregoing.

35. The method of any one of embodiments 20-34, comprising evaluating a parameter of the MS system and, based on the parameter, determining whether the MS system should be operated in the conditioning mode.

36. The method of embodiment 35, wherein the parameter is selected from the group consisting of: a number of times a component of the MS system has been operated in the analytical mode prior to evaluating the parameter; an amount of time elapsed prior to evaluating the parameter; a quality of a chromatogram, mass spectrum or other analytical data produced by the MS system under predetermined operating conditions; a signal-to-noise ratio of a chromatogram, mass spectrum or other analytical data produced by the MS system under predetermined operating conditions; a measurement of an abundance of ions of one or more selected mass-to-charge ratios taken while operating in the conditioning mode; the presence of stationary phase material separated from a stationary phase support of the column; and a combination of two or more of the foregoing.

37. The method of embodiment 36, wherein if it is determined that the MS system should be operated in the conditioning mode, performing a step selected from the group consisting of switching the operation of the MS system from the analytical mode to the conditioning mode, scheduling a time for switching the operation of the MS system to the conditioning mode, modifying a pre-scheduled time for switching the operation of the MS system to the conditioning mode, producing a user-readable indication that the MS system should be operated in the conditioning mode, and a combination of two or more of the foregoing.

38. The method of any one of embodiments 20-37, comprising flowing the sample and the carrier gas flow through a stationary phase of the column to produce a mixture of the carrier gas and separated components of the sample, splitting the mixture into a first output flow directed into the ionization chamber and a second flow directed to a gas detector separate from an ion detector associated with the ionization chamber, producing respective chromatograms or other analytical data from the ion detector and the gas detector, and determining whether the MS system should be operated in the conditioning mode based on comparing the respective chromatograms or other analytical data.

39. The method of any one of embodiments 20-38, comprising monitoring a chromatogram, mass spectrum or other analytical data produced by the MS system while operating in the conditioning mode.

40. A mass spectrometer (MS) system, comprising:
a mass spectrometer comprising a sample interface and an ionization chamber communicating with the sample interface;
a conditioning gas line configured for communicating with a conditioning gas source and for directing a conditioning gas toward the mass spectrometer; and
means for regulating respective flows of a carrier gas and the conditioning gas into the mass spectrometer.

41. The MS system of embodiment 40, wherein the means for regulating respective flows is configured for regulating such that the proportion of the conditioning gas flowing into the mass spectrometer ranges from 0% to less than 100% by volume.

42. The MS system of embodiment 40, comprising a gas chromatograph (GC) housing communicating with the sample interface, wherein the conditioning gas line communicates with the sample interface from a location in the GC housing.

43. The MS system of embodiment 40, comprising a column, the column comprising a column inlet and a column outlet, wherein the column inlet communicates with the conditioning gas line, and the column outlet communicates with the ionization chamber via the sample interface.

44. The MS system of embodiment 43, wherein the column extends through the sample interface, the sample interface comprises a conduit communicating with the ionization chamber, and the conditioning gas line communicates with the conduit.

45. The MS system of embodiment 44, comprising an auxiliary gas line communicating with the conduit for supplying a reagent gas for chemical ionization, and a flow control device communicating with the auxiliary gas line, wherein the conditioning gas line communicates with the flow control device, and the means for regulating respective flows is configured for operating the flow control device to control respective flows of the conditioning gas and the reagent gas through the auxiliary gas line.

46. The MS system of embodiment 43, wherein the conditioning gas line communicates directly with the mass spectrometer separately from the column.

47. The MS system of embodiment 43, comprising a flow splitter communicating with the column, a gas outlet line communicating with the flow splitter, a gas detector communicating with the gas outlet line, a mass analyzer communicating with the ionization chamber, and an ion detector communicating with the mass analyzer, wherein the flow splitter is configured for splitting a sample/gas flow in the column into a first output flow directed into the ionization chamber and a second output flow directed via the gas outlet line into the gas detector, and the means for regulating respective flows is configured for regulating based on comparing a chromatogram or other analytical data produced from the ion detector from an analysis of a sample with a chromatogram or other analytical data produced from the gas detector from the same analysis.

48. The MS system of embodiment 40, comprising a column, the column comprising a column inlet and a column outlet, wherein the column outlet communicates with the ionization chamber via the sample interface, and the conditioning gas line communicates with a section of the column between the column inlet and the column outlet.

49. The MS system of embodiment 48, comprising an auxiliary gas source communicating with the conditioning gas line for supplying an auxiliary gas different from the conditioning gas, wherein the means for regulating respective flows is configured for regulating respective flows of the auxiliary gas and the conditioning gas, and the proportion of the auxiliary gas flowing through the conditioning gas line ranges from 0% to less than 100%.

50. The MS system of embodiment 40, wherein the means for regulating respective flows is configured for evaluating a parameter of the MS system, and regulating the flow of the conditioning gas based on the parameter.

51. The MS system of embodiment 50, wherein the parameter is selected from the group consisting of: a number of times a component of the MS system has been operated to perform sample analyses prior to evaluating the parameter; an amount of time elapsed prior to evaluating the parameter; a quality of a chromatogram, mass spectrum or other analytical data produced by the MS system under predetermined operating conditions; a signal-to-noise ratio of a chromatogram, mass spectrum or other analytical data produced by the MS system under predetermined operating conditions; a measurement of an abundance of ions of one or more selected mass-to-charge ratios taken while operating the MS system to analyze a sample; the presence of stationary phase material separated from a stationary phase support of the column; the composition of a sample matrix to be flowed through the column; the composition of a stationary phase supported in the column; an inside diameter of the column; the reactivity of one or more components of the sample matrix with the conditioning gas; and a combination of two or more of the foregoing.

52. The MS system of embodiment 40, comprising a heating device configured for varying a temperature of a column or a temperature in a housing according to a temperature profile, wherein the housing communicates with the sample interface, and the means for regulating respective flows is configured for maintaining the flow of the conditioning gas at a constant flow rate while the temperature is varied.

53. The MS system of embodiment 40, comprising an ionization device operative in the ionization chamber, a mass analyzer communicating with the ionization chamber, and an ion detector communicating with the mass analyzer, wherein the means for regulating respective flows is configured for regulating based on a desired ratio of the abundance of conditioning gas ions to the abundance of carrier gas ions as measured by operating the ionization device, the mass analyzer, and the ion detector.

54. The MS system of embodiment 53, wherein the means for regulating respective flows is configured for comparing a measured ratio of the abundance of conditioning gas ions to the abundance of carrier gas ions with the desired ratio to determine whether a ratio difference between measured ratio and the desired ratio falls outside a desired range, and adjusting the flow of the conditioning gas relative to the carrier gas into the ionization chamber to maintain the ratio difference within the desired range.

55. A method for operating a mass spectrometer (MS) system, the method comprising:
introducing a sample and a carrier gas into an ionization chamber of the MS system;
while introducing the sample and the carrier gas, flowing a conditioning gas into a mass spectrometer of the MS system, wherein the conditioning gas is different from the carrier gas; and
ionizing components of the sample in the ionization chamber, wherein the conditioning gas in the mass spectrometer does not substantially change the mass spectral characteristics of analytes of the sample.

56. The method of embodiment 55, wherein the carrier gas is selected from the group consisting of helium, nitrogen, and argon.

57. The method of embodiment 55 or 56, wherein the conditioning gas is flowed from a source containing a blend of the conditioning gas and an auxiliary gas different from the conditioning gas.

58. The method of embodiment 57, wherein the proportion of the auxiliary gas in the source ranges from 0% to less than 100% by volume.

59. The method of embodiment 57, wherein the auxiliary gas is the same as the carrier gas.

60. The method of any one of embodiments 55-59, comprising mixing the flow of the carrier gas with the flow of the conditioning gas at a point upstream of the ionization chamber, wherein mixing comprises a step selected from the group consisting of: flowing the conditioning gas with the carrier gas into a column inlet of a column; flowing the conditioning gas into a section of the column between the column inlet and a column outlet of the column; and a combination of both of the foregoing.

61. The method of any one of embodiments 55-59, comprising mixing the flow of the carrier gas with the flow of the conditioning gas at the mass spectrometer, wherein mixing comprises a step selected from the group consisting of: flowing the conditioning gas into a conduit of a sample interface of the MS system through which a column extends, wherein the conduit and the column communicate separately with the ionization chamber; flowing the conditioning gas directly into the mass spectrometer via a gas line separate from the column; and a combination of both of the foregoing.

62. The method of any one of embodiments 55-59, wherein the conditioning gas and the carrier gas are flowed through a column and into the ionization chamber, and comprising regulating respective flows of the carrier gas and the conditioning gas into the column inlet such that the proportion of the carrier gas relative to the conditioning gas flowing through the column ranges from 0% to less than 100%.

63. The method of any one of embodiments 55-59, wherein the conditioning gas is flowed into a section of a column between a column inlet and a column outlet of the column, through the column and into the ionization chamber, and comprising flowing an auxiliary gas with the conditioning gas into the section, and regulating the flow of the auxiliary gas relative to the flow of the conditioning gas such that the proportion of the auxiliary gas flowing into the section ranges from 0% to less than 100%.

64. The method of embodiment 63, wherein the auxiliary gas is the same as the carrier gas.

65. The method of any one of embodiments 55-59, wherein the MS system comprises a sample interface through which a column extends, and the sample interface comprises a conduit communicating with the ionization chamber, and wherein the conditioning gas is flowed through the conduit and into the ionization chamber, and comprising flowing a reagent gas through the conduit and into the ionization chamber to perform chemical ionization, wherein the reagent gas is different from the conditioning gas.

66. The method of any one of embodiments 55-65, comprising regulating the flows of the carrier gas and the conditioning gas such that the proportion of the carrier gas flowing into the ionization chamber ranges from 0% to less than 100% by volume.

67. The method of any one of embodiments 55-66, comprising evaluating a parameter of the MS system, and regulating the flow of the conditioning gas based on the parameter.

68. The method of embodiment 67, wherein the parameter is selected from the group consisting of: a number of times a component of the MS housing has been operated to perform sample analyses prior to evaluating the parameter; an amount of time elapsed prior to evaluating the parameter; a quality of a chromatogram, mass spectrum or other analytical data produced by the MS system under predetermined operating conditions; a signal-to-noise ratio of a chromatogram, mass spectrum or other analytical data produced by the MS system under predetermined operating conditions; a measurement of an abundance of ions of one or more selected mass-to-charge ratios taken while operating the MS system to analyze a sample; the presence of stationary phase material separated from a stationary phase support of the column; the composition of a sample matrix to be flowed through the column; the composition of a stationary phase supported in the column; an inside diameter of the column; the reactivity of one or more components of the sample matrix with the conditioning gas; and a combination of two or more of the foregoing.

69. The method of any one of embodiments 55-68, comprising varying a temperature of a column or a temperature in a housing in which the column is disposed according to a temperature profile, and maintaining the flow of the conditioning gas at a constant flow rate while varying the temperature.

70. The method of any one of embodiments 55-69, wherein the MS system comprises an ionization device operative in the ionization chamber, a mass analyzer communicating with the ionization chamber, and an ion detector communicating with the mass analyzer, and comprising regulating the flow of the conditioning gas relative to the carrier gas into the ionization chamber based on a desired ratio of the abundance of conditioning gas ions to the abundance of carrier gas ions as measured by operating the ionization device, the mass analyzer, and the ion detector.

71. The method of embodiment 70, comprising comparing a measured ratio of the abundance of conditioning gas ions to the abundance of carrier gas ions with the desired ratio to determine whether a ratio difference between measured ratio and the desired ratio falls outside a desired range, and adjusting the flow of the conditioning gas relative to the carrier gas into the ionization chamber to maintain the ratio difference within the desired range.

72. The method of any one of embodiments 55-71, comprising flowing the sample and the carrier gas flow through a stationary phase of a column to produce a mixture of the carrier gas and separated components of the sample, splitting the mixture into a first output flow directed into the ion source and a second flow directed to a gas detector separate from an ion detector associated with the ion source, producing respective chromatograms or other analytical data from the ion detector and the gas detector, and regulating the flow of the conditioning gas relative to the carrier gas into the ionization chamber based on comparing the respective chromatograms or other analytical data.

73. A mass spectrometer (MS) system, comprising:
a mass spectrometer comprising a sample interface and an ionization chamber communicating with the sample interface;
a carrier gas line communicating with the sample interface and configured for supplying a carrier gas selected from the group consisting of hydrogen, argon, ammonia, and methane;
an auxiliary gas line configured for adding an auxiliary gas to the carrier gas, wherein the auxiliary gas is different from the carrier gas; and
means for regulating respective flows of the carrier gas and the auxiliary gas into the ionization chamber.

74. The MS system of embodiment 73, wherein the auxiliary gas is selected from the group consisting of helium, nitrogen, and argon.

75. The MS system of embodiment 73, wherein the carrier gas line is configured for supplying the carrier gas blended with another gas different from the carrier gas.

76. The MS system of embodiment 75, wherein the proportion of the other gas in the blend ranges from 0% to less than 100% by volume.

77. The MS system of embodiment 75, wherein the other gas that is blended with the carrier gas is the same as the auxiliary gas.

78. A method for operating a mass spectrometer (MS) system, the method comprising:
flowing a sample and a carrier gas into an ionization chamber of the MS system, the carrier gas selected from the group consisting of hydrogen, argon, ammonia, and methane;
while flowing the sample and the carrier gas, flowing an auxiliary gas into the ionization chamber, wherein the auxiliary gas is different from the carrier gas; and
ionizing components of the sample in the ionization chamber.

79. The method of embodiment 78, wherein the auxiliary gas is selected from the group consisting of helium, nitrogen, and argon.

80. The method of embodiment 78, wherein the carrier gas is flowed from a source containing a blend of the carrier gas and another gas different from the carrier gas.

81. The method of embodiment 80, wherein the proportion of the other gas in the blend therewith ranges from 0% to less than 100% by volume.

82. The method of embodiment 80, wherein the other gas that is blended with the carrier gas is the same as the auxiliary gas.

83. A method for operating a mass spectrometer (MS) system, the method comprising:
flowing a sample and a hydrogen through a column and into an ionization chamber of the MS system;
while flowing the sample and the hydrogen, flowing an auxiliary gas into a mass spectrometer of the MS system, wherein the auxiliary gas is selected from the group consisting of helium, nitrogen, and argon; and
ionizing components of the sample in the ionization chamber.

84. The method of embodiment 83, wherein the auxiliary gas is helium.

85. The method of embodiment 83, wherein the hydrogen is flowed with the auxiliary gas from a source containing a blend of the hydrogen and the auxiliary gas.

86. The method of embodiment 83, wherein flowing the auxiliary gas into the mass spectrometer comprises a step selected from the group consisting of: flowing the auxiliary gas with the hydrogen into a column inlet of the column; flowing the auxiliary gas into a section of the column between the column inlet and a column outlet of the column; flowing the auxiliary gas into a conduit of a sample interface of the MS system, wherein the conduit and the column communicate separately with the ionization chamber; flowing the auxiliary gas directly into the mass spectrometer via a gas line separate from the column; and a combination of two or more of the foregoing.

87. The method of embodiment 83, comprising regulating a flow of the auxiliary gas in the mass spectrometer relative to a flow of the hydrogen into the ionization chamber such that the proportion of the auxiliary gas flow ranges from 0% to less than 100%.

88. The method of embodiment 83, comprising operating the mass spectrometer to measure a ratio of the abundance of carrier gas ions to the abundance of auxiliary gas ions, and regulating the flow of the auxiliary gas into the mass spectrometer based on the measured ratio.

89. A mass spectrometer (MS) system, configured for performing the method of embodiment 83.

90. A method for operating a mass spectrometer (MS) system, the method comprising flowing a conditioning gas into a mass spectrometer of the MS system without flowing a sample into the mass spectrometer.

91. The method of embodiment 90, comprising ionizing one or more molecules in the mass spectrometer while flowing the conditioning gas.

92. The method of any one of the preceding claims, wherein the conditioning gas is flowed directly into the ionization chamber.

93. A method for operating a mass spectrometer (MS) system, the method comprising introducing a sample and a carrier gas into the MS system, wherein the carrier gas is a blend of helium and hydrogen.

94. The MS system or method of any one of the preceding claims, wherein the MS system does not comprise a plasma ion source.

95. The MS system or method of any one of the preceding claims, wherein the MS system comprises an ion mobility spectrometer (IMS), and the conditioning gas is not introduced into the IMS.

96. The MS system or method of any one of claims 1-94, wherein the MS system does not comprise an IMS.

97. A computer-readable storage medium comprising instructions for performing the method of any one of the preceding claims.

98. An MS system comprising the computer-readable storage medium of embodiment 97.

From the foregoing, it can be seen the embodiments described herein may eliminate—or significantly lower the frequency of—conventional MS servicing tasks, such as removal, ex-situ cleaning, and re-installation of contaminated parts, and restore or improve the performance of an MS system. Application of an off-line, on-line, or both off-line and on-line conditioning process as described herein may rapidly improve the background of the MS system, including with respect to chemically adsorbed species such as water which otherwise would have a very slow rate of elimination, and species such as the solvents or hydrocarbons adsorbed on MS components upon exposure to air during conventional cleaning It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 168 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 168 in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for operating a mass spectrometer (MS) system, the method comprising:
   introducing a sample and a carrier gas into an ionization chamber of the MS system; and
   flowing a conditioning gas into the MS system, the conditioning gas comprising hydrogen gas, wherein the conditioning gas in the MS system does not substantially change the mass spectral characteristics of analytes of the sample, and the carrier gas does not comprise hydrogen gas.

2. The method of claim 1, wherein the MS system comprises a collision cell.

3. The method of claim 2, wherein the conditioning gas is flowed directly into the collision cell.

4. The method of claim 2, wherein the conditioning gas is flowed into the MS system upstream from the collision cell.

5. The method of claim 2, wherein the conditioning gas is flowed into the MS system downstream from the collision cell.

6. The method of claim 1, wherein the conditioning gas is flowed directly into an ion detector of the MS system.

7. The method of claim 1, wherein the carrier gas comprises helium.

8. The method of claim 1, wherein the carrier gas is helium and the conditioning gas is hydrogen.

9. The method of claim 1, wherein the conditioning gas is flowed into two or more locations in the MS system.

10. The method of claim 9, wherein said two or more locations include a collision cell.

11. A method for operating an MS system, the method comprising:

flowing a conditioning gas into a mass spectrometer of the MS system without introducing a sample into the mass spectrometer, wherein the mass spectrometer is conditioned by the conditioning gas; and introducing a sample with a carrier gas into the conditioned mass spectrometer and collecting analytical data from the sample, wherein the carrier gas does not comprise hydrogen gas, and the conditioning gas comprises hydrogen gas or ammonia.

12. The method of claim 11, wherein the carrier gas comprises helium.

13. The method of claim 11, wherein the conditioning gas comprises hydrogen.

14. The method of claim 11, wherein the carrier gas is helium and the conditioning gas is hydrogen.

15. The method of claim 11, wherein the MS system comprises a collision cell.

16. The method of claim 15, wherein the conditioning gas is flowed directly into the collision cell.

17. The method of claim 11, wherein the conditioning gas is flowed directly into an ion detector of the MS system.

18. The method of claim 11, wherein the conditioning gas is flowed into two or more locations in the MS system.

19. The method of claim 18, wherein said two or more locations include a collision cell.

20. The method of claim 18, wherein said two or more locations include an ion detector.

* * * * *